(12) United States Patent
Doi et al.

(10) Patent No.: US 8,975,045 B2
(45) Date of Patent: Mar. 10, 2015

(54) MUTANT RPSA GENE AND METHOD FOR PRODUCING L-AMINO ACID

(75) Inventors: Hidetaka Doi, Kawasaki (JP); Yusuke Hagiwara, Kawasaki (JP); Yoshihiro Usuda, Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 113 days.

(21) Appl. No.: 13/569,264

(22) Filed: Aug. 8, 2012

(65) Prior Publication Data

US 2013/0005000 A1 Jan. 3, 2013

Related U.S. Application Data

(63) Continuation of application No. PCT/JP2011/052469, filed on Feb. 7, 2011.

(30) Foreign Application Priority Data

Feb. 8, 2010 (JP) .................................. 2010-025000

(51) Int. Cl.
| | | |
|---|---|---|
| C12P 13/04 | (2006.01) | |
| C12N 1/21 | (2006.01) | |
| C12N 15/31 | (2006.01) | |
| C07K 14/24 | (2006.01) | |
| C12P 13/08 | (2006.01) | |
| C07K 14/245 | (2006.01) | |

(52) U.S. Cl.
CPC ................. *C12P 13/04* (2013.01); *C07K 14/24* (2013.01); *C12P 13/08* (2013.01); *C07K 14/245* (2013.01)
USPC .... 435/108; 435/106; 435/252.3; 435/252.33

(58) Field of Classification Search
None
See application file for complete search history.

(56) References Cited

U.S. PATENT DOCUMENTS

| | | | |
|---|---|---|---|
| 7,695,946 B2 | 4/2010 | Usuda et al. | |
| 7,696,315 B2 | 4/2010 | Usuda et al. | |
| 7,811,798 B2 | 10/2010 | Rybak et al. | |
| 7,833,761 B2 | 11/2010 | Terashita et al. | |
| 8,030,036 B2 | 10/2011 | Van Dien et al. | |
| 8,076,111 B2 | 12/2011 | Fukui et al. | |
| 8,080,396 B2 | 12/2011 | Shiraga et al. | |
| 8,137,938 B2 | 3/2012 | Nagai et al. | |
| 8,192,963 B2 | 6/2012 | Nishio et al. | |
| 2002/0119549 A1 | 8/2002 | Moeckel et al. | |
| 2005/0233308 A1 | 10/2005 | Nishio et al. | |
| 2009/0093029 A1 | 4/2009 | Usuda et al. | |
| 2009/0203090 A1 | 8/2009 | Ptitsyn et al. | |
| 2009/0239269 A1 | 9/2009 | Tajima et al. | |
| 2009/0246835 A1 | 10/2009 | Iwatani et al. | |
| 2009/0291478 A1 | 11/2009 | Usuda et al. | |
| 2010/0047878 A1 | 2/2010 | Nagai et al. | |
| 2010/0112647 A1 | 5/2010 | Hara et al. | |
| 2010/0190217 A1 | 7/2010 | Doi et al. | |
| 2011/0014663 A1 | 1/2011 | Suzuki et al. | |
| 2011/0117613 A1 | 5/2011 | Hoshino et al. | |
| 2012/0040415 A1 | 2/2012 | Nakahara et al. | |

FOREIGN PATENT DOCUMENTS

| | | |
|---|---|---|
| EP | 2 202 299 | 6/2010 |
| EP | 2 497 832 | 9/2012 |
| WO | WO02/066651 | 8/2002 |
| WO | WO2011/096554 | 8/2011 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Introduction to Protein Structure, Garland Publishing Inc., New York, p. 247, 1991.*
Boni, I. V., et al., "The Last RNA-Binding Repeat of the *Escherichia coli* Ribosomal Protein S1 Is Specifically Involved in Autogenous Control," J. Bacteriol. 2000;182(20):5872-5879.
Sengupta, J., et al., "Visualization of protein S1 within the 30S ribosomal subunit and its interaction with messenger RNA," PNAS 2001;98(21):11991-11996.
Sørensen, M. A., et al., "Ribosomal Protein S1 is Required for Translation of Most, If Not All, Natural mRNAs in *Escherichia coli* in Vivo," J. Mol. Biol. 1998;280:561-569.
Sukhodolets, M. V., et al., "Ribosomal protein S1 promotes transcriptional cycling," RNA 2006;12(8):1505-1513.
International Preliminary Report on Patentability for PCT Patent App. No. PCT/JP2011/052469 (Sep. 27, 2012).
Rasmussen, M. D., et al., "Isolation and characterization of mutants with impaired regulation of *rpsA*, the gene encoding ribosomal protein S1 of *Escherichia coli*," Mol. Gen. Genet. 1993;240:23-28.
Schnier, J., et al., "Primary structure of *Escherichia coli* ribosomal protein S1 and of its gene *rpsA*," Proc. Natl. Acad. Sci. USA 1982;79:1008-1011.

(Continued)

*Primary Examiner* — Tekchand Saidha
*Assistant Examiner* — Md. Younus Meah
(74) *Attorney, Agent, or Firm* — Shelly Guest Cermak; Cermak Nakajima McGowan LLP

(57) ABSTRACT

A method for efficiently producing an L-amino acid utilizing a bacterium belonging to the family Enterobacteriaceae from a fatty acid or an alcohol such as glycerol as a raw material is provided. A bacterium belonging to the family Enterobacteriaceae which is able to produce L-amino acid and harbors an RpsA protein which has a mutation such that the native aspartic acid residue at position 210 is replaced with another amino acid residue is used. This bacterium is cultured in a medium containing a carbon source selected from a fatty acid and an alcohol, and the produced L-amino acid is collected from the medium.

11 Claims, 4 Drawing Sheets

(56) References Cited

OTHER PUBLICATIONS

Schnier, J., et al., "The DNA sequence of the gene rpsA [sic] of *Escherichia coli* coding for ribosomal protein S1," Nucleic Acids Res. 1982;10(6):1857-1865.

Schnier, J., et al., "Deletion and Insertion Mutants in the Structural Gene for Ribosomal Protein S1 from *Escherichia coli*," J. Biol. Chem. 1986;261(25):11866-11871.

International Search Report for PCT Patent App. No. PCT/JP2011/052469 (Apr. 26, 2011).

Fong, S. S., et al., "Parallel adaptive evolution cultures of *Escherichia coli* lead to convergent growth phenotypes with different gene expression states," Genome Research, vol. 15, pp. 1365-1372, 2005.

Supplementary European Search Report for European Patent App. No. 11739901.4 (Jul. 14, 2014).

\* cited by examiner

Fig. 6

```
E. coli         MTESFAQLFEESLKEIETRPGSIVRGVVVAIDKDVVLVDAGLKSESAIPA
E. aerogenes    MTESFAQLFEESLKEIETRPGSIVRGVVVAIDKDIVLVDAGLKSESAIPA
P. ananatis     MTESFAQLFEESLKEIETRPGSIVRGVVVSIDKDVVLVDAGLKSESAIPA
                *****************************:****:***************

E. coli         EQFKNAQGELEIQVGDEVDVALDAVEDGFGETLLSREKAKRHEAWITLEK
E. aerogenes    EQFKNAQGELEIQVGDEVDVALDAVEDGFGETLLSREKAKRHEAWITLEK
P. ananatis     EQFKNAAGELEIQVGDEVDVALDAVEDGFGETLLSREKAKRHEAWITLEK
                ****** ******************************************

E. coli         AYEDAETVTGVINGKVKGGFTVELNGIRAFLPGSLVDVRPVRDTLHLEGK
E. aerogenes    AYEDAETVVGVINGKVKGGFTVELNGIRAFLPGSLVDVRPVRDTLHLEGK
P. ananatis     AYEEAETVTGIINGKVKGGFTVELNGIRAFLPGSLVDVRPVRDTLHLEGK
                ***:****.*:***************************************

E. coli         ELEFKVIKLDQKRNNVVVSRRAVIESENSAERDQLLENLQEGMEVKGIVK
E. aerogenes    ELEFKVIKLDQKRNNVVVSRRAVIESENSAERDQLLENLQEGMEVKGIVK
P. ananatis     ELEFKVIKLDQKRNNVVVSRRAVIESENSAERDQLLENLQEGMEVKGIVK
                **************************************************

E. coli         NLTDYGAFVDLGGVDGLLHITDMAWKRVKHPSEIVNVGDEITVKVLKFDR
E. aerogenes    NLTDYGAFVDLGGVDGLLHITDMAWKRVKHPSEIVNVGDEITVKVLKFDR
P. ananatis     NLTDYGAFVDLGGVDGLLHITDMAWKRVKHPSEIVNVGDEINVKVLKFDR
                ****************************************.********

E. coli         ERTRVSLGLKQLGEDPWVAIAKRYPEGTKLTGRVTNLTDYGCFVEIEEGV
E. aerogenes    ERTRVSLGLKQLGEDPWVAIAKRYPEGTKLTGRVTNLTDYGCFVEIEEGV
P. ananatis     ERTRVSLGLKQLGEDPWVAIAKRYPEGTKLTGRVTNLTDYGCFVEIEEGV
                **************************************************

E. coli         EGLVHVSEMDWTNKNIHPSKVVNVGDVVEVMVLDIDEERRRISLGLKQCK
E. aerogenes    EGLVHVSEMDWTNKNIHPSKVVNVGDVVEVMVLDIDEERRRISLGLKQCK
P. ananatis     EGLVHVSEMDWTNKNIHPSKVVNVGDVVEVMVLDIDEERRRISLGLKQCK
                **************************************************

E. coli         ANPWQQFAETHNKGDRVEGKIKSITDFGIFIGLDGGIDGLVHLSDISWNV
E. aerogenes    SNPWQQFAETHNKGDRVEGKIKSITDFGIFIGLDGGIDGLVHLSDISWNV
P. ananatis     SNPWQQFAETHNKGDRVEGKIKSITDFGIFIGLDGGIDGLVHLSDISWNA
                :************************************************.

E. coli         AGEEAVREYKKGDEIAAVVLQVDAERERISLGVKQLAEDPFNNWVALNKK
E. aerogenes    AGEEAVREYKKGDEIAAVVLQVDAERERISLGVKQLAEDPFNNYVALNKK
P. ananatis     TGEEAVREYKKGDEIAAVVLQVDAERERISLGVKQLAEDPFNNYITLNKK
                :**************************************:::****

E. coli         GAIVTGKVTAVDAKGATVELADGVEGYLRASEASRDRVEDATLVLSVGDE
E. aerogenes    GAIVTGKVTAVDAKGATVELADGVEGYLRASEASRDRVEDATLVLSVGDE
P. ananatis     GAIVTGKVTAVDAKGATVELADGVEGYLRASEASLDRIEDATLVLNVGDD
                ********************************** **:*******.***:

E. coli         VEAKFTGVDRKNRAISLSVRAKDEADEKDAIATVNKQEDANFSNNAMAEA
E. aerogenes    VEAKFTGVDRKNRAISLSVRAKDEADEKDAIATVNKQEDANFSNNAMAEA
P. ananatis     VEAKFTGVDRKNRVVSLSVRAKDQADEKEAINTVNTKQEEGNFSSAMAEA
                *************.:*******:****:** ***.:::   .,*****

E. coli         FKAAKGE
E. aerogenes    FKAAKGE
P. ananatis     FKAAKGE
                *******
```

MUTANT RPSA GENE AND METHOD FOR PRODUCING L-AMINO ACID

This application is a Continuation of, and claims priority under 35 U.S.C. §120 to, International Application No. PCT/JP2011/052469, filed Feb. 7, 2011, and claims priority therethrough under 35 U.S.C. §119 to Japanese Patent Application No. 2010-025000, filed Feb. 8, 2010, the entireties of which are incorporated by reference herein. Also, the Sequence Listing filed electronically herewith is hereby incorporated by reference (File name: 2012-08-08T_US-486_Seq_List; File size: 58 KB; Date recorded: Aug. 8, 2012).

BACKGROUND OF THE INVENTION

1. Technical Field

The present invention relates to a method for producing an L-amino acid utilizing a bacterium and, in particular, a method for producing an L-amino acid utilizing a fatty acid or an alcohol such as glycerol as a raw material. The present invention also related to a bacterium which can be used in the method, and a gene which can be used for construction of the bacterium. L-Amino acids are industrially useful as additives for animal feeds, components of health foods, amino acid infusions, and so forth.

2. Background Art

In the industrial production of L-amino acids by fermentation, saccharides, i.e., glucose, fructose, sucrose, blackstrap molasses, starch hydrolysate, and so forth, are used as a carbon source. Moreover, methods for producing an L-amino acid using a fatty acid (International Patent Publication WO2009/142286) and glycerol (U.S. Patent Published Application No. 2009/093029) as a carbon source have been disclosed.

For Escherichia bacteria belonging to the family Enterobacteriaceae, a method has been reported for inducing adaptive evolution by performing subcultures under a specific condition (Fong, S. S. et al., 2005, Genome Res., 15:1365-1372, etc.). Moreover, in the chromosome of an adaptive evolution-induced bacterium, the mutation corresponding to the evolution can be searched for and identified by such a method as the CGS method described in Herring, C. D. et al., 2006, Nat. Genet., 38:1406-1412.

The RpsA protein is also called ribosomal protein S1, and it is indispensable for the growth of Escherichia coli (Sorensen, M. A. et al., 1998, J. Mol. Biol., 280(4):561-569). The RpsA protein is known as the largest protein among the proteins which constitute the 30S subunit of the ribosome, and it is known to control binding of the 16S rRNA in the 30S subunit and the SD sequence in mRNA (Komarova, A. V. et al., 2002, RNA, 8(9):1137-1147).

However, the ability to utilize fatty acids and alcohols such as glycerol, and abilities to produce L-amino acids from these carbon sources via adaptive evolution has not been analyzed, and the relation between mutation of the bacterial RpsA protein and L-amino acid productivity has not previously been reported.

SUMMARY OF THE INVENTION

It is an aspect of the present invention to provide a method for efficiently producing an L-amino acid utilizing a bacterium belonging to the family Enterobacteriaceae from a carbon source, especially a fatty acid or an alcohol such as glycerol, as a raw material, a bacterium used for the method, and a gene used for construction of the bacterium. A bacterium that harbors and expresses the RpsA protein which has a specific mutation has been found to efficiently produce an L-amino acid in a medium containing a fatty acid or an alcohol such as glycerol.

It is an aspect of the present invention to provide a method for producing an L-amino acid comprising culturing a bacterium belonging to the family Enterobacteriaceae and having an L-amino acid-producing ability in a medium containing a carbon source selected from the group consisting of a fatty acid and an alcohol; and collecting the L-amino acid from the medium, wherein the bacterium expresses an RpsA protein comprising the amino acid sequence of SEQ ID NO: 15 or 16, wherein said RpsA protein has a mutation in which the aspartic acid residue at position 5 of SEQ ID NO: 15 or 16 is replaced with a different amino acid residue.

It is a further aspect of the present invention to provide the method as described above, wherein the bacterium belongs to a genus selected from the group consisting of Escherichia, Enterobacter, and Pantoea.

It is a further aspect of the present invention to provide the method as described above, wherein the bacterium is selected from the group consisting of Escherichia coli, Pantoea ananatis, and Enterobacter aerogenes.

It is a further aspect of the present invention to provide the method as described above, wherein the RpsA protein originates or is derived from a bacterium belonging to the family Enterobacteriaceae.

It is a further aspect of the present invention to provide the method as described above, wherein the mutant RpsA protein originates or is derived from a bacterium selected from the group consisting of Escherichia coli, Pantoea ananatis, and Enterobacter aerogenes.

It is a further aspect of the present invention to provide the method as described above, wherein the different amino acid residue is a tyrosine residue.

It is a further aspect of the present invention to provide the method as described above, wherein the RpsA protein is a protein comprising the amino acid sequence of SEQ ID NO: 17 or a conservative variant thereof, but comprises said mutation.

It is a further aspect of the present invention to provide the method as described above, wherein the bacterium does not express an RpsA protein not having the mutation.

It is a further aspect of the present invention to provide the method as described above, wherein the chromosome of said bacterium expresses a mutant rpsA gene coding for the mutant RpsA protein.

It is a further aspect of the present invention to provide the method as described above, wherein the carbon source is a fatty acid.

It is a further aspect of the present invention to provide the method as described above, wherein the fatty acid is oleic acid.

It is a further aspect of the present invention to provide the method as described above, wherein the fatty acid is a mixture of fatty acids derived from fat or oil.

It is a further aspect of the present invention to provide the method as described above, wherein the carbon source is an alcohol.

It is a further aspect of the present invention to provide the method as described above, wherein the alcohol is glycerol.

It is a further aspect of the present invention to provide the method as described above, wherein the alcohol is ethanol.

It is a further aspect of the present invention to provide the method as described above, wherein the carbon source is a mixture of a fatty acid and glycerol obtained by hydrolyzing fat or oil.

It is a further aspect of the present invention to provide a bacterium belonging to the family Enterobacteriaceae, and expressing a RpsA protein comprising the amino acid sequence of SEQ ID NO: 15 or 16, wherein said protein comprise a mutation in which the aspartic acid residue at position 5 of SEQ ID NO: 15 or 16 is replaced with a different amino acid residue.

It is a further aspect of the present invention to provide the bacterium as described above, which has an L-amino acid-producing ability.

It is a further aspect of the present invention to provide the bacterium as described above, which belongs to a genus selected from the group consisting of *Escherichia, Enterobacter*, and *Pantoea*.

It is a further aspect of the present invention to provide the bacterium as described above, which is selected from the group consisting of *Escherichia coli, Pantoea ananatis*, and *Enterobacter aerogenes*.

It is a further aspect of the present invention to provide the bacterium as described above, wherein the different amino acid residue is a tyrosine residue.

It is a further aspect of the present invention to provide the bacterium as described above, wherein the RpsA protein is a protein comprising the amino acid sequence of SEQ ID NO: 17 or a conservative variant thereof, but comprises said mutation.

It is a further aspect of the present invention to provide a DNA coding for a protein comprising the amino acid sequence of SEQ ID NO: 17, or a conservative variant thereof, wherein said protein has a mutation in which the aspartic acid residue at position 210 is replaced with a different amino acid residue.

It is a further aspect of the present invention to provide a DNA as described above, wherein the different amino acid residue is a tyrosine residue.

It is a further aspect of the present invention to provide a DNA as described above, wherein the protein comprises the amino acid sequence of SEQ ID NO: 2, 12, or 14, but comprises said mutation.

It is a further aspect of the present invention to provide a DNA as mentioned above, wherein the protein has a function of improving growth of a bacterium belonging to the family Enterobacteriaceae in a medium containing a carbon source selected from a fatty acid and an alcohol, when the protein is expressed by the bacterium cultured in said medium.

According to the present invention, an L-amino acid such as L-lysine can be efficiently produced by using a fatty acid or an alcohol such as glycerol as a raw material and using a bacterium belonging to the family Enterobacteriaceae.

BRIEF DESCRIPTION OF THE DRAWINGS

FIG. 6 shows alignment of the amino acid sequences of the RpsA proteins of the *Escherichia coli* MG1655 strain (SEQ ID NO: 2), *Pantoea ananatis* AJ13355 strain (SEQ ID NO: 12), and *Enterobacter aerogenes* AJ110637 strain (SEQ ID NO: 14). The symbol "*" mentioned in the lowest row means the same amino acid residues, ":" means amino acid residues of a high similarity group, "." means amino acid residues of a low similarity group, and blank means amino acid residues of no similarity. The basis of degree of the similarity of amino acid residues was graded by determining whether the score between the amino acid residues obtained by using the amino acid substitution matrix PAM250 MATRIX (David W. Mount, Bioinformatics: Sequence and Genome Analysis) is larger than 0.5 or not larger than 0.5.

DESCRIPTION OF THE PREFERRED EMBODIMENTS

Figure 1:
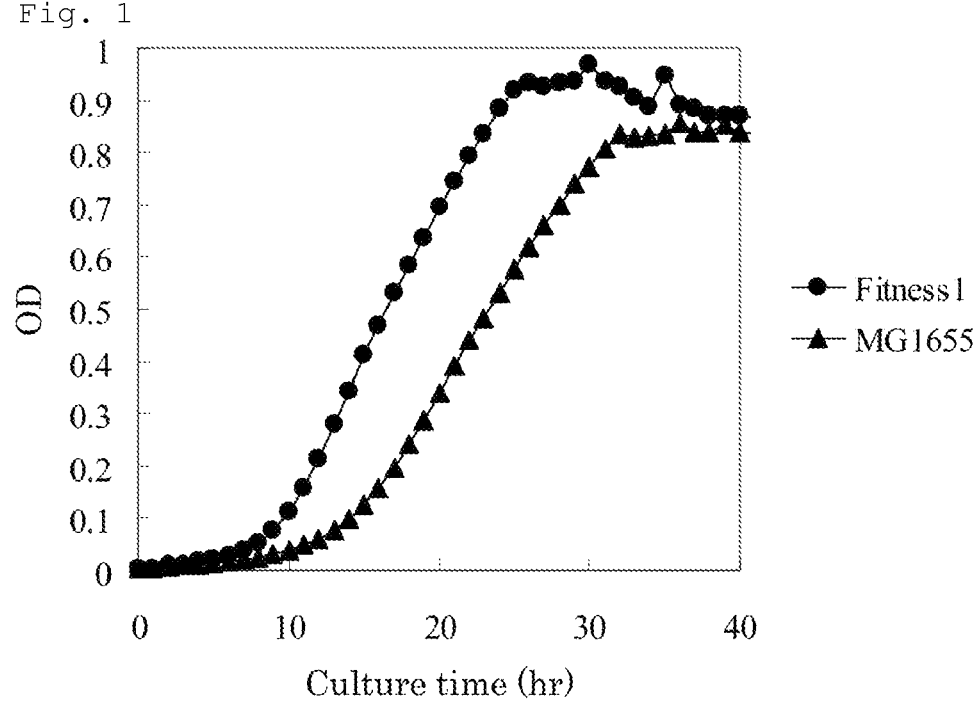
FIG. 1 shows growth of the MG1655 strain and the Fitness 1 strain in test tube culture using only oleate as a carbon source. "OD" means turbidity of the medium measured at a wavelength of 600 nm (the same shall apply to the following drawings).

The method in accordance with the presently described subject matter is a method for producing an L-amino acid, which includes the steps of culturing a bacterium belonging to the family Enterobacteriaceae which is able to produce an L-amino acid in a medium containing a carbon source such as a fatty acid and an alcohol, and collecting the L-amino acid from the medium. A bacterium harboring an rpsA gene having a specific mutation (henceforth also referred to as "DNA of the present invention") is used.

Hereafter, the DNA, the bacterium harboring the DNA, and the method for producing an L-amino acid using the bacterium will be explained.

<1> DNA in accordance with the presently disclosed subject matter

The DNA codes for an RpsA protein which includes the amino acid sequence of SEQ ID NO: 15 or 16, and has been mutated so that the native aspartic acid residue at position 5 of SEQ ID NO: 15 or 16 is replaced with another amino acid residue. The amino acid sequence of SEQ ID NO: 15 or 16 is a part of the functional domain that binds to RNA, and is a part of the third motif from the N-terminus in the S1 RNA binding domains which are repeated 6 times in the S1 protein of *E. coli*. The S1 RNA binding domain is described in Cell, Vol. 88, Issue 2, Jan. 24, 1997, Pages 235-242.

The RpsA protein is the largest protein among those proteins constituting the 30S ribosome subunit of bacteria, and has the conserved sequence of SEQ ID NO: 15 or 16. The mutant RpsA protein can mean a protein in which the aspartic acid residue at position 5 in the conserved sequence of SEQ ID NO: 15 or 16 is replaced with another amino acid residue, and is distinguished from an RpsA protein not having the mutation, which can be referred to as "wild-type RpsA protein".

The wild-type RpsA protein can be any protein having the conserved sequence of SEQ ID NO: 15 or 16, and can also be a protein having a conservative mutation such as a homologue or artificial modification thereof, so long as the protein has the conserved sequence, and the function as the RpsA protein is not degraded. Examples of the function of the RpsA protein can include improving the growth of a bacterium belonging to the family Enterobacteriaceae in a medium containing a carbon source such as a fatty acid or an alcohol, when the protein is harbored by the bacterium, or the amount of the protein is increased in the bacterium. Examples of the wild-type RpsA protein can include the RpsA proteins of bacteria belonging to the family Enterobacteriaceae, coryneform bacteria, and so forth. The bacteria belonging to the family Enterobacteriaceae will be described later.

As the wild-type RpsA protein, specifically, the genes coding for the RpsA proteins of *Escherichia coli, Pantoea ananatis*, and *Enterobacter aerogenes* can be used.

The RpsA protein of *Escherichia coli* is registered as GenBank Accession No. NP_415431, and the amino acid sequence is shown in SEQ ID NO: 2. The nucleotide sequence of the rpsA gene coding for the protein is shown in SEQ ID NO: 1.

The amino acid sequences of the RpsA proteins of the *Pantoea ananatis* AJ13355 strain and the *Enterobacter aerogenes* AJ110637 strain are shown in SEQ ID NOS: 12 and 14, respectively. The nucleotide sequences of the rpsA genes coding for these proteins are shown in SEQ ID NOS: 11 and 13, respectively.

Each of the aforementioned wild-type RpsA proteins of *Escherichia coli, Pantoea ananatis* and *Enterobacter aerogenes* has the conserved sequence of SEQ ID NO: 17. Alignment of the amino acid sequences of these RpsA proteins (created with CLUSTAL W (1.83) Multiple Sequence Alignment) is shown in FIG. 6. The RpsA proteins having the conserved sequence of SEQ ID NO: 17 are examples of the wild-type RpsA protein.

Moreover, in addition to the proteins as described above, the wild-type RpsA protein can also be a homologue or artificial modification thereof, or a protein having a conservative mutation, so long as the function as the RpsA protein is not degraded. Such a homologue, an artificial modification, or a protein having a conservative mutation is referred to as conservative variant.

The conservative variant of the RpsA protein can be, for example, a protein having the amino acid sequence of SEQ ID NO: 2, 12, 14, or 17, but which can include substitution, deletion, insertion, addition, or the like of one or several amino acid residues at one or several positions.

Although the number meant by the term "one or several" can differ depending on the positions of amino acid residues in the three-dimensional structure or the types of amino acid residues of the protein, specifically, it can be 1 to 20, 1 to 10, or even 1 to 5. The conservative mutation is typically a conservative substitution. The conservative substitution is a mutation wherein substitution takes place mutually among Phe, Trp, and Tyr, if the substitution site is an aromatic amino acid; among Leu, Ile and Val, if the substitution site is a hydrophobic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having a hydroxyl group. Substitutions considered conservative substitutions include, specifically, substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Be, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Be or Leu for Val. The aforementioned amino acid substitutions, deletions, insertions, additions, inversions or the like can be a result of a naturally-occurring mutation due to an individual difference, difference of species, or the like, of a microorganism from which the genes are derived (mutant or variant). Such a protein can be obtained by, for example, modifying the nucleotide sequence of a wild-type rpsA gene by site-specific mutagenesis so that the amino acid residues at the specific sites of the encoded protein include substitutions, deletions, insertions, or additions of amino acid residues.

Furthermore, such an RpsA protein having a conservative mutation as mentioned above can be a protein showing a homology of, for example, 80% or more, 90% or more, 95% or more, 97% or more, 98% or more, or 99% or more, to the entire amino acid sequence, and being a function equivalent to that of the wild-type RpsA protein. In this specification, "homology" can mean "identity".

So long as the wild-type rpsA gene codes for such an amino acid sequence as mentioned above, it is not limited to the rpsA genes of *Escherichia coli, Pantoea* ananatis, and *Enterobacter aerogenes*, but it can be any of those having an equivalent codon for an arbitrary codon.

The wild-type rpsA gene can also be a DNA that is able to hybridize with a nucleotide sequence complementary to the nucleotide sequence of SEQ ID NO: 1, 11 or 13, or a probe that can be prepared from the complementary sequence, under stringent conditions, and codes for a protein having a function equivalent to that of the RpsA protein having the amino acid sequence of SEQ ID NO: 2, 12 or 14. The "stringent conditions" can refer to conditions under which a so-called specific hybrid is formed, and a non-specific hybrid is not formed. Examples of the stringent conditions can include those under which highly homologous DNAs hybridize to each other, for example, DNAs not less than 80% homologous, not less than 90% homologous, not less than 95% homologous, not less than 97% homologous, not less than 98% homologous, or not less than 99% homologous, hybridize to each other, and DNAs less homologous than the above do not hybridize to each other, or conditions of washing of typical Southern hybridization, i.e., conditions of washing once, or 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C.

As the probe, a part of a sequence that is complementary to the rpsA gene can also be used. Such a probe can be prepared by PCR using oligonucleotides prepared on the basis of a known gene sequence as primers and a DNA fragment containing these nucleotide sequences as a template. For example, when a DNA fragment having a length of about 300 bp is used as the probe, the washing conditions of the hybridization can be, for example, 50° C., 2×SSC and 0.1% SDS.

The aforementioned descriptions concerning conservative variants of the RpsA protein and rpsA genes coding for them are similarly applied to the other genes mentioned below for the L-amino acid-producing bacteria.

The aforementioned DNA coding for a mutant RpsA protein, which can also be referred to as "mutant rpsA gene", can be obtained by repeating a subculture of *Escherichia coli* in a medium containing a fatty acid such as sodium oleate as a carbon source, and isolating the rpsA gene from a strain showing improved fatty acid-utilizing ability, as shown in the examples. However, because the mutation site has now been clarified, the mutant rpsA gene can be obtained by chemical synthesis or by introducing such a mutation into a wild-type rpsA gene so that the aspartic acid residue at position 210 is replaced with another amino acid residue. Introduction of the mutation can be attained by replacing a corresponding part of a wild-type rpsA gene with a DNA fragment containing the mutation (cassette mutation method), or by the site-specific mutation method, crossover PCR method, or the like.

For example, by conducting PCR using the genomic DNA of a bacterium belonging to the family Enterobacteriaceae, for example, a wild-type *Escherichia coli* such as the MG1655 strain, as a template, and the synthetic oligonucleotides shown in SEQ ID NOS: 5 and 6 as primers, an rpsA gene fragment including the mutation that the aspartic acid residue at position 210 is replaced with a tyrosine residue (henceforth also indicated as "D210Y mutation") can be obtained. By changing the codons at the positions corresponding to the tyrosine residue in the primers to codons for another amino acid residue, the aspartic acid residue at position 210 can be replaced with another amino acid residue.

The "aspartic acid residue at position 210" can mean the aspartic acid residue at the position corresponding to position 210 in SEQ ID NO: 2. That is, the term "position 210" means a relative position. For example, if one amino acid residue is deleted on the N-terminus side of position 210, the 209th amino acid residue from the N-terminus (the methionine residue encoded by the start codon is also counted) shall be the amino acid residue at the "position 210". Furthermore, when one amino acid residue is inserted on the N-terminus side of position 210, the 211st amino acid residue from the N-terminus shall be the amino acid residue at the "position 210". The RpsA protein shown in SEQ ID NO: 2 contains the amino acid sequence of SEQ ID NO: 15 or 16, and the aspartic acid residue at position 210 in the amino acid sequence of SEQ ID NO: 2 corresponds to the aspartic acid residue at position 5 of SEQ ID NO: 15 or position 5 of SEQ ID NO: 16.

<2> Bacterium

The bacterium in accordance with the presently disclosed subject matter can be one belonging to the family Enterobacteriaceae, which is able to produce an L-amino acid, and harbors a mutant rpsA gene.

The L-amino acid-producing ability can refer to an ability of the bacterium, which can also be referred to as "bacterium of the present invention", to produce and accumulate an L-amino acid in a medium or the cells, when the bacterium is cultured in the medium. The bacterium having an L-amino acid-producing ability can be a bacterium inherently having an L-amino acid-producing ability, or can be a bacterium obtained by modifying such a bacterium as mentioned below so that it has an L-amino acid-producing ability using a mutagenesis method or a recombinant DNA method.

Although the L-amino acid is not particularly limited, examples can include basic amino acids such as L-lysine, L-ornithine, L-arginine, L-histidine and L-citrulline; aliphatic amino acids such as L-isoleucine, L-alanine, L-valine, L-leucine and L-glycine; amino acids which are hydroxy-monoaminocarboxylic acids such as L-threonine and L-serine; cyclic amino acids such as L-proline; aromatic amino acids such as L-phenylalanine, L-tyrosine and L-tryptophan; sulfur-containing amino acids such as L-cysteine, L-cystine, and L-methionine; acidic amino acids such as L-glutamic acid and L-aspartic acid; and amino acids having an amide group in the side chain such as L-glutamine and L-asparagine. The bacterium can have the ability to produce two or more kinds of amino acids.

The "L-amino acid" can include the L-amino acid in a free form and salts thereof, such as sulfate salt, hydrochloride salt, and carbonate salt.

Although the bacteria belonging to the family Enterobacteriaceae used for obtaining the bacterium of the present invention are not particularly limited, they can include bacteria belonging to the genera of *Escherichia, Enterobacter, Erwinia, Klebsiella, Pantoea, Photorhabdus, Providencia, Salmonella, Serratia, Shigella, Morganella, Yersinia*, and so forth. In particular, bacteria classified into the family Enterobacteriaceae according to the taxonomy used by the NCBI (National Center for Biotechnology Information) database (www.ncbi.nlm.nih.gov/Taxonomy/Browser/wwwtax-.cgi?id=91347) can be used.

A bacterium belonging to the genus *Escherichia* can mean that the bacterium is classified into the genus *Escherichia* according to classification known to a person skilled in the art of microbiology, although the bacterium is not particularly limited. Examples thereof include, for example, the bacteria of the phylesis described in the work of Neidhardt et al., Table 1 (Neidhardt F. C. Ed., 1996, *Escherichia coli* and *Salmonella*: Cellular and Molecular Biology/Second Edition, pp. 2477-2483, American Society for Microbiology Press, Washington, D.C.). Specific examples thereof include *Escherichia coli* W3110 (ATCC 27325), *Escherichia coli* MG1655 (ATCC 47076), and so forth, which are derived from the prototype wild-type strain, K12 strain.

These strains are available from, for example, American Type Culture Collection (Address: P.O. Box 1549 Manassas, Va. 20108, United States of America). That is, registration numbers are given to each of the strains, and the strains can be ordered by using these numbers. The registration numbers of the strains are listed in the catalogue of the American Type Culture Collection. The same shall apply to the strains mentioned below with registration numbers of ATCC.

A bacterium belonging to the genus *Pantoea* means that the bacterium is classified into the genus *Pantoea* according to classification known to a person skilled in the art of microbiology. Some of *Enterobacter agglomerans* have been recently re-classified into *Pantoea agglomerans, Pantoea ananatis, Pantoea stewartii*, or the like on the basis of the nucleotide sequence analysis of 16S rRNA etc. (Int. J. Syst. Bacteriol., 1993, 43, 162-173). In the present invention, bacteria belonging to the genus *Pantoea* can encompass such bacteria re-classified into the genus *Pantoea* as described above.

As *Pantoea ananatis*, the *Pantoea ananatis* AJ13355 strain (FERM BP-6614), AJ13356 strain (FERM BP-6615), AJ13601 strain (FERM BP-7207), and derivatives thereof can be used. These strains were identified as *Enterobacter agglomerans* when they were isolated, and deposited as *Enterobacter agglomerans*. However, they were re-classified into *Pantoea ananatis* on the basis of nucleotide sequence analysis of 16S rRNA etc as described above.

An *Enterobacter* bacterium means that the bacterium is classified into the genus *Enterobacter* according to classification known to a person skilled in the art of microbiology, although the bacterium is not particularly limited. Examples thereof include *Enterobacter agglomerans, Enterobacter aerogenes*, and the like. Specifically, the strains exemplified in European Patent Application Laid-open (EP-A) No. 952221 can be used. Examples of typical strains of the genus *Enterobacter* include the *Enterobacter agglomerans* ATCC 12287 strain, *Enterobacter aerogenes* ATCC 13048 strain, *Enterobacter aerogenes* NBRC 12010 strain (Biotechnol Bioeng., 2007, Mar. 27; 98(2):340-348), *Enterobacter aerogenes* AJ110637 (FERM ABP-10955) strain, and so forth.

<2-1> L-Amino Acid-Producing Bacteria and Impartation or Enhancement of L-Amino Acid-Producing Ability Hereafter, L-Amino acid-producing bacteria belonging to the family Enterobacteriaceae, and methods for imparting an L-amino acid-producing ability to bacteria or methods for enhancing an L-amino acid-producing ability of bacteria are described.

To impart an L-amino acid-producing ability, methods conventionally employed in the breeding of amino acid-producing strains of coryneform bacteria, *Escherichia* bacteria, and so forth (see "Amino Acid Fermentation", Gakkai Shuppan Center (Ltd.), 1st Edition, published May 30, 1986, pp. 77-100) can be used. Such methods include acquiring an auxotrophic mutant strain, an L-amino acid analogue-resistant strain, or a metabolic regulation mutant strain, or constructing a recombinant strain in which an L-amino acid biosynthetic enzyme is overexpressed. In the breeding of L-amino acid-producing bacteria, the above-described property(s) such as auxotrophy, analogue resistance, and metabolic regulation mutation can be imparted alone or in combinations of two, or three or more thereof. Expression of L-amino acid biosynthetic enzyme(s) can be enhanced alone or in combinations of two, or three or more thereof. Furthermore, imparting such properties as auxotrophy, analogue resistance, and metabolic regulation mutation can be combined with enhancing a biosynthetic enzyme.

An auxotrophic mutant strain, L-amino acid analogue-resistant strain, or metabolic regulation mutant strain, having an L-amino acid-producing ability can be obtained by subjecting a parent strain or wild-type strain to conventional mutagenesis, such as exposure to X-rays or UV irradiation or a treatment with a mutagen such as N-methyl-N'-nitro-N-nitrosoguanidine, and then selecting a strain exhibiting autotrophy, analogue resistance, or a metabolic regulation mutation, and having an L-amino acid-producing ability from the obtained mutant strains.

Moreover, the L-amino acid-producing ability can also be imparted or enhanced by increasing an enzymatic activity by gene recombination. Enhancement of an enzymatic activity can be attained by, for example, modifying a bacterium so that expression of a gene coding for an enzyme involved in the biosynthesis of an L-amino acid is enhanced. Expression of a gene can also be increased by introducing an amplification plasmid prepared by introducing a DNA fragment containing the gene into an appropriate plasmid, for example, a plasmid vector containing at least a gene responsible for replication and proliferation of the plasmid in microorganisms, increasing the copy number of the gene on a chromosome by conjugation, transfer, or the like, or introducing a mutation into the promoter region of the gene (refer to WO95/34672).

When an objective gene is introduced into the aforementioned amplification plasmid or chromosome, any promoter can be used to express the gene so long as the chosen promoter functions in Enterobacteriaceae bacteria. The promoter can be a native promoter for the gene, or a modified promoter. Expression amount of a gene can also be controlled by suitably choosing a promoter that strongly functions in Enterobacteriaceae bacteria, or by making the −35 and −10 regions of the promoter closer to the consensus sequence. These methods for enhancing expression of enzyme genes are described in WO00/18935, EP 1010755 A, and so forth.

Methods for imparting an L-amino acid-producing ability to bacteria and bacteria imparted with L-amino acid-producing ability are exemplified below.

L-Lysine-Producing Bacteria

Examples of L-lysine-producing bacteria of *Escherichia coli* include mutants having resistance to an L-lysine analogue. L-Lysine analogues inhibit growth of *Escherichia coli*, but this inhibition is fully or partially desensitized when L-lysine is present in a medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutant strains having resistance to these lysine analogues can be obtained by subjecting *Escherichia coli* to a conventional artificial mutagenesis treatment. Specific examples of bacterial strains useful for producing L-lysine include *Escherichia coli* AJ11442 (FERM BP-1543, NRRL B-12185, see U.S. Pat. No. 4,346,170) and *Escherichia coli* VL611. In these microorganisms, feedback inhibition of aspartokinase by L-lysine is desensitized.

The WC196 strain can be used as an L-lysine-producing bacterium of *Escherichia coli*. This bacterial strain was bred from the W3110 strain, which was derived from *Escherichia coli* K-12, by replacing the wild-type lysC gene on the chromosome of the W3110 strain with a mutant lysC gene encoding a mutant aspartokinase III in which threonine at position 352 had been replaced with isoleucine, resulting in desensitization of feedback inhibition by L-lysine (U.S. Pat. No. 5,661,012), and then imparting AEC resistance to the resulting strain (U.S. Pat. No. 5,827,698). This strain was designated *Escherichia coli* AJ13069 and was deposited at the National Institute of Bioscience and Human-Technology, Agency of Industrial Science and Technology (currently, independent administrative agency, National Institute of Advanced Industrial Science and Technology, International Patent Organism Depositary, Central 6, 1-1, Higashi 1-Chome, Tsukuba-shi, Ibaraki-ken, 305-8566, Japan) on Dec. 6, 1994 and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827,698).

Examples of L-lysine-producing bacteria and parent strains that can be used to derive such strains also include strains in which expression of one or more genes encoding an L-lysine biosynthetic enzyme is increased. Examples of such genes include, but are not limited to, dihydrodipicolinate synthase gene (dapA), aspartokinase gene (lysC), dihydrodipicolinate reductase gene (dapB), diaminopimelate decarboxylase gene (lysA), diaminopimelate dehydrogenase gene (ddh) (U.S. Pat. No. 6,040,160), phosphoenolpyruvate carboxylase gene (ppc), aspartate semialdehyde dehydrogenase gene (asd), and aspartase gene (aspA) (EP 1253195 A). In addition, the parent strains can have an increased level of expression of the gene involved in energy efficiency (cyo) (EP 1170376 A), the gene encoding nicotinamide nucleotide transhydrogenase (pntAB) (U.S. Pat. No. 5,830,716), the ybjE gene encoding a protein having L-lysine secretion activity (WO2005/073390), the gene coding for glutamate dehydrogenase (gdhA) (Gene, 1983, 23:199-209), or combinations thereof. Abbreviations of the genes are indicated in the parentheses.

It is known that the wild-type dihydrodipicolinate synthase derived from *Escherichia coli* suffers from feedback inhibition by L-lysine, and the wild-type aspartokinase derived from *Escherichia coli* suffers from expression suppression and feedback inhibition by L-lysine. Therefore, when the dapA and lysC genes are used, these genes can be mutant genes that do not suffer from the feedback inhibition by L-lysine.

Examples of DNA encoding a mutant dihydrodipicolinate synthase desensitized to feedback inhibition by L-lysine include a DNA encoding a protein that has the amino acid sequence in which the histidine residue at the position 118 is replaced by tyrosine residue. Examples of DNA encoding a mutant aspartokinase desensitized to feedback inhibition by L-lysine include a DNA encoding an AKIII having the amino acid sequence in which the threonine residue at the position 352, the glycine residue at the position 323, and the methionine residue at the position 318 are replaced by isoleucine, asparagine, and isoleucine residues, respectively (for these mutants, see U.S. Pat. Nos. 5,661,012 and 6,040,160). Such mutant DNAs can be obtained by site-specific mutagenesis using PCR or the like.

Wide host-range plasmids RSFD80, pCAB1, and pCABD2 are known as plasmids containing a mutant dapA gene encoding a mutant dihydrodipicolinate synthase and a mutant lysC gene encoding a mutant aspartokinase (U.S. Pat. No. 6,040,160). *Escherichia coli* JM109 strain transformed with RSFD80 was named AJ12396 (U.S. Pat. No. 6,040,160), the strain was deposited at the National Institute of Bioscience and Human-Technology, Agency of Industrial Science and Technology, Ministry of International Trade and Industry (currently, independent administrative agency, National Institute of Advanced Industrial Science and Technology, International Patent Organism Depositary) on Oct. 28, 1993 and assigned an accession number of FERM P-13936, and the deposit was then converted to an international deposit under the provisions of Budapest Treaty on Nov. 1, 1994 and assigned an accession number of FERM BP-4859. RSFD80 can be obtained from the AJ12396 strain by a known method.

Examples of L-lysine-producing bacteria and parent strains that can be used to derive such strains also include strains in which the activity of an enzyme that catalyzes a reaction that generates a compound other than L-lysine by branching away from the biosynthetic pathway of L-lysine is decreased or eliminated. Examples of such enzymes can include homoserine dehydrogenase, lysine decarboxylase (U.S. Pat. No. 5,827,698), and the malic enzyme (WO2005/010175). In order to decrease or eliminate the lysine decarboxylase activity, expression of both the cadA gene and ldcC gene coding for lysine decarboxylase can be reduced (International Patent Publication WO2006/038695).

Examples of the strain in which cadA gene and ldcC gene are disrupted include the *Escherichia coli* WC196LC strain (WC196ΔcadAΔldc) (U.S. Pat. No. 5,827,698, U.S. Patent Published Application No. 2006/0160191). The WC196LC strain, which was designated AJ110692, was deposited at National Institute of Advanced Industrial Science and Technology, International Patent Organism Depositary (Central 6, 1-1, Higashi 1-Chome, Tsukuba-shi, Ibaraki-ken, 305-8566, Japan) on Oct. 7, 2008 as an international deposit, and assigned an accession number of FERM BP-11027.

L-Threonine-Producing Bacteria

Examples of L-threonine-producing bacteria and parent strains that can be used to derive such strains can include, but are not limited to, *E. coli* TDH-6/pVIC40 (VKPM B-3996) (U.S. Pat. Nos. 5,175,107, 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and so forth.

The TDH-6 strain is deficient in the thrC gene, as well as having sucrose-utilizing ability, and the ilvA gene thereof has a leaky mutation. This strain also has a mutation in the rhtA gene, which imparts resistance to high concentrations of threonine or homoserine. The B-3996 strain harbors the plasmid pVIC40 obtained by inserting a thrA*BC operon containing a mutant thrA gene into an RSF1010-derived vector. This mutant thrA gene encodes aspartokinase homoserine dehydrogenase I which is substantially desensitized to feedback inhibition by threonine. The B-3996 strain was deposited on Nov. 19, 1987 at the All-Union Scientific Center of Antibiotics (Nagatinskaya Street 3-A, 117105 Moscow, Russia) under the accession number RIA 1867. This strain was also deposited at the Russian National Collection of Industrial Microorganisms (VKPM, 1 Dorozhny proezd., 1 Moscow 117545, Russia) on Apr. 7, 1987 under the accession number VKPM B-3996.

*E. coli* VKPM B-5318 (EP 0593792 B) can also be used as an L-threonine-producing bacterium or a parent strain to derive such a strain. The B-5318 strain is prototrophic with regard to isoleucine, and in this strain, the regulatory region of the threonine operon in the plasmid pVIC40 is replaced with a temperature-sensitive λ-phage C1 repressor and PR promoter. The strain VKPM B-5318 was deposited at the Russian National Collection of Industrial Microorganisms (VKPM) (1 Dorozhny proezd., 1 Moscow 117545, Russia) on May 3, 1990 under the accession number of VKPM B-5318.

The bacterium can be additionally modified to increase expression of one or more of the following genes:
the mutant thrA gene which codes for aspartokinase-homoserine dehydrogenase I resistant to feed back inhibition by threonine;
the thrB gene which codes for homoserine kinase;
the thrC gene which codes for threonine synthase;
the rhtA gene which codes for a putative transmembrane protein;
the asd gene which codes for aspartate-β-semialdehyde dehydrogenase; and
the aspC gene which codes for aspartate aminotransferase (aspartate transaminase).

The thrA gene which encodes aspartokinase-homoserine dehydrogenase I of *Escherichia coli* has been elucidated (nucleotide numbers 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide numbers 2801 to 3733, GenBank accession NC_000913.2, gi: 49175990). The thrB gene is located between the thrA and thrC genes on the chromosome of *E. coli* K-12. The thrC gene which encodes threonine synthase of *Escherichia coli* has been elucidated (nucleotide numbers 3734 to 5020, GenBank accession NC_000913.2, gi: 49175990). The thrC gene is located between the thrB gene and the yaaX open reading frame on the chromosome of *E. coli* K-12. All three of these genes function as a single threonine operon. To increase expression of the threonine operon, the attenuator region which affects the transcription can be removed from the operon (WO2005/049808, WO2003/097839).

The mutant thrA gene which codes for aspartokinase-homoserine dehydrogenase I resistant to feed back inhibition by threonine and the thrB and thrC genes can be obtained as one operon from the well-known plasmid pVIC40 which is present in the threonine-producing *E. coli* strain VKPM B-3996. The plasmid pVIC40 is described in detail in U.S. Pat. No. 5,705,371.

The rhtA gene is located at 18 min on the *E. coli* chromosome close to the glnHPQ operon, which encodes components of the glutamine transport system. The rhtA gene is identical to ORF1 (ybiF gene, nucleotide numbers 764 to 1651, GenBank accession number AAA218541, gi:440181) and is located between the pexB and ompX genes. The unit expressing a protein encoded by the ORF1 has been designated rhtA gene (rht: resistance to homoserine and threonine). It has also been reported that the rhtA23 mutation is an A-for-G substitution at position -1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457; EP 1013765 A).

The asd gene coding for aspartate-β-semialdehyde dehydrogenase of *E. coli* has already been elucidated (nucleotide numbers 3572511 to 3571408, GenBank accession NC_000913.1, gi:16131307), and can be obtained by PCR (refer to White, T. J., Arnheim, N., Erlich, H. A., 1989, Trends Genet, 5:185-189) utilizing primers prepared on the basis of the nucleotide sequence of the gene. The asd genes of other microorganisms can also be obtained in a similar manner.

The aspC gene coding for aspartate aminotransferase of *E. coli* has also already been elucidated (nucleotide numbers 983742 to 984932, GenBank accession NC_000913.1, gi:16128895), and can be obtained by PCR. The aspC genes of other microorganisms can also be obtained in a similar manner.

L-Cysteine-Producing Bacteria

Examples of L-cysteine-producing bacteria and parent strains that can be used to derive such strains can include, but are not limited to, *E. coli* JM15 which is transformed with different cysE alleles encoding feedback inhibition-resistant serine acetyltransferases (U.S. Pat. No. 6,218,168, Russian Patent Application No. 2003121601), *E. coli* W3110 with overexpressed genes encoding proteins suitable for excretion of substances toxic to the cells (U.S. Pat. No. 5,972,663), *E. coli* strains with reduced cysteine desulfhydrase activity (Japanese Patent Laid-open No. 11-155571), *E. coli* W3110 with increased activity of a positive transcriptional regulator for cysteine regulon encoded by the cysB gene (W001/27307A1), and so forth.

L-Leucine-Producing Bacteria

Examples of L-leucine-producing bacteria and parent strains that can be used to derive such strains can include, but are not limited to, *E. coli* strains resistant to leucine (for example, the 57 strain (VKPM B-7386, U.S. Pat. No. 6,124,121)) or *E. coli* strains resistant to an leucine analogue such as β-2-thienylalanine, 3-hydroxyleucine, 4-azaleucine, and 5,5,5-trifluoroleucine (Japanese Patent Publication (Kokoku) No. 62-34397 and Japanese Patent Laid-open No. 8-70879); *E. coli* strains obtained by a gene engineering technique described in WO96/06926; *E. coli* H-9068 (Japanese Patent Laid-open No. 8-70879), and so forth.

The bacterium can be improved by enhancing expression of one or more genes involved in the L-leucine biosynthesis. Examples of such genes include the genes of the leuABCD operon, a typical example of which is a mutant leuA gene coding for isopropyl malate synthase desensitized to feedback inhibition by L-leucine (U.S. Pat. No. 6,403,342). In addition, the bacterium can be improved by increasing expression of one or more genes coding for proteins which excrete L-amino acid from the bacterial cells. Examples of such genes include the b2682 and b2683 genes (ygaZH genes) (EP 1239041 A2).

L-Histidine-Producing Bacteria

Examples of L-histidine-producing bacteria and parent strains that can be used to derive such strains can include, but are not limited to, *E. coli* strain 24 (VKPM B-5945, RU 2003677); *E. coli* strain 80 (VKPM B-7270, RU 2119536); *E. coli* NRRL B-12116 to B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP 1085087); *E. coli* AI80/pFM201 (U.S. Pat. No. 6,258,554), and so forth.

Examples of L-histidine-producing bacteria and parent strains that can be used to derive such strains can also include strains in which expression of one or more genes encoding an L-histidine biosynthetic enzyme is increased. Examples of such genes include ATP phosphoribosyl transferase gene (hisG), phosphoribosyl AMP cyclohydrolase gene (hisI), phosphoribosyl-ATP pyrophosphohydrolase gene (hisI), phosphoribosylformimino-5-aminoimidazole carboxamide ribotide isomerase gene (hisA), amidotransferase gene (hisH), histidinol phosphate aminotransferase gene (hisC), histidinol phosphatase gene (hisB), histidinol dehydrogenase gene (hisD), and so forth.

It is known that the L-histidine biosynthetic enzymes encoded by hisG and hisBHAFI are inhibited by L-histidine, and therefore L-histidine-producing ability can be efficiently enhanced by introducing a mutation which imparts resistance to feedback inhibition into the ATP phosphoribosyl transferase gene (hisG) (Russian Patent Nos. 2003677 and 2119536).

Specific examples of strains having L-histidine-producing ability include *E. coli* FERM-P 5038 and 5048 which are introduced with a vector carrying a DNA encoding an L-histidine biosynthetic enzyme (Japanese Patent Laid-open No. 56-005099), *E. coli* strains introduced with a gene for amino acid transport (EP 1016710 A), *E. coli* 80 strain imparted with sulfaguanidine, DL-1,2,4-triazole-3-alanine, and streptomycin resistance (VKPM B-7270, Russian Patent No. 2119536), and so forth.

L-Glutamic Acid-Producing Bacteria

Examples of L-glutamic acid-producing bacteria and parent strains that can be used to derive such strains can include, but are not limited to, *E. coli* VL334thrC+(EP 1172433), and so forth. *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* K12 strain (VKPM B-7) cells. As a result, an L-isoleucine auxotrophic L-glutamic acid-producing strain VL334thrC+(VKPM B-8961) was obtained.

Examples of L-glutamic acid-producing bacteria and parent strains that can be used to derive such strains can include, but are not limited to, strains in which expression of one or more genes encoding an L-glutamic acid biosynthetic enzyme is increased. Examples of such genes include genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate dehydrogenase (aceEF, 1pdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), glucose phosphate isomerase (pgi), and so forth.

Examples of strains modified to increase expression of the citrate synthetase gene, the phosphoenolpyruvate carboxylase gene, and/or the glutamate dehydrogenase gene include those disclosed in EP 1078989 A, EP 955368 A, and EP 952221A.

Examples of L-glutamic acid-producing bacteria and parent strains that can be used to derive such strains can also include strains in which the activity of an enzyme that catalyzes synthesis of a compound other than L-glutamic acid by branching away from the L-glutamic acid biosynthesis pathway is decreased or eliminated. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), glutamate decarboxylase (gadAB), γ-glutamyl transferase (ggt), γ-glutamylcysteine synthetase (gshA), γ-glutamylputrescine synthetase (ycjK), and so forth. *Escherichia coli* deficient in α-ketoglutarate dehydrogenase activity or having reduced α-ketoglutarate dehydrogenase activity, and methods for obtaining them are described in U.S. Pat. Nos. 5,378,616 and 5,573,945.

Specific examples include the followings:
*E. coli* W3110sucA::Kmr
*E. coli* AJ12624 (FERM BP-3853)
*E. coli* AJ12628 (FERM BP-3854)
*E. coli* AJ12949 (FERM BP-4881)

*E. coli* W3110sucA::Kmr is a strain obtained by disrupting the α-ketoglutarate dehydrogenase gene (hereinafter also referred to as "sucA gene") of *E. coli* W3110. This strain is completely deficient in α-ketoglutarate dehydrogenase.

Other examples of L-glutamic acid-producing bacteria include *Escherichia coli* having resistance to an aspartic acid antimetabolite. Such a strain can also be deficient in α-ketoglutarate dehydrogenase, and examples thereof include, for example, *E. coli* AJ13199 (FERM BP-5807, U.S. Pat. No. 5,908,768), FERM P-12379, which additionally has a lowered L-glutamic acid-decomposing ability (U.S. Pat. No. 5,393,671), AJ13138 (FERM BP-5565, U.S. Pat. No. 6,110,714), and so forth.

Examples of L-glutamic acid-producing bacteria of *Pantoea ananatis* include the *Pantoea ananatis* AJ13355 strain. This strain was isolated from soil in Iwata-shi, Shizuoka-ken, and was identified as being able to proliferate in a medium containing L-glutamic acid and a carbon source at a low pH. The *Pantoea ananatis* AJ13355 strain was deposited at the National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Feb. 19, 1998 and assigned an accession number of FERM P-16644. It was then converted to an international deposit under the provisions of Budapest Treaty on Jan. 11, 1999 and assigned an accession number of FERM BP-6614. This strain was originally identified as *Enterobacter agglomerans* when it was isolated, and deposited as *Enterobacter agglomerans* AJ13355. However, it was recently re-classified into *Pantoea ananatis* on the basis of nucleotide sequencing of 16S rRNA and so forth.

Furthermore, examples of L-glutamic acid-producing bacteria of *Pantoea ananatis* also include *Pantoea* bacteria deficient in α-ketoglutarate dehydrogenase (αKGDH) activity or having reduced αKGDH activity. Examples of such a strain include AJ13356 (U.S. Pat. No. 6,331,419), which was derived by deleting the αKGDH-E1 subunit gene (sucA) in AJ13355, and the SC17sucA strain (U.S. Pat. No. 6,596,517), which is a sucA gene-deficient strain derived from the SC17 strain selected from AJ13355 as a low phlegm-producing mutant strain. The AJ13356 strain was deposited at the National Institute of Bioscience and Human-Technology, Agency of Industrial Science and Technology (currently, the independent administrative agency, National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566)) on Feb. 19, 1998, and assigned an accession number of FERM P-16645. Then, the deposit was converted into an international deposit under the provisions of the Budapest Treaty on Jan. 11, 1999, and assigned an accession number of FERM BP-6616. Although the AJ13355 and AJ13356 strains are deposited at the aforementioned depository as *Enterobacter agglomerans*, they are referred to as *Pantoea* ananatis in this specification. The SC17sucA strain was assigned a private number of AJ417, and deposited at the National Institute of Advanced Industrial Science and Technology, International Patent Organism Depositary on Feb. 26, 2004, under an accession number of FERM BP-08646.

Furthermore, examples of L-glutamic acid-producing bacteria of *Pantoea ananatis* also include SC17sucA/RSFCPG+pSTVCB, AJ13601, NP106, and NA1 strains. The SC17sucA/RSFCPG+pSTVCB strain was obtained by introducing the plasmid RSFCPG containing the citrate synthase gene (gltA), phosphoenolpyruvate carboxylase gene (ppc), and glutamate dehydrogenase gene (gdhA) derived from *Escherichia coli*, and the plasmid pSTVCB containing the citrate synthase gene (gltA) derived from *Brevibacterium lactofermentum*, into the SC17sucA strain. The AJ13601 strain was selected from the SC17sucA/RSFCPG+pSTVCB strain as a strain resistant to a high concentration of L-glutamic acid at a low pH. The NP106 strain was derived from the AJ13601 strain by eliminating the RSFCPG+pSTVCB plasmid as described in Examples. The AJ13601 strain was deposited at the National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566) on Aug. 18, 1999, and assigned an accession number FERM P-17516. Then, the deposit was converted to an international deposit under the provisions of the Budapest Treaty on Jul. 6, 2000, and assigned an accession number FERM BP-7207.

L-Phenylalanine-Producing Bacteria

Examples of L-phenylalanine-producing bacteria and parent strains that can be used to derive such strains can include, but are not limited to, *E. coli* AJ12739 (tyrA::Tn10, tyrR) (VKPM B-8197), *E. coli* HW1089 (ATCC 55371) harboring the mutant pheA34 gene (U.S. Pat. No. 5,354,672), *E. coli* MWEC101-b (KR 8903681), *E. coli* NRRL B-12141, NRRL B-12145, NRRL B-12146, NRRL B-12147 (U.S. Pat. No. 4,407,952), and so forth. As parent strains, *E. coli* K-12 [W3110 (tyrA)/pPHAB] (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ12604 (FERM BP-3579) can also be used (EP 488424 B1). Furthermore, L-phenylalanine-producing bacteria of *Escherichia coli* with an enhanced activity of the protein encoded by the yedA gene or the yddG gene can also be used (U.S. Patent Published Application Nos. 2003/0148473 A1 and 2003/0157667 A1).

L-Tryptophan-Producing Bacteria

Examples of tryptophan-producing bacteria and parent strains that can be used to derive such strains can include, but are not limited to, *E. coli* JP4735/pMU3028 (DSM10122) and JP6015/pMU91 (DSM10123), which have a mutant trpS gene coding for a partially inactivated tryptophanyl-tRNA synthetase (U.S. Pat. No. 5,756,345), *E. coli* SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180,373), *E. coli* AGX17 (pGX44) (NRRL B-12263) and AGX6(pGX50)aroP(NRRL B-12264) deficient in tryptophanase (U.S. Pat. No. 4,371,614), *E. coli* AGX17/pGX50,pACKG4-pps of which phosphoenolpyruvate-producing ability is enhanced (WO97/08333, U.S. Pat. No. 6,319,696), and so forth. L-Tryptophan-producing bacteria of *Escherichia coli* with an enhanced activity of the protein encoded by the yedA gene or the yddG gene can also be used (U.S. Patent Published Application Nos. 2003/0148473 A1 and 2003/0157667 A1).

Examples of L-tryptophan-producing bacteria and parent strains that can be used to derive such strains can also include strains in which one or more activities of the enzymes selected from anthranilate synthase (trpE), phosphoglycerate dehydrogenase (serA), and tryptophan synthase (trpAB) are increased. The anthranilate synthase and phosphoglycerate dehydrogenase both suffer from feedback inhibition by L-tryptophan and L-serine, and therefore a mutation desensitizing them to the feedback inhibition can be introduced into these enzymes. Specific examples of strains having such a mutation include *E. coli* SV164 which harbors desensitized anthranilate synthase and a transformant strain obtained by introducing the plasmid pGH5 (WO94/08031), which contains a mutant serA gene encoding feedback inhibition-desensitized phosphoglycerate dehydrogenase, into the *E. coli* SV164.

Examples of L-tryptophan-producing bacteria and parent strains that can be used to derive such strains can also include strains into which the tryptophan operon containing a gene encoding inhibition-desensitized anthranilate synthase is introduced (Japanese Patent Laid-open Nos. 57-71397, 62-244382, U.S. Pat. No. 4,371,614). Moreover, L-tryptophan-producing ability can be imparted by increasing expression of a gene encoding tryptophan synthase (trpBA) in the tryptophan operon. The tryptophan synthase includes α and β subunits encoded by the trpA and trpB genes, respectively. In addition, L-tryptophan-producing ability can also be improved by increasing expression of an operon (ace operon) of genes of maleate synthase (aceB), isocitrate lyase (aceA), and isocitrate dehydrogenase kinase/phosphatase (aceK) (WO2005/103275).

L-Proline-Producing Bacteria

Examples of L-proline-producing bacteria and parent strains that can be used to derive such strains can include, but are not limited to, *E. coli* 702ilvA (VKPM B-8012), which is deficient in the ilvA gene and is able to produce L-proline (EP 1172433), and so forth.

The bacterium can be improved by increasing expression of one or more genes involved in the L-proline biosynthesis. Examples of a gene for L-proline-producing bacteria include the proB gene coding for glutamate kinase desensitized to feedback inhibition by L-proline (DE 3127361). In addition, the bacterium can be improved by increasing expression of one or more genes coding for proteins excreting L-amino acid from the bacterial cells. Examples of such genes include the b2682 and b2683 genes (ygaZH genes) (EP 1239041 A2).

Examples of *Escherichia coli* having L-proline-producing ability include the following *E. coli* strains: NRRL B-12403 and NRRL B-12404 (British Patent No. 2075056), VKPM B-8012 (Russian Patent Application No. 2000124295), plasmid mutants described in German Patent No. 3127361, plasmid mutants described by Bloom F. R. et al. (The 15th Miami winter symposium, 1983, p. 34), and so forth.

L-Arginine-Producing Bacteria

Examples of L-arginine-producing bacteria and parent strains that can be used to derive such strains can include, but are not limited to, *E. coli* strain 237 (VKPM B-7925) (U.S. Patent Published Application No. 2002/058315A1) and derivative strains thereof harboring a mutant N-acetylglutamate synthase (Russian Patent Application No. 2001112869), *E. coli* strain 382 (VKPM B-7926) (EP 1170358 A1), an arginine-producing strain into which argA gene encoding N-acetylglutamate synthetase is introduced (EP 1170361 A1), and so forth.

Examples of L-arginine-producing bacteria and parent strains that can be used to derive such strains can also include strains in which expression of one or more genes encoding an L-arginine biosynthetic enzyme is increased. Examples of such genes include N-acetylglutamyl phosphate reductase gene (argC), ornithine acetyl transferase gene (argJ), N-acetylglutamate kinase gene (argB), acetylornithine transaminase gene (argD), ornithine carbamoyl transferase gene (argF), argininosuccinic acid synthetase gene (argG), argininosuccinic acid lyase gene (argH), and carbamoyl phosphate synthetase gene (carAB).

L-Valine-producing bacteria

Example of L-valine-producing bacteria and parent strains that can be used to derive such strains can include, but are not limited to, strains which have been modified to overexpress the ilvGMEDA operon (U.S. Pat. No. 5,998,178). It is desirable to remove the region required for attenuation in the ilvGMEDA operon so that expression of the operon is not attenuated by produced L-valine. Furthermore, the ilvA gene in the operon can be disrupted so that threonine deaminase activity is decreased.

Examples of L-valine-producing bacteria and parent strains that can be used to derive such strains can also include mutant strains having a mutation in amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 was deposited at the Russian National Collection of Industrial Microorganisms (VKPM) (1 Dorozhny Proezd, 1 Moscow 117545, Russia) on Jun. 24, 1988 under the accession number of VKPM B-4411.

Furthermore, mutant strains requiring lipoic acid for growth and/or lacking H+-ATPase (WO96/06926) can also be used as the parent strains.

L-Isoleucine-Producing Bacteria

Examples of L-isoleucine-producing bacteria and parent strains that can be used to derive such strains can include, but are not limited to, mutant strains having resistance to 6-dimethylaminopurine (Japanese Patent Laid-open No. 5-304969), mutant strains having resistance to an isoleucine analogue such as thiaisoleucine and isoleucine hydroxamate, and such mutant strains further having resistance to DL-ethionine and/or arginine hydroxamate (Japanese Patent Laid-open No. 5-130882). In addition, recombinant strains transformed with genes encoding proteins involved in the L-isoleucine biosynthesis, such as threonine deaminase and acetohydroxy acid synthase, can also be used as the parent strains (Japanese Patent Laid-open No. 2-458, FR 0356739, and U.S. Pat. No. 5,998,178).

L-Asparagine-Producing Bacteria

L-Asparagine is produced by transferring an amino group to aspartic acid
(Boehlein, S. K., Richards, N. G. J., & Schuster, S. M. (1994a), J. Biol. Chem., 269, 7450-7457). Therefore, examples of L-asparagine-producing bacteria of *Escherichia coli* include L-aspartic acid-producing *Escherichia coli* strains in which asparagine synthetase is enhanced.

The ability of the bacterium to utilize a fatty acid or an alcohol such as glycerol can be enhanced.

Fatty acid-utilizing ability can be enhanced by, for example, attenuating expression of the fadR gene or deleting this gene, or enhancing expression of a gene involved in the fatty acid utilization, such as fadI, fadJ, fadL, fadE, fadD, fadB, or fadA gene (WO2009/142286).

The glycerol-utilizing ability can be enhanced by attenuating expression of the glpR gene (European Patent No. 1715056), enhancing expression of a glycerol metabolism gene such as glpA, glpB, glpC, glpD, glpE, glpF, glpG, glpK, glpQ, glpT, glpX, tpiA, gldA, dhaK, dhaL, dhaM, dhaR, fsa and talC genes (EP 1715055 A), or enhancing expression of the glycerol dehydrogenase gene (gldA), dihydroxyacetone kinase gene (dhaKLM, dak) and fructose-6-phosphate aldolase gene (fsaB) (WO2008/102861).

The bacterium can have an ethanol-utilizing ability. Such a strain can be a bacterium inherently having ethanol-utilizing ability, a recombinant strain to which ethanol-utilizing ability is imparted, or a mutant strain of which ethanol-utilizing ability is increased.

As for *Escherichia coli*, as an enzyme anaerobically generating ethanol, presence of AdhE, which has activities of acetaldehyde dehydrogenase and alcohol dehydrogenase reversibly catalyzing the reactions mentioned below, is known. The sequence of the adhE gene coding for AdhE of *Escherichia coli* is disclosed in WO2009/031565 and U.S. Patent Published Application No. 2009/068712.

Acetyl-CoA+NADH+H+->acetaldehyde+NAD++CoA

Acetaldehyde+NADH+H+->ethanol+NAD+

When ethanol is used as the carbon source, a bacterium can be used that can aerobically utilize ethanol. Although *Escherichia coli* usually cannot utilize ethanol under an aerobic condition, a strain modified so as to be able to aerobically utilize ethanol can be used. Examples of the method for modifying a bacterium that inherently cannot aerobically utilize ethanol so as to be able to aerobically utilize ethanol include making the bacterium harbor the adhE gene modified so as to be expressed under the control of a non-native promoter that functions under an aerobic condition, and making the bacterium harbor the adhE gene having a mutation that enables aerobic utilization of ethanol in the coding region (Clark D. P., and Cronan, J. E. Jr., 1980, J. Bacteriol., 144: 179-184; Membrillo-Hernandez, J. et al., 2000, J. Biol. Chem., 275:33869-33875). Furthermore, this mutant adhE gene can be expressed under control of a non-native promoter that functions under an aerobic condition.

In *Escherichia coli*, if the promoter located upstream of the gene coding for alcohol dehydrogenase is replaced with a promoter that functions aerobically, alcohol dehydrogenase is expressed under an aerobic condition, and *Escherichia coli* becomes able to aerobically utilize ethanol (WO2008/010565). As the non-native promoter that functions under an aerobic condition, an arbitrary promoter that can express the adhE gene at a level exceeding a certain specific level under an aerobic condition can be used. The aerobic condition can be a condition typically used for culture of bacteria in which oxygen is supplied by a method such as shaking, aeration, stifling, or the like. Specifically, an arbitrary promoter that is known to express a gene under an aerobic condition can be used. For example, promoters of genes involved in the glycolysis, pentose phosphate pathway, TCA cycle, amino acid biosynthesis pathways, and so forth can be used. Furthermore, the Ptac promoter, lac promoter, trp promoter, trc promoter, and PR and PL promoters of λ phage are all known as strong promoters that function under an aerobic condition.

As a mutant AdhE having such a mutation as mentioned above, specifically, the mutant AdhE of *Escherichia coli* in which the glutamic acid residue at position 568 is replaced with an amino acid residue other than glutamic acid and aspartic acid residues, e.g. lysine residue, is known (Glu568Lys, E568K, WO2008/010565).

The aforementioned mutant AdhE can further include the following additional mutation(s).

A) Replacement of the glutamic acid residue at position 560 with another amino acid residue such as lysine residue, B) Replacement of the phenylalanine residue at position 566 with another amino acid residue such as valine residue, C) Replacement of the glutamic acid residue at position 22, methionine residue at position 236, tyrosine residue at position 461, isoleucine residue at position 544, and alanine residue at position 786, with other amino acid residues such as glycine residue, valine residue, cysteine residue, serine residue, and valine residue, respectively, or D) a combination of the aforementioned mutations.

The expression "a bacterium can aerobically utilize ethanol" means that the bacterium can grow in a minimum liquid medium or solid medium containing ethanol as the sole carbon source under an aerobic condition. The "aerobic condition" can mean that a bacterium is cultured and oxygen is supplied to the culture by a method such as shaking, aeration, stirring, or the like, as mentioned above. The expression "a bacterium can aerobically utilize ethanol" can also mean that, as for the level of the AdhE protein, the activity of alcohol dehydrogenase in a cell-free extract measured according to the method of Clark and Cronan (J. Bacteriol., 1980, 141, 177-183) is 1.5 units or higher, 5 units or higher, or 10 units or higher, per mg of the protein.

The bacterium can be modified so that the activity of pyruvate synthase or pyruvate:$NADP^+$ oxidoreductase is increased. The expression that "the activity of pyruvate synthase or pyruvate:$NADP^+$oxidoreductase is increased" can mean that the activity of pyruvate synthase or pyruvate:$NADP^+$oxidoreductase is increased as compared with an unmodified strain such as a wild strain or the parent strain. In addition, the expression "the activity of pyruvate synthase or pyruvate:$NADP^+$oxidoreductase is increased" include a case where the pyruvate synthase or pyruvate:$NADP^+$oxidoreductase activity is imparted to a microorganism that does not inherently have the pyruvate synthase or pyruvate:$NADP^+$ oxidoreductase activity.

The "pyruvate synthase" can mean an enzyme reversibly catalyzing the following reaction, which generates pyruvic acid from acetyl-CoA and CO2, in the presence of an electron donor such as ferredoxin or flavodoxin (EC 1.2.7.1). Pyruvate synthase can be abbreviated as PS, and can be designated pyruvate oxidoreductase, pyruvate ferredoxin oxidoreductase, or pyruvate flavodoxin oxidoreductase. As the electron donor, ferredoxin or flavodoxin can be used.

Reduced ferredoxin+acetyl-CoA+CO2->oxidized ferredoxin+pyruvic acid+CoA

Pyruvate synthase activity enhancement can be confirmed by preparing crude enzyme solutions from the microorganism before the enhancement and the microorganism after the enhancement, and comparing the pyruvate synthase activities. The activity of pyruvate synthase can be measured by, for example, the method of Yoon et al. (Yoon, K. S. et al., 1997, Arch. Microbiol. 167:275-279). For example, the measurement can be attained by adding pyruvic acid to a reaction solution containing oxidized methylviologen as an electron acceptor, CoA, and a crude enzyme solution, and spectroscopically measuring the amount of reduced methylviologen, which increases due to the decarboxylation reaction of pyruvic acid. One unit (U) of the enzymatic activity is defined as an activity of reducing 1 µmol of methylviologen per 1 minute. When the parent strain has the pyruvate synthase activity, the activity can be increased, for example, 1.5 times or more, 2 times or more, or 3 times or more, as compared with that of the parent strain. When the parent strain does not have the pyruvate synthase activity, although it is sufficient that pyruvate synthase is produced due to the introduction of the pyruvate synthase gene, the activity can be enhanced to such an extent that the enzymatic activity can be measured, and the activity can be 0.001 U/mg (cell protein) or higher, 0.005 U/mg or higher, or 0.01 U/mg or higher. The pyruvate synthase is sensitive to oxygen, and expression of the activity and measurement of the activity can often be difficult (Buckel, W. and Golding, B. T., 2006, Ann. Rev. of Microbiol., 60:27-49). Therefore, when the enzymatic activity is measured, the enzymatic reaction can be performed while reducing the oxygen concentration in the reaction vessel.

As the gene encoding pyruvate synthase, it is possible to use pyruvate synthase genes of bacteria having the reductive TCA cycle such as *Chlorobium tepidum* and *Hydrogenobacter thermophilus*. Moreover, it is also possible to use pyruvate synthase genes of bacteria belonging to the family Enterobacteriaceae including *Escherichia coli*. Furthermore, as the gene encoding pyruvate synthase, pyruvate synthase genes of autotrophic methanogens such as *Methanococcus maripaludis*, *Methanocaldococcus jannaschii*, and *Methanothermobacter thermautotrophicus* can be used.

<2-2> Method for Obtaining a Bacterium Belonging to the Family Enterobacteriaceae that Harbors a Mutant RpsA Protein The bacterium can be obtained by modifying such a bacterium as mentioned above belonging to the family Enterobacteriaceae and having an L-amino acid-producing ability so that it harbors an RpsA protein wherein the aspartic acid residue at position 210 is replaced with another amino acid residue, which also be referred to as the "mutant RpsA protein". The bacterium can also be obtained by imparting an L-amino acid-producing ability to a bacterium that has been modified so that it harbors the mutant RpsA protein.

In order to make a bacterium belonging to the family Enterobacteriaceae harbor a mutant RpsA protein, a mutant rpsA gene coding for a mutant RpsA protein can be introduced into a bacterium belonging to the family Enterobacteriaceae, or a mutation can be introduced into a wild-type rpsA gene on the chromosome so that the aspartic acid residue at position 210 of the RpsA protein is replaced with another amino acid residue.

In order to introduce a mutant rpsA gene into a bacterium belonging to the family Enterobacteriaceae, for example, the bacterium belonging to the family Enterobacteriaceae can be transformed with a vector containing the mutant rpsA gene. Alternatively, a mutant rpsA gene can be transferred to the chromosome of a bacterium belonging to the family Enterobacteriaceae by using repetitive DNA, inverted repeats inserted at the ends of a transposable element, transposon, or the like.

Examples of the aforementioned vector include plasmid vectors such as pUC19, pUC18, pHSG299, pHSG399, pHSG398, RSF1010, pBR322, pACYC184, pMW118, and pMW219, and phage vectors such as λ1059, λBF101 and M13 mp 9. Examples of the transposon include Mu, Tn10, Tn5 and so forth.

The expression control sequence such as a promoter for expressing a mutant rpsA gene can be inherent to the rpsA gene, or can be a promoter derived from another gene or an artificial promoter. Examples of such promoters include lac promoter, trp promoter, trc promoter, tac promoter, PR promoter and PL promoter of λ phage, PL-tac promoter, tet promoter, and so forth.

The bacterium can, but does not have to harbor the wild-type RpsA protein. Such a bacterium can be obtained by modifying the rpsA gene on the chromosome so that the wild-type RpsA gene is not expressed, for example, by disrupting the rpsA gene. Alternatively, by replacing the rpsA gene on the chromosome with a mutant rpsA gene, a bacterium without the wild-type RpsA protein, but harboring the mutant RpsA protein can be obtained. Examples of the method for such gene substitution include, for example, methods using a linear DNA such as the method called "Red-driven integration" (Datsenko, K. A., and Wanner, B. L., 2000, Proc. Natl. Acad. Sci. USA, 97:6640-6645) and the method of utilizing the Red driven integration in combination with an excision system derived from λ phage (Cho, E. H., Gumport, R. I., Gardner, J. F., 2002, J. Bacteriol., 184:5200-5203) (refer to WO2005/010175), methods using a plasmid containing a temperature sensitive replication origin, methods using a plasmid capable of conjugative transfer, methods utilizing a suicide vector without a replication origin in a host (U.S. Pat. No. 6,303,383, Japanese Patent Laid-open No. 05-007491), and so forth. Furthermore, a mutant rpsA gene can also be introduced into an arbitrary bacterial strain belonging to the family Enterobacteriaceae from a bacterium harboring the mutant rpsA gene by P1 transduction, homologous recombination, λ-Red method, or the like.

Although it is sufficient that the bacterium harbors a gene coding for the aforementioned RpsA protein on the chromosome, the bacterium can contain two copies, or three or more copies of the gene in the cell. Moreover, because it can be difficult to disrupt or delete the rpsA gene, a mutant gene can be introduced once into the cell, and substituted for the wild-type rpsA gene.

<3> Method for Producing L-Amino Acid

An L-amino acid can be produced by culturing the bacterium in a medium containing a carbon source such as a fatty acid and an alcohol, and an L-amino acid can be collected from the medium. As the carbon source, either a fatty acid or an alcohol can be used, or these both can be used.

The term "fatty acid" can refer to a monovalent carboxylic acid of long chain hydrocarbon represented by the general formula $C_nH_mCOOH$ (n+1 and m+1 represent the number of carbon atoms and the number of hydrogen atoms contained in the fatty acid, respectively). In general, a fatty acid having 12 or more carbon atoms is often referred to as a long chain fatty acid. There are a variety of fatty acids with varying number of carbons and varying degree of unsaturation. It is also known that fatty acids are constituents of fats and oils, and the compositions of fatty acids vary according to the types of fats and oils. Myristic acid ($C_{13}H_{27}COOH$) is a saturated fatty acid having 14 carbon atoms and is contained in coconut oil and palm oil. Palmitic acid ($C_{15}H_{31}COOH$) is a saturated fatty acid having 16 carbon atoms and is abundantly contained in vegetable fats and oils in general. Stearic acid ($C_{17}H_{35}COOH$) is a saturated fatty acid having 18 carbon atoms and is abundantly contained in animal fats and vegetable oils. Oleic acid ($C_{17}H_{33}COOH$) is a monovalent unsaturated fatty acid having 18 carbon atoms and is abundantly contained in animal fats or vegetable oils. Linoleic acid ($C_{17}H_{31}COOH$) is a multivalent unsaturated fatty acid having 18 carbon atoms and two double bonds of cis-configuration at positions 9 and 12. As the fatty acid, a mixture of the aforementioned long chain fatty acids can also be used. When a mixture of fatty acids is used as a carbon source, any ratio of the fatty acids can be used, so long as the ratio is at a concentration at which the chosen bacterium can utilize the mixture as the carbon source. A mixture of fatty acids obtained by removing glycerol from a hydrolysate of fat or oil can also be used.

Examples of the alcohol can include glycerol, ethanol, butanol, propanol, aliphatic alcohols, aromatic alcohols, and so forth.

The term "glycerol" can refer to a substance having the nomenclature propane-1,2,3-triol. Glycerol can be pure glycerol, or crude glycerol. Crude glycerol can refer to industrially produced glycerol that can contain impurities. Crude glycerol is industrially produced by contacting fat or oil with water at a high temperature and under high pressure thereby to hydrolyze it, or by the esterification reaction for biodiesel fuel production. Biodiesel fuel can refer to fatty acid methyl esters produced from fat or oil and methanol by a transesterification, and crude glycerol is produced as a by-product of this reaction (refer to Fukuda, H., Kondo, A., and Noda, H., 2001, J. Biosci. Bioeng., 92, 405-416). In the biodiesel fuel production process, in many cases, the alkaline catalyst method is used for the transesterification and acids are added for neutralization, and hence, crude glycerol with a purity of about 70 to 95% by weight containing water and impurities is produced. Crude glycerol produced in the biodiesel fuel production contains residual methanol, and salts of alkali such as NaOH as a catalyst and an acid such as $H2SO4$ used for neutralizing the alkali as impurities, in addition to water. Although it depends on the manufacturers and production methods, the content of such salts and methanol can reach several percent. The crude glycerol can contain ions derived from the alkali and the acid used for the neutralization of the alkali, such as sodium ions, potassium ions, chloride ions, and sulfate ions, in an amount of 2 to 7%, 3 to 6%, or 4 to 5.8%, based on the weight of the crude glycerol. Although methanol may not be present as an impurity, it is can be present in an amount of 0.01% or less.

The crude glycerol can further contain trace amounts of metals, organic acids, phosphorus, fatty acids, and so forth. Examples of the organic acids include formic acid, acetic acid, and so forth, and although they may not be present as impurities, they are can be present in an amount of 0.01% or less. As the trace amounts of metals present in the crude glycerol, trace metals required for growth of microorganisms can be present, and examples thereof include, for example, magnesium, iron, calcium, manganese, copper, zinc, and so forth. Magnesium, iron and calcium can be present in an amount of from 0.00001 to 0.1%, 0.0005 to 0.1%, 0.004 to 0.05%, or 0.007 to 0.01%, in terms of the total amount based on the weight of the crude glycerol. Manganese, copper and zinc can be present in an amount of from 0.000005 to 0.01%, 0.000007 to 0.005%, or 0.00001 to 0.001%, in terms of the total amount.

It is sufficient that the purity of the crude glycerol is 10% or higher, and it can be 50% or higher, 70% or higher, or 80% or higher. As long as the amounts of the impurities present are within the aforementioned range, the purity of the glycerol can be 90% or higher.

When crude glycerol is used, the crude glycerol can be added to the medium according to the glycerol purity thereof so that the above glycerol concentration is obtained. Both glycerol and crude glycerol can also be added to the medium.

The carbon source can be a hydrolysate of fat or oil. Hydrolysate of fat or oil is generally obtained as a mixture containing a fatty acid and glycerol. So long as a fatty acid and/or glycerol is present, a medium containing a hydrolysate of fat or oil is a "medium containing a fatty acid or an alcohol".

Fats and oils are esters of a fatty acid and glycerol, and they are also called triglycerides. As the fats and oils, any kinds of fats and oils including oils, which refer to those in a liquid state at ordinary temperature, and fats, which refer to those in a solid state at ordinary temperature, can be used, so long as hydrolysable fat or oil is chosen. Furthermore, any type of animal fats and oils (including fish fats and oils) and vegetable fats and oils can be used, and they can be used independently or as a combination of two or more kinds of them. Fat or oil used as a raw material can be pure fat or oil, or a mixture containing fat or oil and substances other than the fat or oil. In the case of vegetable fats and oils, examples thereof include, for example, a plant extract containing fat or oil and a fractionation product thereof.

Examples of animal fats and oils can include butter, lard, beef tallow, mutton tallow, whale oil, sardine oil, herring oil, and so forth. Examples of vegetable fats and oils can include, but not limited to, palm oil, olive oil, rapeseed oil, soybean oil, rice bran oil, walnut oil, sesame oil, peanut oil, and so forth. Palm oil is oil that can be obtained from fruits of oil palm, and has come to be widely used as biodiesel fuel in recent years, and the production amount thereof is increasing. Oil palm is a generic name for the plants classified into the genus *Elaeis* of the family Palmae. Crude palm oil generally refers to unrefined palm oil produced at oil mills, and such palm oil is traded as crude palm oil. Microalgae that accumulate fat or oil are also known (Chisti, Y., Biotechnol. Adv., 2007, 25: 294-306), and the fat or oil can also be extracted from the alga cells. Although the alga cells also contains organic substances other than the fat or oil such as saccharides, proteins, or amino acids, a mixture containing these substances can be hydrolyzed and used as the carbon source.

Fats and oils hydrolyzable into fatty acid(s) that can be utilized by the chosen bacterium, and containing a higher content of the fatty acid(s) can be used. Examples of long chain fatty acid species that can be utilized by bacteria having an L-amino acid-producing ability include lauric acid, myristic acid, palmitic acid, stearic acid, oleic acid, and so forth.

A hydrolysate of fat or oil can refer to a substance obtained by chemically or enzymatically hydrolyzing the aforementioned fat or oil, and can refer to a mixture of a fatty acid and glycerol. As an industrial hydrolysis method, a continuous high temperature hydrolysis method in which fat or oil is brought into contact with water by countercurrent contacting at a high temperature (250 to 260° C.) under a high pressure (5 to 6 MPa) is commonly performed. A reaction performed at low temperature (about 30° C.) by using an enzyme is also industrially used (Jaeger, K. E. et al., 1994, FEMS Microbial. Rev., 15:29-63). As the aforementioned enzyme, a lipase, which is an enzyme that catalyzes a hydrolysis reaction of fats and oils, can be used. Lipases are industrially important enzymes and used for various industrial applications (Hasan, F. et al., 2006, Enzyme and Microbiol. Technol., 39:235-251). A hydrolysate of fat or oil is a mixture of a fatty acid and glycerol, and it is known that weight ratio of glycerol to the fatty acid contained in a hydrolysate of common fat or oil such as palm oil is about 10%. The hydrolysate of fat or oil is not particularly limited so long as the hydrolysate contains a fatty acid and/or glycerol. For example, a hydrolysate of fat or oil can be used as it is, a hydrolysate of fat or oil from which a portion of fatty acid and glycerol is removed can also be used, or a hydrolysate of fat or oil to which a fatty acid or glycerol is added can also be used. In such a case, the weight ratio of glycerol to the fatty acid can be 5 to 20:100, or 7.5 to 15:100.

The concentration of fatty acid can be measured by gas chromatography (Hashimoto, K. et al., 1996, Biosci. Biotechnol. Biochem., 70:22-30) or HPLC (Lin, J. T. et al., 1998, J. Chromatogr. A., 808:43-49).

The fatty acid to be added to the medium, or fatty acid contained in a hydrolysate of fat or oil to be added to the medium, is desirably used as an alkali metal salt of sodium, potassium, or the like, which can be micellized in water. However, the solubility of a sodium salt or potassium salt of fatty acid may not be sufficient for use as a fermentation raw material. Therefore, in order that a fatty acid can be more efficiently utilized by the bacterium having an L-amino acid-producing ability, a step for promoting homogenization, for example, performing emulsification can be used. For example, as the emulsification method, an emulsification enhancer or a surfactant can be added. Examples of the emulsification enhancer can include phospholipids and sterols. Examples of the surfactant include, as nonionic surfactants, poly(oxyethylene) sorbitan fatty acid esters such as poly(oxyethylene) sorbitan monooleic acid ester (Tween 80); alkyl glucosides such as n-octyl β-D-glucoside; sucrose fatty acid esters such as sucrose stearate; polyglycerin fatty acid esters such as polyglycerin stearic acid ester; and so forth. Examples of the surfactant include, as ampholytic surfactants, N,N-dimethyl-N-dodecylglycine betaine, which is an alkylbetaine, and so forth. Besides these, surfactants generally used in the field of biology such as Triton X-100, polyoxyethylene (20) cetyl ether (Brij-58), and nonylphenol ethoxylate (Tergitol NP-40) can be used.

Furthermore, promoting emulsification or homogenization of fatty acid can also be effective. Any method that promotes emulsification or homogenization of fatty acid can be used. Specific examples of methods can include homogenizer treatments, homomixer treatments, ultrasonication, high pressure treatments, high temperature treatments, and so forth. Homogenizer treatments, ultrasonication, and combinations thereof are particular methods.

A combination of the aforementioned treatments with a surfactant and homogenizer treatment and/or ultrasonication can be used. These treatments can be carried out under an alkaline condition since fatty acids are more stable. As the alkaline condition, pH not lower than 9 can be used, and pH not lower than 10 is a particular example.

The fatty acid or alcohol can be present in the medium in any amount so long as the chosen bacterium can utilize it. However, when the fatty acid or alcohol is added to the medium as the sole carbon source, it can be present at a concentration of 10 w/v % or lower, 5 w/v % or lower, or 2 w/v % or lower. When the fatty acid or alcohol is added to the medium as the sole carbon source, it can be added at a concentration of 0.2 w/v % or higher, 0.5 w/v % or higher, or 1.0 w/v % or higher.

Furthermore, the medium can contain other carbon sources in addition to the fatty acid or alcohol. Other carbon sources can include saccharides such as glucose, fructose, sucrose, lactose, galactose, blackstrap molasses, and starch hydrolysate, and organic acids such as fumaric acid, citric acid, and succinic acid. These other carbon sources can be used in such amount that the ratio of the fatty acid or alcohol in the carbon source is 10% by weight or more, 30% by weight or more, or 50% by weight or more.

When a fatty acid or glycerol is added to a feed medium as the sole carbon source, it can be present in the feed medium at such a concentration that the concentration in the medium after feeding is 5 w/v % or lower, 2 w/v % or lower, or 1 w/v % or lower. When a fatty acid or glycerol is added to a feed medium as the sole carbon source, the amount can be controlled to be 0.01 w/v % or higher, 0.02 w/v % or higher, or 0.05 w/v % or higher.

A fatty acid or an alcohol can be present at a certain constant concentration throughout the culture process, it can be added only to the feed medium or the starting medium, or if other carbon sources are contained at a sufficient level, there can be a period where a fatty acid and/or an alcohol temporarily runs short. The term "temporarily" can mean that, for example, a fatty acid and/or an alcohol can run short for a period corresponding to 10%, 20%, or 30% at most, of the entire fermentation period. The concentration of a fatty acid and/or an alcohol can even temporarily be 0, and such a situation is included in the scope of the expression "to culture in a medium containing a fatty acid or an alcohol as a carbon source", so long as there is a period during the culture when the medium contains a fatty acid or an alcohol.

Components other than the carbon source can be added to the medium, such as a nitrogen source, inorganic ions, and other organic components, as required. As the nitrogen source, ammonia; ammonium salts such as ammonium sulfate, ammonium carbonate, ammonium chloride, ammonium phosphate, ammonium acetate, and urea; nitrates; or so forth can be used. Ammonia gas and aqueous ammonia used for pH adjustment can also be used as the nitrogen source. Furthermore, peptone, yeast extract, meat extract, malt extract, corn steep liquor, soybean hydrolysate, and so forth can also be used as the nitrogen source. The medium can contain only one kind of these nitrogen sources, or two or more kinds of these nitrogen sources.

The medium can contain a phosphoric acid source and a sulfur source in addition to the carbon source and the nitrogen source. As the phosphoric acid source, potassium dihydrogenphosphate, dipotassium hydrogenphosphate, phosphoric acid polymers such as pyrophosphoric acid, and so forth can be used. Although the sulfur source can be any substance containing sulfur atoms, sulfuric acid salts such as sulfates, thiosulfates, and sulfites; and sulfur-containing amino acids such as cysteine, cystine, and glutathione are examples, and ammonium sulfate particular examples.

Furthermore, the medium can contain a growth-promoting factor (nutrient having a growth-promoting effect) in addition to the aforementioned components. As the growth-promoting factor, trace metals, amino acids, vitamins, nucleic acids, as well as peptone, casamino acid, yeast extract, soybean protein degradation product, and so forth containing the foregoing substances can be used. Examples of the trace metals include iron, manganese, magnesium, calcium and so forth. Examples of the vitamins include vitamin B1, vitamin B2, vitamin B6, nicotinic acid, nicotinamide, vitamin B12 and so forth.

Furthermore, when an auxotrophic mutant that requires an amino acid or the like for growth thereof is used, it is preferable to supplement the medium with the required nutrient. In particular, because the L-lysine biosynthetic pathway is enhanced and L-lysine degrading ability is attenuated in many of L-lysine-producing bacteria as described later, one or more kinds of substances selected from L-threonine, L-homoserine, L-isoleucine, and L-methionine can be added.

The components mentioned above such as nitrogen sources, phosphoric acid sources, sulfur sources, growth-promoting factors, and amino acids can be contained in the starting medium, or can be contained in the feed medium. The starting medium and the feed medium can contain the same components or different components. Furthermore, the starting medium and the feed medium can have the same concentration or different concentrations for each component. Furthermore, when the feed medium is fed at multiple steps, the compositions of the feed media fed at the steps can be the same or different.

The culture can be performed as an aeration culture at a fermentation temperature of 20 to 45° C., or 33 to 42° C. The oxygen concentration is controlled to be about 5 to 50%, or about 10%. Furthermore, the aeration culture can be performed while controlling pH to be 5 to 9. If pH of the medium is lowered during the culture, the medium can be neutralized by, for example, adding calcium carbonate or an alkaline such as ammonia gas and aqueous ammonia. If culture is performed under such conditions as described above for about 10 to 120 hours, a marked amount of L-amino acid can be accumulated in the culture medium.

In order to keep the accumulation of L-amino acid at a certain level or higher, the culture of the bacterium can be carried out as separate seed culture and main culture. The seed culture can be carried out as shake culture or batch culture using a flask or the like, and the main culture can be carried out as fed-batch culture or continuous culture. Both the seed culture and main culture can be carried out as batch culture.

When fed-batch culture or continuous culture is performed, the feed medium can be intermittently fed so that feeding of a fatty acid or alcohol, or other carbon sources is temporarily stopped. For example, the supply of the feed medium can be stopped so that duration per feeding is 30% or less, 20% or less, or 10% or less, of the total period for the feeding of multiple times. When the feed medium is intermittently added, the feed medium can be initially added over a certain period of time, and the second and following additions can be controlled so that they are started when the pH or dissolved oxygen concentration is elevated due to carbon source depletion in the fermentation medium, during a period when nothing is added prior to a period when medium is added, is detected by a computer, and thus the substrate concentration in the culture tank is always automatically maintained at a low level (U.S. Pat. No. 5,912,113).

The feed medium used for the fed-batch culture can be a medium containing a fatty acid or an alcohol, another carbon source, and a nutrient having growth-promoting effect (growth-promoting factor), and fatty acid concentration in the fermentation medium can be controlled to be a certain level or lower.

The other carbon source added to the feed medium can be glucose, sucrose and/or fructose. As the growth-promoting factor, nitrogen source, phosphoric acid, amino acids and so forth can be used. As the nitrogen source, ammonia; ammonium salts such as ammonium sulfate, ammonium carbonate, ammonium chloride, ammonium phosphate, ammonium acetate, and urea; nitrates; and so forth can be used. Furthermore, as the phosphoric acid source, potassium dihydrogenphosphate and dipotassium hydrogenphosphate can be used. As for the amino acids, when an auxotrophic mutant strain is used, a required nutrient can be supplemented. Furthermore, the feed medium can consist of one type of medium, or a mixture of two or more types of media. When two or more types of feed media are used, the media can be mixed and fed by using one feed tube, or the media can be fed by using two or more feed tubes.

When the continuous culture method is used, the medium can be extracted and fed simultaneously, or after a part of the medium is extracted, the medium can then be fed. Furthermore, a continuous culture method can be used including a step of recycling cells in which the culture medium containing an L-amino acid and bacterial cells is extracted, and only the cells are returned to the fermentation tank (refer to French Patent No. 2669935). As the method for continuously or intermittently feeding a nutrient source, the same method as used in the fed-batch culture is used.

The continuous culture method including recycling cells can include steps of intermittently or continuously extracting the fermentation medium when an intended amino acid concentration is obtained, collecting only the L-amino acid from the medium, and recycling the filtration residue containing the cells into the fermentation tank, and such a method can be performed with reference to, for example, French Patent No. 2669935.

When the culture medium is intermittently extracted, a part of the L-amino acid can be extracted when the L-amino acid concentration reaches a predetermined level, and fresh medium can be fed to continue the culture. Furthermore, the medium can be added in such a volume that the final volume of the medium becomes equal to the volume of the culture medium before the extraction. The term "equal volume" can mean a volume corresponding to about 93 to 107% of the volume of the medium before the extraction.

When the culture medium is continuously extracted, the extraction can be started at the same time as or after the feeding of the nutrient medium. For example, within 5 hours, 3 hours, or 1 hour, after the start of the feeding, the extraction can be started. Furthermore, the extraction volume of the culture medium can be equal to the volume of the medium fed.

When a basic amino acid such as L-lysine is produced, the production can be performed by a method in which fermentation is performed by controlling pH of the medium during culture to be 6.5 to 9.0 and pH of the medium at the end of the culture to be 7.2 to 9.0 while securing a culture period where the medium contains 20 mM or more of bicarbonate ions and/or carbonate ions, so that these bicarbonate ions and/or carbonate ions act as counter ions of the basic amino acid, and the objective basic amino acid is then collected (Japanese Patent Laid-open No. 2002-65287, U.S. Patent Published Application No. 2002/0025564A, EP 1813677 A).

When a microorganism having a basic amino acid-producing ability is cultured in a medium under aerobic conditions, carbonate ions, bicarbonate ions, or both can be used as major counter ions of the basic amino acid. To provide bicarbonate ions and/or carbonate ions in the medium in an amount required to act as counter ions of the basic amino acid, it is known that the pH of the medium can be controlled to be 6.5 to 9.0, or 6.5 to 8.0, during the culture, and can be controlled to be 7.2 to 9.0 at the end of the culture, and the pressure in the fermentation tank can be controlled so that it is positive during fermentation, or carbon dioxide or a mixed gas containing carbon dioxide can be supplied into the medium (Japanese Patent Laid-open No. 2002-65287, U.S. Patent Published Application No. 2002/0025564, EP 1813677 A).

The pressure in the fermentation tank can be controlled to be positive during the fermentation, and carbon dioxide gas or a mixed gas containing carbon dioxide gas can be supplied to the medium. In either case, both can be performed so that there is a culture period where 20 mM or more, 30 mM or more, or 40 mM or more, of bicarbonate ions and/or carbonate ions are present in the medium. The internal pressure of the fermentation tank, the supply amount of carbon dioxide or mixed gas containing carbon dioxide, or the limited gas supply volume can be determined by, for example, measuring bicarbonate ions or carbonate ions in the medium, or measuring pH or ammonia concentration of the medium.

In the above embodiment, pH of the medium can be controlled to be 6.0 to 9.0, or 6.5 to 8.0, during the culture, and 7.2 to 9.0 at the end of the culture. According to the above embodiment, pH of the medium for ensuring the presence of bicarbonate ions and/or carbonate ions in an amount required as counter ions can be made lower compared with the conventional methods. When pH is controlled with ammonia, ammonia is supplied in order to increase the pH, and it can also act as a nitrogen source for the basic amino acid. Examples of cations other than the basic amino acid in the medium include K, Na, Mg, Ca etc. originating in medium components. These can exist in an amount of 50% or less of the total cations.

Furthermore, the internal pressure of the fermentation tank during fermentation can be made positive by, for example, making the gas supply pressure higher than the exhaust pressure. By making the internal pressure of the fermentation tank positive, the carbon dioxide generated by fermentation dissolves in the culture medium to generate bicarbonate ions or carbonate ions, and these can act as counter ions of the basic amino acid. The internal pressure of the fermentation tank can be, specifically, 0.03 to 0.2 MPa, 0.05 to 0.15 MPa, or 0.1 to 0.3 MPa, in terms of the gage pressure (pressure difference with respect to the atmospheric pressure). Moreover, by supplying carbon dioxide or a mixed gas containing carbon dioxide to the culture medium, carbon dioxide can be dissolved in the medium. Furthermore, while supplying carbon dioxide or a mixed gas containing carbon dioxide to the medium, the internal pressure of the fermentation tank can also be adjusted to be positive.

The internal pressure of the fermentation tank can be adjusted to be positive by, for example, making the gas supply pressure higher than the exhaust pressure. Furthermore, when carbon dioxide is supplied to the medium, for example, pure carbon dioxide or a mixed gas containing 5 volume % or more of carbon dioxide can be bubbled in the medium.

The aforementioned methods for dissolving bicarbonate ions and/or carbonate ions in the medium can be used independently, or as a combination of two or more of them.

In the conventional methods, a sufficient amount of ammonium sulfate or ammonium chloride is usually added to the medium to provide counter anions of the basic amino acid to be produced and sulfuric acid or hydrochloric acid decomposition products of proteins etc. are also added to the medium as nutrient components, and hence, sulfate ions and chloride ions generated from these are present in the medium. Therefore, the concentration of the weakly acidic carbonate ions is extremely low during the culture, i.e., it is at a ppm order. The above embodiment is characterized in that these sulfate ions and chloride ions are reduced, and the carbon dioxide released by the microorganism during fermentation is dissolved in the medium under the aforementioned fermentation environment and used as counter ions. Therefore, in the above embodiment, it is not required to add sulfate ions or chloride ions to the medium in an amount more than the amount required for the growth. An appropriate amount of ammonium sulfate or the like can be fed to the medium at an early stage of the culture, and the feeding is terminated in the middle of the culture. Alternatively, ammonium sulfate or the like can be fed while maintaining the balance with the dissolved amount of carbonate ions or bicarbonate ions in the medium. Moreover, as a nitrogen source of the basic amino acid, ammonia can be fed to the medium. Ammonia can be supplied to the medium independently, or together with other gases.

The concentrations of anions other than bicarbonate ions and/or carbonate ions in the medium can be low so long as they are present in amounts that are required for the growth of the microorganism. Examples of such anions include chloride ions, sulfate ions, phosphate ions, ionized organic acids, hydroxide ions, and so forth. The total molar concentration of these other ions is usually 900 mM or lower, 700 mM or lower, 500 mM or lower, 300 mM or lower, or 200 mM or lower.

To reduce the amounts of sulfate ions and/or chloride ions necessaryis one of the objects of the above embodiment, and the amount of sulfate ions or chloride ions or the total amount of both contained in the medium is usually 700 mM or lower, 500 mM or lower, 300 mM or lower, 200 mM or lower, or 100 mM or lower.

If ammonium sulfate is added to a medium as a counter ion source of a basic amino acid, carbon dioxide in the culture medium is usually eliminated by sulfate ions. By contrast, in the above embodiment, it is not necessary to add an excess amount of ammonium sulfate to the medium, and therefore carbon dioxide can be easily dissolved in the fermentation medium.

Furthermore, in the above embodiment, the total ammonia concentration in the medium can be controlled so that "production of the basic amino acid is not inhibited". Examples of such conditions can include, for example, conditions giving yield and/or productivity corresponding to 50% or more, 70% or more, or 90% or more, of the yield and/or productivity obtainable in the production of the basic amino acid under optimal conditions. Specifically, the total ammonia concentration in the medium can be 300 mM or lower, 250 mM or lower, or 200 mM or lower. The dissociation degree of ammonia decreases as the pH becomes higher. Non-dissociating ammonia is more toxic to bacteria compared with ammonium ions. Therefore, the upper limit of the total ammonia concentration should be determined also depending on the pH of the culture medium. That is, as the pH of the culture medium increases, the acceptable total ammonia concentration decreases. Therefore, the aforementioned total ammonia concentration at which "production of the basic amino acid is not inhibited" can be determined for each specific pH value. However, the total ammonia concentration range that is acceptable at the highest pH level during the culture can be used as the upper limit of the total ammonia concentration throughout the entire culture period.

On the other hand, the total concentration of ammonia as a source of nitrogen required for growth of the microorganism and production of the basic substance is not particularly limited, and can be appropriately determined, so long as depletion of ammonia does not continue during the culture, and thus decrease of productivity for the objective substance by the microorganism due to the shortage of the nitrogen source does not occur. For example, the ammonia concentration can be measured over time during the culture, and if ammonia in the medium is depleted, a small amount of ammonia can be added to the medium. Although the ammonia concentration after the addition of ammonia is not particularly limited, the total ammonia concentration can be, for example, 1 mM or higher, 10 mM or higher, or 20 mM or higher.

The L-amino acid can usually be collected from fermentation broth by a combination of conventionally known methods such as ion-exchange resin method (Nagai, H. et al., Separation Science and Technology, 39(16), 3691-3710), precipitation method, membrane separation method (Japanese Patent Laid-open Nos. 9-164323 and 9-173792), crystallization method (WO2008/078448, WO2008/078646), and other methods. When the L-amino acid accumulates in the cells, the cells can be disrupted with, for example, ultrasonic waves or the like, and the L-amino acid can be collected by the ion exchange resin method or the like from the supernatant obtained by removing the cells from the cell-disrupted suspension by centrifugation.

The L-amino acid composition that is collected can also contain bacterial cells, medium components, moisture, and by-product metabolites of the bacterium in addition to the objective L-amino acid. Purity of the collected L-amino acid can be 50% or higher, 85% or higher, or 95% or higher (Japanese Patent No. 1214636, U.S. Pat. Nos. 5,431,933, 4,956,471, 4,777,051, 4,946,654, 5,840,358, 6,238,714, U.S. Patent Published Application No. 2005/0025878).

Furthermore, when L-amino acid deposits in the medium, it can be collected by centrifugation, filtration, or the like. L-Amino acid deposited in the medium and L-amino acid dissolved in the medium can be isolated together after the L-amino acid dissolved in the medium is crystallized.

EXAMPLES

Hereafter, the present invention will be more specifically explained with reference to examples.

Example 1

Acquisition of Strain Showing Improved Fatty Acid-Utilizing Ability

A strain was obtained showing improved fatty acid-utilizing ability by using the MG1655 (ATCC 47076) derived from the *Escherichia coli* wild-type strain, K12 strain, as a parent strain. The MG1655 strain is available from American Type Culture Collection (address: P.O. Box 1549, Manassas, Va. 20108, United States of America).

The MG1655 strain was cultured for 24 hours as static culture on the M9 sodium oleate agar medium (adjusted to pH 7.0 with HCl). The grown cells were scraped off, suspended in a 0.85% NaCl aqueous solution, and inoculated into 5 mL of the M9 sodium oleate liquid medium in an L-shaped test tube at a turbidity of 0.00625 measured at a wavelength of 600 nm. After the culture was performed at 37° C. and 70 rpm for 20 hours by using a constant-temperature shaking incubator TN-2612 (Advantech), 10 μL of the culture broth was transferred to 5 mL of the M9 sodium oleate liquid medium in an L-shaped test tube for subculture. After the subculture was repeated 22 times in the same manner, and for 445 hours in total, the cells were cultured on the M9 sodium oleate agar medium for 24 hours as static culture, then a single colony was collected, and the obtained strain was designated as Fitness 1 strain.

After the Fitness 1 strain was cultured at 37° C. in 5 mL of the M9 sodium oleate liquid medium until the final OD600 became about 0.6, a 40% glycerol solution was added to the culture medium in the same volume as that of the culture medium, and the mixture was stirred, divided into appropriate volumes, and stored at −80° C. This preparation was called glycerol stock of the Fitness 1 strain.

Compositions of the media mentioned above are shown below. All the concentrations are final concentrations.

Composition of M9 sodium oleate agar medium:

| Sodium oleate (Junsei Chemical) | 2 g/L |
|---|---|
| Tween 80* (Nakalai Tesque) | 0.5% (v/v) |
| Na2HPO4 | 6 g/L |
| KH2PO4 | 3 g/L |
| NaCl | 0.5 g/L |
| NH4Cl | 1 g/L |
| MgSO4•7H2O | 0.246 g/L |
| Thiamine | 0.5 mg/L |
| Agar | 15 g/L |

*Poly(oxyethylene)sorbitan monooleate

Composition of M9 sodium oleate liquid medium for test tube

| Sodium oleate (Junsei Chemical) | 1 g/L |
|---|---|
| Tween 80 (Nakalai Tesque) | 0.5% (v/v) |
| Na2HPO4 | 6 g/L |
| KH2PO4 | 3 g/L |
| NaCl | 0.5 g/L |
| NH4Cl | 1 g/L |
| MgSO4•7H2O | 0.246 g/L |
| Thiamine | 0.5 mg/L |

Example 2

Culture of Microorganism Showing Improved Fatty Acid-Utilizing Ability

The glycerol stock of Fitness 1 strain was cultured for 24 hours as static culture on the M9 sodium oleate agar medium (adjusted to pH 7.0 with HCl). The grown cells were scraped off, suspended in a 0.85% NaCl aqueous solution, and inoculated into 5 mL of the M9 sodium oleate liquid medium in an L-shaped test tube at a turbidity of 0.005 measured at a wavelength of 600 nm. The culture was performed at 37° C. and 70 rpm for 20 hours by using a constant-temperature shaking incubator TN-2612 (Advantech), and as a result, the Fitness 1 strain showed significantly improved growth compared with the MG1655 strain cultured under the same condition (FIG. 1).

Figure 2:
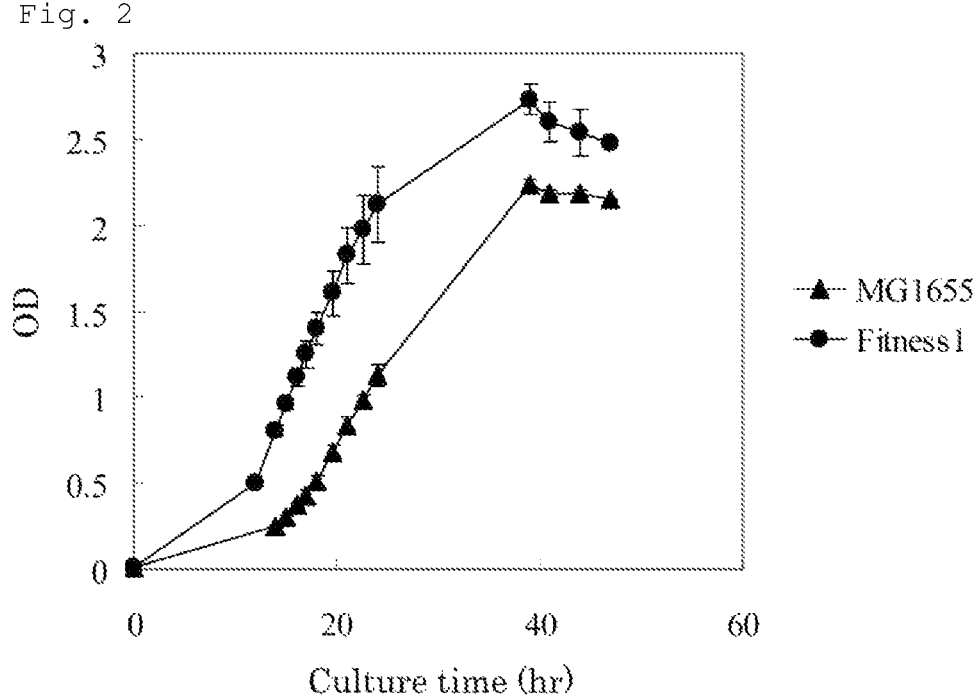
FIG. 2 shows growth of the MG1655 strain and the Fitness 1 strain in flask culture using only oleic acid as a carbon source.
Figure 3:
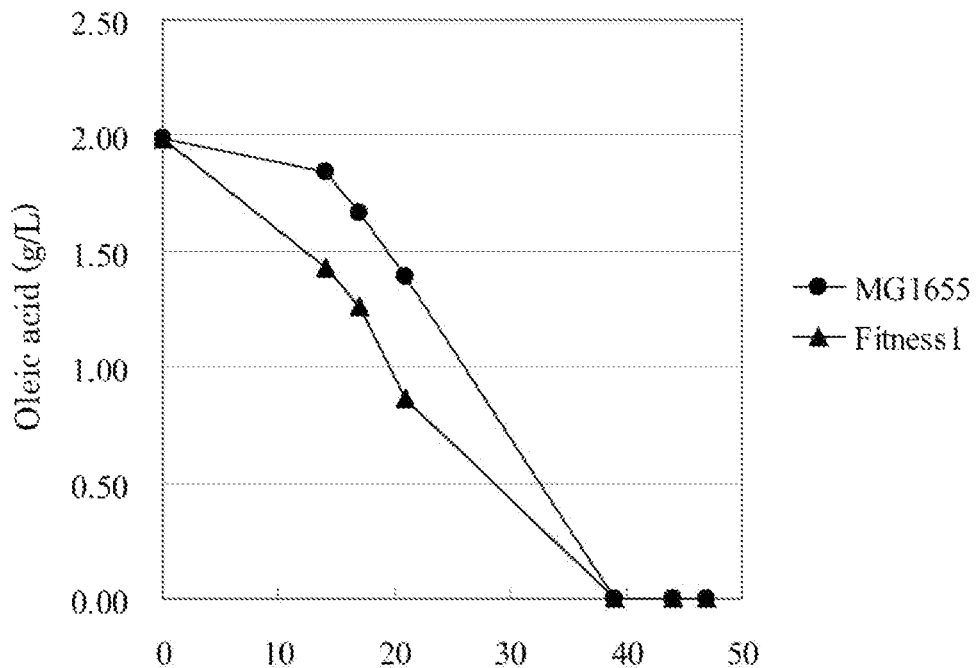
FIG. 3 shows consumption of oleic acid by the MG1655 strain and the Fitness 1 strain in flask culture using only oleic acid as a carbon source.

Furthermore, the glycerol stock of Fitness 1 strain was cultured for 24 hours as static culture on the M9 sodium oleate agar medium (adjusted to pH 7.0 with HCl). The cells on the agar medium were scraped off, suspended in a 0.85% NaCl aqueous solution, and inoculated into 20 mL of M9 special grade oleic acid liquid medium in a 500-mL volume Sakaguchi flask at a turbidity of 0.01 measured at a wavelength of 600 nm. The culture was performed at 37° C. and a stifling speed of 200 rpm for 47 hours by using a reciprocal incubator. The medium was collected during the culture, and mixed with an equal volume of a 10% Tween 80 aqueous solution, then the turbidity of the mixture at a wavelength of 600 nm was measured, and the oleic acid concentration in the culture medium was measured by gas chromatography according to the method described by Hashimoto et al. (Hashimoto, K. et al., 1996, Biosci. Biotechnol. Biochem., 70:22-30). As a result, the Fitness 1 strain showed significantly improved growth and fatty acid consumption rate compared with the MG1655 strain cultured under the same condition (FIGS. 2 and 3).

Composition of the medium mentioned above is shown below. All the concentrations are final concentrations.

Composition of M9 special grade oleic acid liquid medium for flask:

| Oleic acid (special grade, Nakalai Tesque) | 2 g/L |
|---|---|
| Tween 80 (Nakalai Tesque) | 0.5% (v/v) |
| Na2HPO4 | 6 g/L |
| KH2PO4 | 3 g/L |
| NaCl | 0.5 g/L |
| NH4Cl | 1 g/L |
| MgSO4•7H2O | 0.246 g/L |
| Thiamine | 0.5 mg/L |

Example 3

Identification of Mutation in Fitness 1 Strain

Mutation sites on the chromosome of the Fitness 1 strain were searched for by the CGS method described by Herring et al. (Herring, C. D. et al., 2006, Nat. Genet., 38:1406-1412). As a result, it was found that, in the Fitness 1 strain, G at position 628 in the nucleotide sequence of the rpsA gene of the MG1655 strain (SEQ ID NO: 1) was mutated to T.

It became clear that the aspartic acid residue at position 210 in the amino acid sequence of the RpsA protein (SEQ ID NO: 2) encoded by the rpsA gene of the MG1655 strain was replaced with a tyrosine residue due to this mutation. This mutation was designated as RpsA (D210Y) mutation.

The nucleotide sequence of the mutant rpsA gene of the Fitness 1 strain, and the amino acid sequence of the mutant RpsA encoded by this gene are shown in SEQ ID NOS: 3 and 4, respectively.

Sequences around position 210 of the amino acid sequences derived from rpsA gene homologues of various organisms were compared, and it became clear that the aspartic acid residue at position 210 was highly conserved in a wide range of species including prokaryotes to eukaryotes. The rpsA gene was considered to be an indispensable gene for Enterobacteriaceae bacteria such as *Escherichia coli*, and it was difficult to predict that adaptive mutation at a highly conserved amino acid residue of such a gene should provide significant improvement in growth. Moreover, the effect of harboring a mutant RpsA is expected not only in Enterobacteriaceae bacteria, but also in a wider range of families.

Example 4

Introduction of RpsA (D210Y) Mutation into *Escherichia coli*

The RpsA (D210Y) mutation was introduced into an *Escherichia coli* strain having a wild-type rpsA gene.

Firstly, a strain of the Fitness 1 strain deficient in the ycaI gene neighboring the rpsA on the chromosome was constructed. PCR was performed by using pMW118-attL-Cm-attR plasmid (described in Japanese Patent Laid-open No. 2005-58227 (WO2005/010175)) as a template and the synthetic oligonucleotides shown in SEQ ID NOS: 7 and 8 having sequences corresponding to the both ends of the attachment sites of λ phage, attL and attR, at the 3' ends of the oligonucleotides and sequences corresponding to a part of the ycaI gene at the 5' ends of the oligonucleotides as primers, and Fitness1ΔycaI::att-Cm strain deficient in the ycaI gene was constructed by using the λ-red method (U.S. Patent Published Application No. 2006/0160191, Datsenko, K. A, and Wanner, B. L., 2000, Proc. Natl. Acad. Sci., USA, 97:6640-6645). pMW118-attL-Cm-attR is a plasmid obtained by inserting attL and attR genes, which are the attachment sites of λ phage, and the cat gene, which is an antibiotic resistance gene, into pMW118 (Takara Bio), and the genes are inserted in the order of attL-cat-attR.

P1 lysate was obtained from the Fitness1ΔycaI::att-Cm strain in a conventional manner, and transduction was performed with the MG1655 strain to construct MG1655ΔycaI::att-Cm,rpsA(D210Y) strain having the RpsA (D210Y) mutation on the chromosome. Furthermore, PCR was performed by using pMW118-attL-Cm-attR (described in Japanese Patent Laid-open No. 2005-58227), the same as that used for the construction of the Fitness1ΔycaI::att-Cm strain, as a template and the synthetic oligonucleotides shown in SEQ ID NOS: 7 and 8 as primers, and MG1655ΔycaI::att-Cm strain, which is a strain of the MG1655 deficient in the ycaI gene on the chromosome, was constructed by similarly using the λ-red method. Glycerol stock of this strain was prepared in the same manner as that used in Example 1.

A gene fragment containing the RpsA (D210Y) mutation can be constructed by PCR using the genomic DNA of the MG1655 strain as a template and synthetic oligonucleotides shown in SEQ ID NOS: 5 and 6 as primers, and used to introduce the RpsA (D210Y) mutation into *Escherichia coli* by using an appropriate combination of crossover PCR, λ-red method, homologous recombination, and so forth.

Example 5

Figure 4:
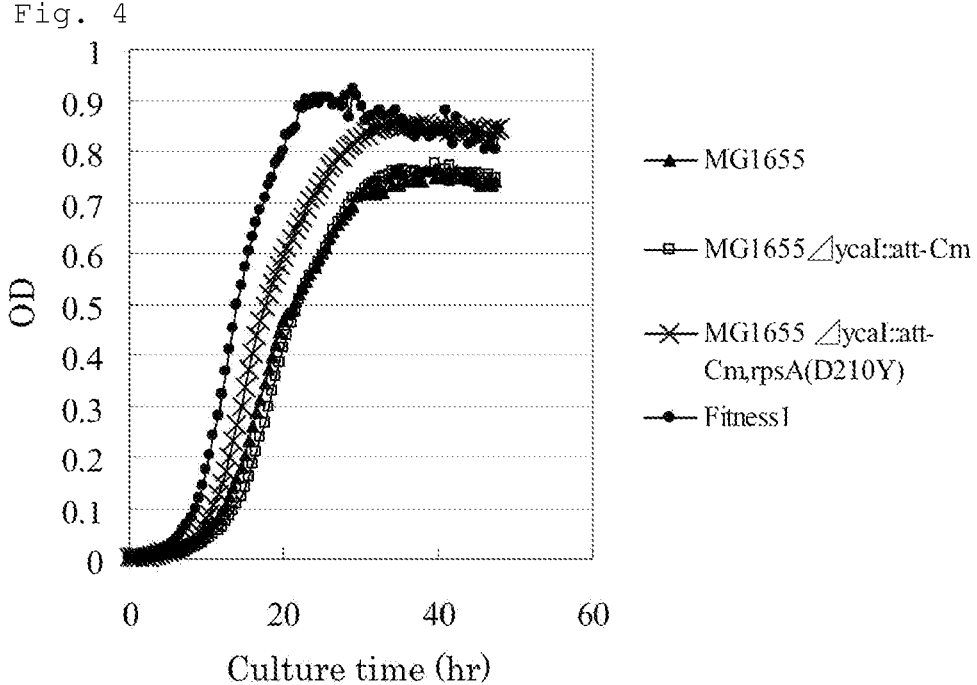
FIG. 4 shows growth of the MG1655, Fitness 1, MG1655ΔycaI::att-Cm, and MG1655ΔycaI::att-Cm,rpsA(D210Y) strains in test tube culture using only oleate as a carbon source.

Growth-Improving Effect Provided by RpsA (D210Y) Mutation in Medium Containing Fatty Acid as Carbon Source The glycerol stock of the MG1655ΔycaI::att-Cm,rpsA (D210Y) strain was cultured for 24 hours as static culture on the M9 sodium oleate agar medium (adjusted to pH 7.0 with HCl). The grown cells were scraped off, suspended in a 0.85% NaCl aqueous solution, and inoculated into 5 mL of the M9 sodium oleate liquid medium in an L-shaped test tube at a turbidity of 0.005 measured at a wavelength of 600 nm. The culture was performed at 37° C. and 70 rpm for 20 hours by using a constant-temperature shaking incubator TN-2612 (Advantech). As a result, the MG1655ΔycaI::att-Cm,rpsA (D210Y) strain showed significantly improved growth compared with the MG1655 strain or MG1655ΔycaI::att-Cm strain cultured under the same condition (FIG. 4).

Example 6

Figure 5:
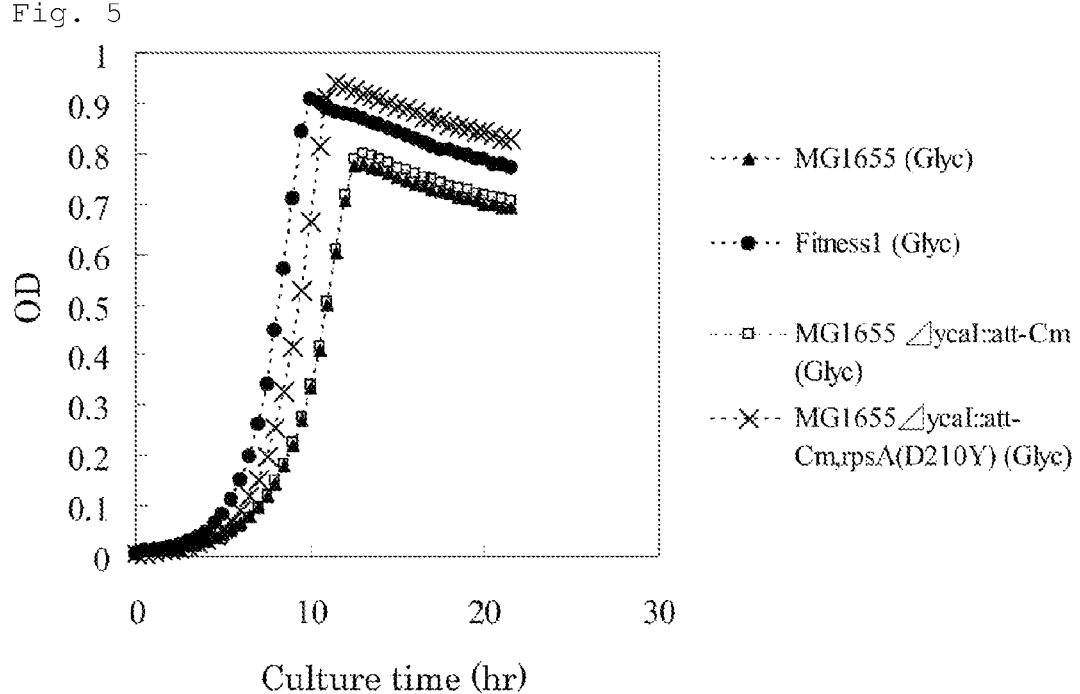
FIG. 5 shows growth of the MG1655, Fitness 1, MG1655ΔycaI::att-Cm, and MG1655ΔycaI::att-Cm,rpsA(D210Y) strains in test tube culture using only glycerol as a carbon source.

Growth-Improving Effect Provided by RpsA (D210Y) Mutation in Medium Containing Glycerol as Carbon Source The glycerol stock of the MG1655ΔycaI::att-Cm,rpsA (D210Y) strain was cultured for 24 hours as static culture on the M9 sodium oleate agar medium (adjusted to pH 7.0 with HCl). The grown cells were scraped off, suspended in a 0.85% NaCl aqueous solution, and inoculated into 5 mL of M9 glycerol liquid medium in an L-shaped test tube at a turbidity of 0.005 measured at a wavelength of 600 nm. The culture was performed at 37° C. and 70 rpm for 20 hours by using a constant-temperature shaking incubator TN-2612 (Advantech). As a result, the MG1655ΔycaI::att-Cm,rpsA (D210Y) strain showed significantly improved growth compared with the MG1655 strain or MG1655ΔycaI::att-Cm strain cultured under the same condition (FIG. 5).

Composition of the medium mentioned above is shown below. All the concentrations are final concentrations.

Composition of M9 glycerol liquid medium for test tube

| | |
|---|---|
| Glycerol (special grade, Junsei Chemical) | 1 g/L |
| Tween 80 (Nakalai Tesque) | 0.5% (v/v) |
| Na2HPO4 | 6 g/L |
| KH2PO4 | 3 g/L |
| NaCl | 0.5 g/L |
| NH4Cl | 1 g/L |
| MgSO4•7H2O | 0.246 g/L |
| Thiamine | 0.5 mg/L |

Example 7

Introduction of RpsA (D210Y) Mutation into L-Lysine-Producing Bacterium WC196LC/pCABD2

P1 lysate was obtained from the Fitness1ΔycaI::att-Cm strain in a conventional manner, and the L-lysine-producing bacterium WC196LC/pCABD2 strain (U.S. Patent Published Application No. 2006/0160191) was used as a host to construct WC196ΔLCΔycaI::att-Cm,rpsA(D210Y)/pCABD2 strain by using the P1 transduction method. The WC196LC (WCΔcadAΔldc, FERM BP-11027) strain is obtained from the *Escherichia coli* WC1-96 strain by disrupting the lysine decarboxylase genes, cadA and ldc, according to the method using the Red-driven integration method (Datsenko K. A., Wanner, B. L., 2000, Proc. Natl. Acad. Sci. USA, 97, 6640-6645) and the excision system derived from λ-phage (Cho, E. H., Gumport, R. I., Gardner, J. F., 2002, J. Bacteriol., 184: 5200-5203) in combination (refer to WO2005/010175). A strain obtained by introducing pCABD2 into this strain is the WC196LC/pCABD2 strain. The plasmid pCABD2 contains a mutant dapA gene coding for dihydrodipicolinate synthase (DDPS) derived from *Escherichia coli* having a mutation for desensitization to feedback inhibition by L-lysine, a mutant lysC gene coding for aspartokinase III derived from *Escherichia coli* having a mutation for desensitization to feedback inhibition by L-lysine, the dapB gene coding for dihydrodipicolinate reductase derived from *Escherichia coli*, and the ddh gene coding for diaminopimelate dehydrogenase derived from *Brevibacterium lactofermentum* (U.S. Pat. No. 6,040,160).

The WC196LCΔycaI::att-Cm,rpsA(D210Y)/pCABD2 strain was cultured at 37° C. in L medium containing 20 mg/L of streptomycin until the final OD600 became about 0.6. Glycerol stock was prepared in the same manner as that used in Example 1.

Example 8

Evaluation of L-Lysine-Producing Ability of L-Lysine-Producing Bacterium Introduced with RpsA (D210Y) Mutation from Fatty Acid or Glycerol as Carbon Source The glycerol stock of the WC196LCΔycaI::att-Cm,rpsA (D210Y)/pCABD2 strain obtained in Example 7 was thawed, 100 µL of the thawed stock was uniformly applied to an L plate containing 20 mg/L of streptomycin, and culture was performed at 37° C. for 24 hours as static culture. About ¼ of the cells on the plate were suspended in 0.5 mL of physiological saline, and turbidity was measured at a wavelength of 600 nm by using a spectrophotometer U-2000 (Hitachi, Ltd.). The obtained suspension containing the bacterium was inoculated in 40 mL of the fermentation medium (described below) containing 20 mg/L of streptomycin contained in a 500-mL volume Erlenmeyer flask with baffles in such a volume that the turbidity measured at a wavelength of 600 nm became 0.2, and culture was performed at 37° C. for 48 hours at a rotation number of 200 rpm by using a rotary shaking incubator, InnOva 4430 (New Brunswick Scientific).

As the carbon source for the main culture, sodium oleate or glycerol was used. Tween 80 was added at a final concentration of 0.5% (v/v) as an emulsification enhancer. The total amount of the carbon source was 10 g/L. It was separately confirmed that *Escherichia coli* could not utilize Tween 80 by using the M9 minimal medium containing Tween 80.

The culture was performed for 48 hours under the aforementioned conditions, and amount of L-lysine accumulated in the medium was measured by using Biotech Analyzer AS310 (Sakura Seiki). Complete consumption of the carbon source added to the medium was confirmed by using a gas chromatograph GC-2014 (Shimadzu) in the case of the oleate, or Biotech Analyzer BF-5 (Oji Scientific Instruments) in the case of glycerol. Furthermore, Tween 80 was added at a final concentration of 1.0% (w/v) immediately after the end of the culture, the resultant was appropriately diluted, and turbidity was measured at a wavelength of 600 nm by using a spectrophotometer U-2000 (Hitachi, Ltd.) to measure cell amount at the time of the end of the culture.

The WC196LC/pCABD2 strain and the WC196LCΔycaI:: att-Cm/pCABD2 strain were also cultured in the same manner as described above.

Composition of the fermentation medium used for the main culture containing oleate as the carbon source is shown below. The concentrations mentioned in the unit of g/L or % (in terms of volume/volume) are all final concentrations.

| Sodium oleate (first grade, Junsei Chemical) | 10 g/L |
| Tween 80 | 0.5% |
| MgSO4•7H2O | 1 g/L |
| PIPES | 20 g/L |
| (NH4)2SO4 | 16 g/L |
| KH2PO4 | 1 g/L |
| FeSO4•7H2O | 0.01 g/L |
| MnSO4•4H2O | 0.082 g/L |
| Yeast extract (Difco) | 2 g/L |

Sodium oleate was adjusted to pH 7.5 with HCl and autoclaved at 115° C. for 10 minutes. Tween 80 was subjected to filter sterilization using Nalgene 0.45 µm filter (Nalgene). MgSO4.7H2O was autoclaved at 115° C. for 10 minutes. PIPES was adjusted to pH 7.5 with NaOH and autoclaved at 115° C. for 10 minutes. The ingredients other than the above were mixed, adjusted to pH 7.5 with KOH, and autoclaved at 115° C. for 10 minutes.

As described above, the ingredients were divided into five groups, separately sterilized, and then mixed.

Composition of the fermentation medium used for the main culture containing glycerol as the carbon source is shown below. The concentrations mentioned in the unit of g/L or % (in terms of volume/volume) are all final concentrations.

| Glycerol (special grade, Junsei Chemical) | 10 g/L |
| Tween 80 | 0.5% |
| MgSO4•7H2O | 1 g/L |
| PIPES (pH 7.5) | 20 g/L |
| (NH4)2SO4 | 16 g/L |
| KH2PO4 | 1 g/L |
| FeSO4•7H2O | 0.01 g/L |
| MnSO4•4H2O | 0.082 g/L |
| Yeast extract (Difco) | 2 g/L |

Glycerol was autoclaved at 115° C. for 10 minutes. Tween 80 was subjected to filter sterilization using Nalgene 0.45 µm filter (Nalgene). MgSO4.7H$_2$O was autoclaved at 115° C. for 10 minutes. PIPES was adjusted to pH 7.5 with NaOH and autoclaved at 115° C. for 10 minutes. The ingredients other than the above were mixed, adjusted to pH 7.5 with KOH, and autoclaved at 115° C. for 10 minutes.

As described above, the ingredients were divided into five groups, separately sterilized, and then mixed.

The results of the main culture are shown in Table 1. The values of "Lys (g/L)" indicate amounts of L-lysine which accumulated in the flasks. The RpsA (D210Y) mutation-introduced strain (WC196LCΔycaI::att-Cm,rpsA(D210Y)/pCABD2 strain) showed significantly higher L-lysine production compared with the control strains (WC196LC/pCABD2 strain and WC196LCΔycaI::att-Cm/pCABD2 strain). It was demonstrated that L-lysine-producing ability was improved by the introduction of the RpsA (D210Y) mutation.

TABLE 1

| Carbon source | Strain | OD | Lys (g/L) | Yield (%) |
|---|---|---|---|---|
| Glycerol | WC196LC/pCABD2 | 5.10 | 4.07 | 39.9 |
| Glycerol | WC196LCΔycaI::att-Cm/pCABD2 | 5.00 | 4.05 | 39.7 |
| Glycerol | WC196LCΔycaI::att-Cm,rpsA(D210Y)/pCABD2 | 5.00 | 4.34 | 42.5 |
| Oleate | WC196LC/pCABD2 | 8.10 | 4.20 | 45.3 |
| Oleate | WC196LCΔycaI::att-Cm/pCABD2 | 8.34 | 4.15 | 44.8 |
| Oleate | WC196LCΔycaI::att-Cm,rpsA(D210Y)/pCABD2 | 9.27 | 4.35 | 46.9 |

Example 9

Impartation of Ethanol-Utilizing Ability to WC196LC Strain

In order to impart ethanol-utilizing ability to the L-lysine-producing bacterium, a mutant alcohol dehydrogenase gene (adhE*) was introduced. As the mutant alcohol dehydrogenase gene, the gene derived from the MG1655::PL-tacadhE* strain (refer to WO2008/010565) was used. The MG1655:PL-tacadhE* strain is obtained by inserting a DNA fragment which includes the chloramphenicol resistance gene (cat) and a mutant adhE gene controlled by the PL-tac promoter into the genome of the Escherichia coli MG1655 strain. This mutant adhE gene codes for an alcohol dehydrogenase that maintains the activity under aerobic conditions.

In order to make it possible to remove the cat gene from the genome, the cat gene was replaced with a DNA fragment obtained by ligating the attachment site of λ phage and the tetracycline resistance gene (att-tet). For the replacement of the cat gene with the att-tet gene, the λ-red method was used. As the primers for the replacement of the cat gene with the att-tet gene, the primers of SEQ ID NOS: 9 and 10 were used. In this way, MG1655-att-tet-PL-tacadhE* strain, which is a strain of the MG1655::PL-tacadhE* strain in which the cat gene is replaced with the att-tet gene, was obtained.

In order to impart ethanol-utilizing ability to the L-lysine-producing bacterium, P1 lysate was obtained from the MG1655-att-tet-PL-tacadhE* strain in a conventional manner, and the L-lysine-producing bacterium WC196LC strain was used as a host to obtain WC196LC-att-tet-PL-tacadhE* strain by using the P1 transduction method.

Then, in order to remove the att-tet gene introduced upstream of the PL-tac promoter, a helper plasmid pMW-intxis-ts (U.S. Patent Published Application No. 2006/0141586) was used. pMW-intxis-ts is a plasmid carrying a gene coding for λ phage integrase (Int) and a gene coding for λ phage excisionase (Xis), and having temperature sensitive replication ability.

Competent cells of the WC196LC-att-tet-PL-tacadhE* strain obtained as described above were prepared in a conventional manner, transformed with the helper plasmid pMW-intxis-ts, and cultured at 30° C. on a plate of the LB agar medium containing 50 mg/L of ampicillin to select an ampicillin-resistant strain. Then, to remove the pMW-intxis-ts plasmid, the transformant was cultured at 42° C. on the LB agar medium, and ampicillin resistance and tetracycline resistance of the obtained colonies were examined to obtain an ampicillin and tetracycline-sensitive strain. Thus, a PL-tacadhE*-introduced strain not containing att-tet and pMW-intxis-ts was obtained. This strain was designated as WC196LC PL-tacadhE* strain.

Example 10

Introduction of RpsA (D210Y) Mutation and Plasmid for L-Lysine Production (pCABD2) into WC196LC PL-tacadhE* Strain P1 lysate was obtained from the Fitness1ΔycaI::att-Cm strain in a conventional manner, and the L-lysine-producing bacterium WC196LC PL-tacadhE* strain was used as a host to construct WC196LC PL-tacadhE*ΔycaI::att-Cm,rpsA(D210Y) strain by using the P1 transduction method. In the same manner, P1 lysate was obtained from the MG1655ΔycaI::att-Cm strain, and the WC196LC PL-tacadhE* strain was used as a host to construct WC196LC PL-tacadhE*ΔycaI::att-Cm strain by using the P1 transduction method.

The WC196LC PL-tacadhE*ΔycaI::att-Cm,rpsA(D210Y) strain and the WC196LC PL-tacadhE*ΔycaI::att-Cm strain were transformed with pCABD2 in a conventional manner to obtain WC196 PL-tacadhE*ΔycaI::att-Cm,rpsA(D210Y)/pCABD2 strain and WC196LC PL-tacadhE*ΔycaI::att-Cm/pCABD2 strain. Each of these strains was cultured at 37° C. in the L medium containing 20 mg/L of streptomycin until the final OD600 became about 0.6, and glycerol stocks were prepared in the same manner as that used in Example 1.

Example 11

Evaluation of L-Lysine-Producing Ability of RpsA (D210Y) Mutation-Introduced Strain from Ethanol Each of the glycerol stocks of the strains obtained in Example 10 is thawed, 100 µL of each of the thawed stocks is uniformly applied to an L-plate containing 20 mg/L of streptomycin, and culture is performed at 37° C. for 15 hours. The obtained cells are suspended in a 0.85% NaCl aqueous solution, inoculated into 5 mL of a fermentation medium containing 20 mg/L of streptomycin contained in a large size test tube (internal diameter: 18 mm) at an initial OD600 of 0.25, and cultured at 37° with stifling at 120 rpm by using a reciprocal incubator.

Composition of the fermentation medium containing ethanol as the carbon source is shown below.

Composition of L-lysine fermentation medium containing ethanol as carbon source:

| | |
|---|---|
| Ethanol | 10 ml/L |
| (NH4)2SO4 | 24 g/L |
| K2HPO4 | 1.0 g/L |
| MgSO4•7H2O | 1.0 g/L |
| FeSO4•7H2O | 0.01 g/L |
| MnSO4•5H2O | 0.01 g/L |
| Yeast extract | 2.0 g/L |
| CaCO3 (Japanese Pharmacopoeia) | 30 g/L |

The aforementioned ingredients are dissolved in a final volume of 1 L, adjusted to pH 5.7 with KOH, and autoclaved at 115° C. for 10 minutes, provided that ethanol, MgSO4.7H$_2$O, and CaCO$_3$ are separately sterilized. Ethanol is sterilized by filter filtration. MgSO4.7H$_2$O is dissolved in distilled water and autoclaved. CaCO3 is subjected to dry sterilization at 180° C. for 2 hours. As an antibiotic, 20 mg/L of streptomycin is added.

After the culture for 16 hours, the amount of L-lysine that accumulates in the medium is measured by a known method (Biotech Analyzer AS310, Sakura Seiki)

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for producing an L-amino acid, the method comprising:
   A) culturing a bacterium belonging to the family Enterobacteriaceae and having an L-amino acid-producing ability in a medium containing a carbon source selected from the group consisting of a fatty acid and an alcohol; and
   B) collecting the L-amino acid from the medium,
   wherein the bacterium expresses an ribosomal protein S1 RpsA protein comprising the amino acid sequence of SEQ ID NO: 2, wherein said RpsA protein has a mutation in which the aspartic acid residue at position 210 of SEQ ID NO: 2 is replaced with a different amino acid residue, and wherein said bacterium is *Escherichia coli*.

2. The method according to claim 1, wherein the different amino acid residue is a tyrosine residue.

3. The method according to claim 1, wherein the bacterium does not express an RpsA protein not having said mutation.

4. The method according to claim 1, wherein the chromosome of the bacterium expresses a mutant rpsA gene coding for the RpsA protein having the mutation.

5. The method according to claim 1, wherein the carbon source is a fatty acid.

6. The method according to claim 5, wherein the fatty acid is oleic acid.

7. The method according to claim 5, wherein the fatty acid is a mixture of fatty acids derived from fat or oil.

8. The method according to claim 1, wherein the carbon source is an alcohol.

9. The method according to claim 8, wherein the alcohol is glycerol.

10. The method according to claim 8, wherein the alcohol is ethanol.

11. The method according to claim 1, wherein the carbon source is a mixture of a fatty acid and glycerol obtained by hydrolyzing fat or oil.

* * * * *

SEQUENCE LISTING

```
<160> NUMBER OF SEQ ID NOS: 17

<210> SEQ ID NO 1
<211> LENGTH: 1674
<212> TYPE: DNA
<213> ORGANISM: Escherichia coli
<220> FEATURE:
<221> NAME/KEY: CDS
<222> LOCATION: (1)..(1674)

<400> SEQUENCE: 1 atg act gaa tct ttt gct caa ctc ttt gaa gag tcc tta aaa gaa atc        48
Met Thr Glu Ser Phe Ala Gln Leu Phe Glu Glu Ser Leu Lys Glu Ile
1               5                   10                  15 gaa acc cgc ccg ggt tct atc gtt cgt ggc gtt gtt gtt gct atc gac        96
Glu Thr Arg Pro Gly Ser Ile Val Arg Gly Val Val Val Ala Ile Asp
                20                  25                  30 aaa gac gta gta ctg gtt gac gct ggt ctg aaa tct gag tcc gcc atc       144
Lys Asp Val Val Leu Val Asp Ala Gly Leu Lys Ser Glu Ser Ala Ile
            35                  40                  45 ccg gct gag cag ttc aaa aac gcc cag ggc gag ctg gaa atc cag gta       192
Pro Ala Glu Gln Phe Lys Asn Ala Gln Gly Glu Leu Glu Ile Gln Val
        50                  55                  60 ggt gac gaa gtt gac gtt gct ctg gac gca gta gaa gac ggc ttc ggt       240
Gly Asp Glu Val Asp Val Ala Leu Asp Ala Val Glu Asp Gly Phe Gly
65                  70                  75                  80 gaa act ctg ctg tcc cgt gag aaa gct aaa cgt cac gaa gcc tgg atc       288
Glu Thr Leu Leu Ser Arg Glu Lys Ala Lys Arg His Glu Ala Trp Ile
                85                  90                  95 acg ctg gaa aaa gct tac gaa gat gct gaa act gtt acc ggt gtt atc       336
Thr Leu Glu Lys Ala Tyr Glu Asp Ala Glu Thr Val Thr Gly Val Ile
                100                 105                 110 aac ggc aaa gtt aag ggc ggc ttc act gtt gag ctg aac ggt att cgt       384
Asn Gly Lys Val Lys Gly Gly Phe Thr Val Glu Leu Asn Gly Ile Arg
            115                 120                 125 gcg ttc ctg cca ggt tct ctg gta gac gtt cgt ccg gtg cgt gac act       432
Ala Phe Leu Pro Gly Ser Leu Val Asp Val Arg Pro Val Arg Asp Thr
        130                 135                 140 ctg cac ctg gaa ggc aaa gag ctt gaa ttt aaa gta atc aag ctg gat       480
Leu His Leu Glu Gly Lys Glu Leu Glu Phe Lys Val Ile Lys Leu Asp
145                 150                 155                 160 cag aag cgc aac aac gtt gtt gtt tct cgt cgt gcc gtt atc gaa tcc       528
Gln Lys Arg Asn Asn Val Val Val Ser Arg Arg Ala Val Ile Glu Ser
                165                 170                 175 gaa aac agc gca gag cgc gat cag ctg ctg gaa aac ctg cag gaa ggc       576
Glu Asn Ser Ala Glu Arg Asp Gln Leu Leu Glu Asn Leu Gln Glu Gly
                180                 185                 190 atg gaa gtt aaa ggt atc gtt aag aac ctc act gac tac ggt gca ttc       624
Met Glu Val Lys Gly Ile Val Lys Asn Leu Thr Asp Tyr Gly Ala Phe
            195                 200                 205 gtt gat ctg ggc ggc gtt gac ggc ctg ctg cac atc act gac atg gcc       672
Val Asp Leu Gly Gly Val Asp Gly Leu Leu His Ile Thr Asp Met Ala
        210                 215                 220 tgg aaa cgc gtt aag cat ccg agc gaa atc gtc aac gtg ggc gac gaa       720
Trp Lys Arg Val Lys His Pro Ser Glu Ile Val Asn Val Gly Asp Glu
225                 230                 235                 240 atc act gtt aaa gtg ctg aag ttc gac cgc gaa cgt acc cgt gta tcc       768
```

```
Ile Thr Val Lys Val Leu Lys Phe Asp Arg Glu Arg Thr Arg Val Ser
            245                 250                 255 ctg ggc ctg aaa cag ctg ggc gaa gat ccg tgg gta gct atc gct aaa      816
Leu Gly Leu Lys Gln Leu Gly Glu Asp Pro Trp Val Ala Ile Ala Lys
            260                 265                 270 cgt tat ccg gaa ggt acc aaa ctg act ggt cgc gtg acc aac ctg acc      864
Arg Tyr Pro Glu Gly Thr Lys Leu Thr Gly Arg Val Thr Asn Leu Thr
            275                 280                 285 gac tac ggc tgc ttc gtt gaa atc gaa gaa ggc gtt gaa ggc ctg gta      912
Asp Tyr Gly Cys Phe Val Glu Ile Glu Glu Gly Val Glu Gly Leu Val
        290                 295                 300 cac gtt tcc gaa atg gac tgg acc aac aaa aac atc cac ccg tcc aaa      960
His Val Ser Glu Met Asp Trp Thr Asn Lys Asn Ile His Pro Ser Lys
305                 310                 315                 320 gtt gtt aac gtt ggc gat gta gtg gaa gtt atg gtt ctg gat atc gac     1008
Val Val Asn Val Gly Asp Val Val Glu Val Met Val Leu Asp Ile Asp
                325                 330                 335 gaa gaa cgt cgt cgt atc tcc ctg ggt ctg aaa cag tgc aaa gct aac     1056
Glu Glu Arg Arg Arg Ile Ser Leu Gly Leu Lys Gln Cys Lys Ala Asn
                    340                 345                 350 ccg tgg cag cag ttc gcg gaa acc cac aac aag ggc gac cgt gtt gaa     1104
Pro Trp Gln Gln Phe Ala Glu Thr His Asn Lys Gly Asp Arg Val Glu
                355                 360                 365 ggt aaa atc aag tct atc act gac ttc ggt atc ttc atc ggc ttg gac     1152
Gly Lys Ile Lys Ser Ile Thr Asp Phe Gly Ile Phe Ile Gly Leu Asp
    370                 375                 380 ggc ggc atc gac ggc ctg gtt cac ctg tct gac atc tcc tgg aac gtt     1200
Gly Gly Ile Asp Gly Leu Val His Leu Ser Asp Ile Ser Trp Asn Val
385                 390                 395                 400 gca ggc gaa gaa gca gtt cgt gaa tac aaa aaa ggc gac gaa atc gct     1248
Ala Gly Glu Glu Ala Val Arg Glu Tyr Lys Lys Gly Asp Glu Ile Ala
                    405                 410                 415 gca gtt gtt ctg cag gtt gac gca gaa cgt gaa cgt atc tcc ctg ggc     1296
Ala Val Val Leu Gln Val Asp Ala Glu Arg Glu Arg Ile Ser Leu Gly
                420                 425                 430 gtt aaa cag ctc gca gaa gat ccg ttc aac aac tgg gtt gct ctg aac     1344
Val Lys Gln Leu Ala Glu Asp Pro Phe Asn Asn Trp Val Ala Leu Asn
    435                 440                 445 aag aaa ggc gct atc gta acc ggt aaa gta act gca gtt gac gct aaa     1392
Lys Lys Gly Ala Ile Val Thr Gly Lys Val Thr Ala Val Asp Ala Lys
450                 455                 460 ggc gca acc gta gaa ctg gct gac ggc gtt gaa ggt tac ctg cgt gct     1440
Gly Ala Thr Val Glu Leu Ala Asp Gly Val Glu Gly Tyr Leu Arg Ala
465                 470                 475                 480 tct gaa gca tcc cgt gac cgc gtt gaa gac gct acc ctg gtt ctg agc     1488
Ser Glu Ala Ser Arg Asp Arg Val Glu Asp Ala Thr Leu Val Leu Ser
                    485                 490                 495 gtt ggc gac gaa gtt gaa gct aaa ttc acc ggc gtt gat cgt aaa aac     1536
Val Gly Asp Glu Val Glu Ala Lys Phe Thr Gly Val Asp Arg Lys Asn
                500                 505                 510 cgc gca atc agc ctg tct gtt cgt gcg aaa gac gaa gct gac gag aaa     1584
Arg Ala Ile Ser Leu Ser Val Arg Ala Lys Asp Glu Ala Asp Glu Lys
            515                 520                 525 gat gca atc gca act gtt aac aaa cag gaa gat gca aac ttc tcc aac     1632
Asp Ala Ile Ala Thr Val Asn Lys Gln Glu Asp Ala Asn Phe Ser Asn
        530                 535                 540 aac gca atg gct gaa gct ttc aaa gca gct aaa ggc gag taa              1674
Asn Ala Met Ala Glu Ala Phe Lys Ala Ala Lys Gly Glu
545                 550                 555
```

<210> SEQ ID NO 2
<211> LENGTH: 557
<212> TYPE: PRT
<213> ORGANISM: Escherichia coli

<400> SEQUENCE: 2

```
Met Thr Glu Ser Phe Ala Gln Leu Phe Glu Ser Leu Lys Glu Ile
 1               5                  10                  15

Glu Thr Arg Pro Gly Ser Ile Val Arg Gly Val Val Ala Ile Asp
                20                  25                  30

Lys Asp Val Val Leu Val Asp Ala Gly Leu Lys Ser Glu Ser Ala Ile
                35                  40                  45

Pro Ala Glu Gln Phe Lys Asn Ala Gln Gly Glu Leu Glu Ile Gln Val
 50                  55                  60

Gly Asp Glu Val Asp Val Ala Leu Asp Ala Val Glu Asp Gly Phe Gly
 65                  70                  75                  80

Glu Thr Leu Leu Ser Arg Glu Lys Ala Lys Arg His Glu Ala Trp Ile
                85                  90                  95

Thr Leu Glu Lys Ala Tyr Glu Asp Ala Glu Thr Val Thr Gly Val Ile
                100                 105                 110

Asn Gly Lys Val Lys Gly Gly Phe Thr Val Glu Leu Asn Gly Ile Arg
                115                 120                 125

Ala Phe Leu Pro Gly Ser Leu Val Asp Val Arg Pro Val Arg Asp Thr
 130                 135                 140

Leu His Leu Glu Gly Lys Glu Leu Glu Phe Lys Val Ile Lys Leu Asp
 145                 150                 155                 160

Gln Lys Arg Asn Asn Val Val Ser Arg Arg Ala Val Ile Glu Ser
                165                 170                 175

Glu Asn Ser Ala Glu Arg Asp Gln Leu Leu Glu Asn Leu Gln Glu Gly
                180                 185                 190

Met Glu Val Lys Gly Ile Val Lys Asn Leu Thr Asp Tyr Gly Ala Phe
                195                 200                 205

Val Asp Leu Gly Gly Val Asp Gly Leu Leu His Ile Thr Asp Met Ala
 210                 215                 220

Trp Lys Arg Val Lys His Pro Ser Glu Ile Val Asn Val Gly Asp Glu
 225                 230                 235                 240

Ile Thr Val Lys Val Leu Lys Phe Asp Arg Glu Arg Thr Arg Val Ser
                245                 250                 255

Leu Gly Leu Lys Gln Leu Gly Glu Asp Pro Trp Val Ala Ile Ala Lys
                260                 265                 270

Arg Tyr Pro Glu Gly Thr Lys Leu Thr Gly Arg Val Thr Asn Leu Thr
                275                 280                 285

Asp Tyr Gly Cys Phe Val Glu Ile Glu Glu Gly Val Glu Gly Leu Val
                290                 295                 300

His Val Ser Glu Met Asp Trp Thr Asn Lys Asn Ile His Pro Ser Lys
 305                 310                 315                 320

Val Val Asn Val Gly Asp Val Val Glu Val Met Val Leu Asp Ile Asp
                325                 330                 335

Glu Glu Arg Arg Arg Ile Ser Leu Gly Leu Lys Gln Cys Lys Ala Asn
                340                 345                 350

Pro Trp Gln Gln Phe Ala Glu Thr His Asn Lys Gly Asp Arg Val Glu
                355                 360                 365

Gly Lys Ile Lys Ser Ile Thr Asp Phe Gly Ile Phe Ile Gly Leu Asp
                370                 375                 380
```

```
Gly Gly Ile Asp Gly Leu Val His Leu Ser Asp Ile Ser Trp Asn Val
385                 390                 395                 400

Ala Gly Glu Glu Ala Val Arg Glu Tyr Lys Lys Gly Asp Glu Ile Ala
            405                 410                 415

Ala Val Val Leu Gln Val Asp Ala Glu Arg Glu Arg Ile Ser Leu Gly
        420                 425                 430

Val Lys Gln Leu Ala Glu Asp Pro Phe Asn Asn Trp Val Ala Leu Asn
    435                 440                 445

Lys Lys Gly Ala Ile Val Thr Gly Lys Val Thr Ala Val Asp Ala Lys
450                 455                 460

Gly Ala Thr Val Glu Leu Ala Asp Gly Val Glu Gly Tyr Leu Arg Ala
465                 470                 475                 480

Ser Glu Ala Ser Arg Asp Arg Val Glu Asp Ala Thr Leu Val Leu Ser
            485                 490                 495

Val Gly Asp Glu Val Glu Ala Lys Phe Thr Gly Val Asp Arg Lys Asn
        500                 505                 510

Arg Ala Ile Ser Leu Ser Val Arg Ala Lys Asp Glu Ala Asp Glu Lys
    515                 520                 525

Asp Ala Ile Ala Thr Val Asn Lys Gln Glu Asp Ala Asn Phe Ser Asn
530                 535                 540

Asn Ala Met Ala Glu Ala Phe Lys Ala Ala Lys Gly Glu
545                 550                 555

<210> SEQ ID NO 3
<211> LENGTH: 1674
<212> TYPE: DNA
<213> ORGANISM: Escherichia coli
<220> FEATURE:
<221> NAME/KEY: CDS
<222> LOCATION: (1)..(1674)

<400> SEQUENCE: 3 atg act gaa tct ttt gct caa ctc ttt gaa gag tcc tta aaa gaa atc     48
Met Thr Glu Ser Phe Ala Gln Leu Phe Glu Glu Ser Leu Lys Glu Ile
1               5                   10                  15 gaa acc cgc ccg ggt tct atc gtt cgt ggc gtt gtt gtt gct atc gac     96
Glu Thr Arg Pro Gly Ser Ile Val Arg Gly Val Val Val Ala Ile Asp
                20                  25                  30 aaa gac gta gta ctg gtt gac gct ggt ctg aaa tct gag tcc gcc atc    144
Lys Asp Val Val Leu Val Asp Ala Gly Leu Lys Ser Glu Ser Ala Ile
            35                  40                  45 ccg gct gag cag ttc aaa aac gcc cag ggc gag ctg gaa atc cag gta    192
Pro Ala Glu Gln Phe Lys Asn Ala Gln Gly Glu Leu Glu Ile Gln Val
        50                  55                  60 ggt gac gaa gtt gac gtt gct ctg gac gca gta gaa gac ggc ttc ggt    240
Gly Asp Glu Val Asp Val Ala Leu Asp Ala Val Glu Asp Gly Phe Gly
65                  70                  75                  80 gaa act ctg ctg tcc cgt gag aaa gct aaa cgt cac gaa gcc tgg atc    288
Glu Thr Leu Leu Ser Arg Glu Lys Ala Lys Arg His Glu Ala Trp Ile
                85                  90                  95 acg ctg gaa aaa gct tac gaa gat gct gaa act gtt acc ggt gtt atc    336
Thr Leu Glu Lys Ala Tyr Glu Asp Ala Glu Thr Val Thr Gly Val Ile
                100                 105                 110 aac ggc aaa gtt aag ggc ggc ttc act gtt gag ctg aac ggt att cgt    384
Asn Gly Lys Val Lys Gly Gly Phe Thr Val Glu Leu Asn Gly Ile Arg
            115                 120                 125 gcg ttc ctg cca ggt tct ctg gta gac gtt cgt ccg gtg cgt gac act    432
Ala Phe Leu Pro Gly Ser Leu Val Asp Val Arg Pro Val Arg Asp Thr
```

```
                130             135             140
ctg cac ctg gaa ggc aaa gag ctt gaa ttt aaa gta atc aag ctg gat    480
Leu His Leu Glu Gly Lys Glu Leu Glu Phe Lys Val Ile Lys Leu Asp
145                 150                 155                 160 cag aag cgc aac aac gtt gtt gtt tct cgt cgt gcc gtt atc gaa tcc    528
Gln Lys Arg Asn Asn Val Val Val Ser Arg Arg Ala Val Ile Glu Ser
                165                 170                 175 gaa aac agc gca gag cgc gat cag ctg ctg gaa aac ctg cag gaa ggc    576
Glu Asn Ser Ala Glu Arg Asp Gln Leu Leu Glu Asn Leu Gln Glu Gly
            180                 185                 190 atg gaa gtt aaa ggt atc gtt aag aac ctc act gac tac ggt gca ttc    624
Met Glu Val Lys Gly Ile Val Lys Asn Leu Thr Asp Tyr Gly Ala Phe
        195                 200                 205 gtt tat ctg ggc ggc gtt gac ggc ctg ctg cac atc act gac atg gcc    672
Val Tyr Leu Gly Gly Val Asp Gly Leu Leu His Ile Thr Asp Met Ala
    210                 215                 220 tgg aaa cgc gtt aag cat ccg agc gaa atc gtc aac gtg ggc gac gaa    720
Trp Lys Arg Val Lys His Pro Ser Glu Ile Val Asn Val Gly Asp Glu
225                 230                 235                 240 atc act gtt aaa gtg ctg aag ttc gac cgc gaa cgt acc cgt gta tcc    768
Ile Thr Val Lys Val Leu Lys Phe Asp Arg Glu Arg Thr Arg Val Ser
                245                 250                 255 ctg ggc ctg aaa cag ctg ggc gaa gat ccg tgg gta gct atc gct aaa    816
Leu Gly Leu Lys Gln Leu Gly Glu Asp Pro Trp Val Ala Ile Ala Lys
            260                 265                 270 cgt tat ccg gaa ggt acc aaa ctg act ggt cgc gtg acc aac ctg acc    864
Arg Tyr Pro Glu Gly Thr Lys Leu Thr Gly Arg Val Thr Asn Leu Thr
        275                 280                 285 gac tac ggc tgc ttc gtt gaa atc gaa gaa ggc gtt gaa ggc ctg gta    912
Asp Tyr Gly Cys Phe Val Glu Ile Glu Glu Gly Val Glu Gly Leu Val
    290                 295                 300 cac gtt tcc gaa atg gac tgg acc aac aaa aac atc cac ccg tcc aaa    960
His Val Ser Glu Met Asp Trp Thr Asn Lys Asn Ile His Pro Ser Lys
305                 310                 315                 320 gtt gtt aac gtt ggc gat gta gtg gaa gtt atg gtt ctg gat atc gac   1008
Val Val Asn Val Gly Asp Val Val Glu Val Met Val Leu Asp Ile Asp
                325                 330                 335 gaa gaa cgt cgt cgt atc tcc ctg ggt ctg aaa cag tgc aaa gct aac   1056
Glu Glu Arg Arg Arg Ile Ser Leu Gly Leu Lys Gln Cys Lys Ala Asn
            340                 345                 350 ccg tgg cag cag ttc gcg gaa acc cac aac aag ggc gac cgt gtt gaa   1104
Pro Trp Gln Gln Phe Ala Glu Thr His Asn Lys Gly Asp Arg Val Glu
        355                 360                 365 ggt aaa atc aag tct atc act gac ttc ggt atc ttc atc ggc ttg gac   1152
Gly Lys Ile Lys Ser Ile Thr Asp Phe Gly Ile Phe Ile Gly Leu Asp
    370                 375                 380 ggc ggc atc gac ggc ctg gtt cac ctg tct gac atc tcc tgg aac gtt   1200
Gly Gly Ile Asp Gly Leu Val His Leu Ser Asp Ile Ser Trp Asn Val
385                 390                 395                 400 gca ggc gaa gaa gca gtt cgt gaa tac aaa aaa ggc gac gaa atc gct   1248
Ala Gly Glu Glu Ala Val Arg Glu Tyr Lys Lys Gly Asp Glu Ile Ala
                405                 410                 415 gca gtt gtt ctg cag gtt gac gca gaa cgt gaa cgt atc tcc ctg ggc   1296
Ala Val Val Leu Gln Val Asp Ala Glu Arg Glu Arg Ile Ser Leu Gly
            420                 425                 430 gtt aaa cag ctc gca gaa gat ccg ttc aac aac tgg gtt gct ctg aac   1344
Val Lys Gln Leu Ala Glu Asp Pro Phe Asn Asn Trp Val Ala Leu Asn
        435                 440                 445 aag aaa ggc gct atc gta acc ggt aaa gta act gca gtt gac gct aaa   1392
Lys Lys Gly Ala Ile Val Thr Gly Lys Val Thr Ala Val Asp Ala Lys
```

```
Lys Lys Gly Ala Ile Val Thr Gly Lys Val Thr Ala Val Asp Ala Lys
            450                 455                 460 ggc gca acc gta gaa ctg gct gac ggc gtt gaa ggt tac ctg cgt gct      1440
Gly Ala Thr Val Glu Leu Ala Asp Gly Val Glu Gly Tyr Leu Arg Ala
465                 470                 475                 480 tct gaa gca tcc cgt gac cgc gtt gaa gac gct acc ctg gtt ctg agc      1488
Ser Glu Ala Ser Arg Asp Arg Val Glu Asp Ala Thr Leu Val Leu Ser
                485                 490                 495 gtt ggc gac gaa gtt gaa gct aaa ttc acc ggc gtt gat cgt aaa aac      1536
Val Gly Asp Glu Val Glu Ala Lys Phe Thr Gly Val Asp Arg Lys Asn
500                 505                 510 cgc gca atc agc ctg tct gtt cgt gcg aaa gac gaa gct gac gag aaa      1584
Arg Ala Ile Ser Leu Ser Val Arg Ala Lys Asp Glu Ala Asp Glu Lys
            515                 520                 525 gat gca atc gca act gtt aac aaa cag gaa gat gca aac ttc tcc aac      1632
Asp Ala Ile Ala Thr Val Asn Lys Gln Glu Asp Ala Asn Phe Ser Asn
530                 535                 540 aac gca atg gct gaa gct ttc aaa gca gct aaa ggc gag taa              1674
Asn Ala Met Ala Glu Ala Phe Lys Ala Ala Lys Gly Glu
545                 550                 555

<210> SEQ ID NO 4
<211> LENGTH: 557
<212> TYPE: PRT
<213> ORGANISM: Escherichia coli

<400> SEQUENCE: 4

Met Thr Glu Ser Phe Ala Gln Leu Phe Glu Glu Ser Leu Lys Glu Ile
1               5                   10                  15

Glu Thr Arg Pro Gly Ser Ile Val Arg Gly Val Val Val Ala Ile Asp
            20                  25                  30

Lys Asp Val Val Leu Val Asp Ala Gly Leu Lys Ser Glu Ser Ala Ile
        35                  40                  45

Pro Ala Glu Gln Phe Lys Asn Ala Gln Gly Glu Leu Glu Ile Gln Val
    50                  55                  60

Gly Asp Glu Val Asp Val Ala Leu Asp Ala Val Glu Asp Gly Phe Gly
65                  70                  75                  80

Glu Thr Leu Leu Ser Arg Glu Lys Ala Lys Arg His Glu Ala Trp Ile
                85                  90                  95

Thr Leu Glu Lys Ala Tyr Glu Asp Ala Glu Thr Val Thr Gly Val Ile
            100                 105                 110

Asn Gly Lys Val Lys Gly Gly Phe Thr Val Glu Leu Asn Gly Ile Arg
        115                 120                 125

Ala Phe Leu Pro Gly Ser Leu Val Asp Val Arg Pro Val Arg Asp Thr
    130                 135                 140

Leu His Leu Glu Gly Lys Glu Leu Glu Phe Lys Val Ile Lys Leu Asp
145                 150                 155                 160

Gln Lys Arg Asn Asn Val Val Val Ser Arg Arg Ala Val Ile Glu Ser
                165                 170                 175

Glu Asn Ser Ala Glu Arg Asp Gln Leu Leu Glu Asn Leu Gln Glu Gly
            180                 185                 190

Met Glu Val Lys Gly Ile Val Lys Asn Leu Thr Asp Tyr Gly Ala Phe
        195                 200                 205

Val Tyr Leu Gly Gly Val Asp Gly Leu Leu His Ile Thr Asp Met Ala
    210                 215                 220

Trp Lys Arg Val Lys His Pro Ser Glu Ile Val Asn Val Gly Asp Glu
225                 230                 235                 240
```

-continued

```
Ile Thr Val Lys Val Leu Lys Phe Asp Arg Glu Arg Thr Arg Val Ser
            245                 250                 255

Leu Gly Leu Lys Gln Leu Gly Glu Asp Pro Trp Val Ala Ile Ala Lys
            260                 265                 270

Arg Tyr Pro Glu Gly Thr Lys Leu Thr Gly Arg Val Thr Asn Leu Thr
            275                 280                 285

Asp Tyr Gly Cys Phe Val Glu Ile Glu Glu Gly Val Glu Gly Leu Val
            290                 295                 300

His Val Ser Glu Met Asp Trp Thr Asn Lys Asn Ile His Pro Ser Lys
305                 310                 315                 320

Val Val Asn Val Gly Asp Val Val Glu Val Met Val Leu Asp Ile Asp
                325                 330                 335

Glu Glu Arg Arg Arg Ile Ser Leu Gly Leu Lys Gln Cys Lys Ala Asn
                340                 345                 350

Pro Trp Gln Gln Phe Ala Glu Thr His Asn Lys Gly Asp Arg Val Glu
            355                 360                 365

Gly Lys Ile Lys Ser Ile Thr Asp Phe Gly Ile Phe Ile Gly Leu Asp
            370                 375                 380

Gly Gly Ile Asp Gly Leu Val His Leu Ser Asp Ile Ser Trp Asn Val
385                 390                 395                 400

Ala Gly Glu Glu Ala Val Arg Glu Tyr Lys Lys Gly Asp Glu Ile Ala
                405                 410                 415

Ala Val Val Leu Gln Val Asp Ala Glu Arg Glu Arg Ile Ser Leu Gly
            420                 425                 430

Val Lys Gln Leu Ala Glu Asp Pro Phe Asn Asn Trp Val Ala Leu Asn
            435                 440                 445

Lys Lys Gly Ala Ile Val Thr Gly Lys Val Thr Ala Val Asp Ala Lys
450                 455                 460

Gly Ala Thr Val Glu Leu Ala Asp Gly Val Glu Gly Tyr Leu Arg Ala
465                 470                 475                 480

Ser Glu Ala Ser Arg Asp Arg Val Glu Asp Ala Thr Leu Val Leu Ser
                485                 490                 495

Val Gly Asp Glu Val Glu Ala Lys Phe Thr Gly Val Asp Arg Lys Asn
            500                 505                 510

Arg Ala Ile Ser Leu Ser Val Arg Ala Lys Asp Glu Ala Asp Glu Lys
            515                 520                 525

Asp Ala Ile Ala Thr Val Asn Lys Gln Glu Asp Ala Asn Phe Ser Asn
            530                 535                 540

Asn Ala Met Ala Glu Ala Phe Lys Ala Ala Lys Gly Glu
545                 550                 555

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
attcgtttat ctgggcggcg ttgacggcct                                      30

<210> SEQ ID NO 6
<211> LENGTH: 30
<212> TYPE: DNA
<213> ORGANISM: Artificial Sequence
<220> FEATURE:
```

<223> OTHER INFORMATION: primer

<400> SEQUENCE: 6
ttactcgcct ttagctgctt tgaaagcttc                                        30

<210> SEQ ID NO 7
<211> LENGTH: 72
<212> TYPE: DNA
<213> ORGANISM: Artificial Sequence
<220> FEATURE:
<223> OTHER INFORMATION: primer

<400> SEQUENCE: 7
agacaaccgc tcaacaaagt tgcacacttt ccataaacag ggaggggtgc tctagacgct        60
caagttagta ta                                                           72

<210> SEQ ID NO 8
<211> LENGTH: 69
<212> TYPE: DNA
<213> ORGANISM: Artificial Sequence
<220> FEATURE:
<223> OTHER INFORMATION: primer

<400> SEQUENCE: 8
gttgtttgta gtgacgccag atactgtgca cgcaggctac aattcggttc agatcttgaa        60
gcctgcttt                                                               69

<210> SEQ ID NO 9
<211> LENGTH: 69
<212> TYPE: DNA
<213> ORGANISM: Artificial Sequence
<220> FEATURE:
<223> OTHER INFORMATION: primer

<400> SEQUENCE: 9
cgttattgtt atctagttgt gcaaaacatg ctaatgtagc aactaagcac ttgtctcctg        60
tttactccc                                                               69

<210> SEQ ID NO 10
<211> LENGTH: 66
<212> TYPE: DNA
<213> ORGANISM: Artificial Sequence
<220> FEATURE:
<223> OTHER INFORMATION: primer

<400> SEQUENCE: 10
attagtaaca gccataatgc tctcctgata atgttaaacc tgcttttaag acccactttc        60
acattt                                                                  66

<210> SEQ ID NO 11
<211> LENGTH: 1674
<212> TYPE: DNA
<213> ORGANISM: Pantoea ananatis
<220> FEATURE:
<221> NAME/KEY: CDS
<222> LOCATION: (1)..(1674)

<400> SEQUENCE: 11 atg act gaa tct ttt gct caa cta ttt gaa gaa tcc ctg aaa gaa atc        48
Met Thr Glu Ser Phe Ala Gln Leu Phe Glu Glu Ser Leu Lys Glu Ile
1               5                   10                  15 gaa acc cgc ccg ggt tcc atc gtt cgt ggc gtc gtt gtc tct atc gac        96
Glu Thr Arg Pro Gly Ser Ile Val Arg Gly Val Val Val Ser Ile Asp

```
                 20                  25                  30
aaa gac gtc gtt ctg gtt gat gcg ggc ctg aaa tct gaa tct gca att    144
Lys Asp Val Val Leu Val Asp Ala Gly Leu Lys Ser Glu Ser Ala Ile
             35                  40                  45 cct gca gag cag ttc aaa aac gca gcc ggc gaa ctg gaa atc cag gtt    192
Pro Ala Glu Gln Phe Lys Asn Ala Ala Gly Glu Leu Glu Ile Gln Val
 50                  55                  60 ggt gac gaa gtt gac gtt gct ctg gac gca gtg gaa gac ggc ttc ggt    240
Gly Asp Glu Val Asp Val Ala Leu Asp Ala Val Glu Asp Gly Phe Gly
 65                  70                  75                  80 gaa act ctg ctg tcc cgt gag aaa gct aag cgt cat gaa gct tgg atc    288
Glu Thr Leu Leu Ser Arg Glu Lys Ala Lys Arg His Glu Ala Trp Ile
                 85                  90                  95 acg ctg gaa aaa gct tac gaa gaa gct gaa act gtt acc ggt att atc    336
Thr Leu Glu Lys Ala Tyr Glu Glu Ala Glu Thr Val Thr Gly Ile Ile
            100                 105                 110 aac ggc aaa gtc aaa ggt ggc ttc aca gtt gag ctg aac ggt atc cgt    384
Asn Gly Lys Val Lys Gly Gly Phe Thr Val Glu Leu Asn Gly Ile Arg
        115                 120                 125 gcg ttc ctg cca ggt tca ctg gta gat gtg cgt cca gtg cgt gac acg    432
Ala Phe Leu Pro Gly Ser Leu Val Asp Val Arg Pro Val Arg Asp Thr
    130                 135                 140 ctg cac ctg gaa ggc aaa gag ctt gaa ttc aaa gtg atc aag ctg gat    480
Leu His Leu Glu Gly Lys Glu Leu Glu Phe Lys Val Ile Lys Leu Asp
145                 150                 155                 160 cag aaa cgc aac aac gtc gtg gtt tca cgt cgt gcg gtt atc gaa tct    528
Gln Lys Arg Asn Asn Val Val Val Ser Arg Arg Ala Val Ile Glu Ser
                165                 170                 175 gag aac agt gca gag cgc gat cag ctg ctg gaa aac ctg cag gaa ggc    576
Glu Asn Ser Ala Glu Arg Asp Gln Leu Leu Glu Asn Leu Gln Glu Gly
            180                 185                 190 atg gaa gtc aaa ggt atc gtt aag aac ctg act gac tac ggt gcg ttc    624
Met Glu Val Lys Gly Ile Val Lys Asn Leu Thr Asp Tyr Gly Ala Phe
        195                 200                 205 gtt gat ctg ggc ggc gtt gac ggc ctg ctg cac atc act gat atg gcc    672
Val Asp Leu Gly Gly Val Asp Gly Leu Leu His Ile Thr Asp Met Ala
    210                 215                 220 tgg aag cgc gtt aag cat cca agc gag atc gtg aat gtt ggc gat gaa    720
Trp Lys Arg Val Lys His Pro Ser Glu Ile Val Asn Val Gly Asp Glu
225                 230                 235                 240 atc aac gtt aaa gtc ctg aaa ttc gac cgc gag cgt acc cgt gta tct    768
Ile Asn Val Lys Val Leu Lys Phe Asp Arg Glu Arg Thr Arg Val Ser
                245                 250                 255 ctg ggt ctg aag cag ctg ggc gaa gat cca tgg gtg gct atc gct aag    816
Leu Gly Leu Lys Gln Leu Gly Glu Asp Pro Trp Val Ala Ile Ala Lys
            260                 265                 270 cgc tat cca gaa ggc acc aag ctg act ggt cgt gtg acc aac ctg act    864
Arg Tyr Pro Glu Gly Thr Lys Leu Thr Gly Arg Val Thr Asn Leu Thr
        275                 280                 285 gat tac ggc tgc ttc gta gaa atc gaa gaa ggc gtt gaa ggt ctg gta    912
Asp Tyr Gly Cys Phe Val Glu Ile Glu Glu Gly Val Glu Gly Leu Val
    290                 295                 300 cac gtt tca gaa atg gac tgg acc aac aaa aac atc cat ccg tct aaa    960
His Val Ser Glu Met Asp Trp Thr Asn Lys Asn Ile His Pro Ser Lys
305                 310                 315                 320 gtt gtt aac gta ggc gat gtg gtt gaa gta atg gtt ctg gac atc gat   1008
Val Val Asn Val Gly Asp Val Val Glu Val Met Val Leu Asp Ile Asp
                325                 330                 335 gaa gag cgt cgt cgt atc tcc ctg ggt ctg aag cag tgt aaa tct aac   1056
```

```
Glu Glu Arg Arg Arg Ile Ser Leu Gly Leu Lys Gln Cys Lys Ser Asn
            340                 345                 350 cca tgg cag cag ttc gcc gag act cac aat aaa ggc gat cgc gtt gaa      1104
Pro Trp Gln Gln Phe Ala Glu Thr His Asn Lys Gly Asp Arg Val Glu
        355                 360                 365 ggt aaa atc aag tca atc act gac ttc ggt atc ttc atc ggc ctg gac      1152
Gly Lys Ile Lys Ser Ile Thr Asp Phe Gly Ile Phe Ile Gly Leu Asp
370                 375                 380 ggc ggc atc gac ggt ctg gtt cac ctg tct gac atc tcc tgg aac gcg      1200
Gly Gly Ile Asp Gly Leu Val His Leu Ser Asp Ile Ser Trp Asn Ala
385                 390                 395                 400 act ggc gaa gaa gcc gtt cgt gag tac aaa aaa ggt gac gaa atc gct      1248
Thr Gly Glu Glu Ala Val Arg Glu Tyr Lys Lys Gly Asp Glu Ile Ala
            405                 410                 415 gcc gtt gta ctg cag gtt gat gca gag cgc gag cgt atc tct ctg ggc      1296
Ala Val Val Leu Gln Val Asp Ala Glu Arg Glu Arg Ile Ser Leu Gly
        420                 425                 430 gtt aaa cag ctg gca gaa gat ccg ttc aac aac tac atc act ttg aac      1344
Val Lys Gln Leu Ala Glu Asp Pro Phe Asn Asn Tyr Ile Thr Leu Asn
    435                 440                 445 aag aaa ggt gcc atc gtc acc ggt aaa gtg act gca gtt gat gct aaa      1392
Lys Lys Gly Ala Ile Val Thr Gly Lys Val Thr Ala Val Asp Ala Lys
450                 455                 460 ggt gct aca gtt gaa tta gca gac ggc gtt gaa ggt tac ctg cgc gct      1440
Gly Ala Thr Val Glu Leu Ala Asp Gly Val Glu Gly Tyr Leu Arg Ala
465                 470                 475                 480 tct gaa gct tca ctg gac cgc atc gaa gac gct acg ctg gtt ctg aac      1488
Ser Glu Ala Ser Leu Asp Arg Ile Glu Asp Ala Thr Leu Val Leu Asn
            485                 490                 495 gta ggc gac gac gtt gaa gct aaa ttc acc ggc gtt gac cgt aaa aac      1536
Val Gly Asp Asp Val Glu Ala Lys Phe Thr Gly Val Asp Arg Lys Asn
        500                 505                 510 cgc gtt gtt agc ctg tct gtt cgt gcg aaa gac cag gct gac gag aaa      1584
Arg Val Val Ser Leu Ser Val Arg Ala Lys Asp Gln Ala Asp Glu Lys
    515                 520                 525 gaa gcc atc aat act gtt aac acc aaa cag gaa gaa ggc aac ttc tct      1632
Glu Ala Ile Asn Thr Val Asn Thr Lys Gln Glu Glu Gly Asn Phe Ser
530                 535                 540 agc gct atg gct gaa gcg ttc aaa gcg gct aaa ggc gag taa              1674
Ser Ala Met Ala Glu Ala Phe Lys Ala Ala Lys Gly Glu
545                 550                 555

<210> SEQ ID NO 12
<211> LENGTH: 557
<212> TYPE: PRT
<213> ORGANISM: Pantoea ananatis

<400> SEQUENCE: 12

Met Thr Glu Ser Phe Ala Gln Leu Phe Glu Gl

-continued

```
                    85                  90                  95
Thr Leu Glu Lys Ala Tyr Glu Ala Glu Thr Val Thr Gly Ile Ile
                100                 105                 110
Asn Gly Lys Val Lys Gly Gly Phe Thr Val Glu Leu Asn Gly Ile Arg
        115                 120                 125
Ala Phe Leu Pro Gly Ser Leu Val Asp Val Arg Pro Val Arg Asp Thr
    130                 135                 140
Leu His Leu Glu Gly Lys Glu Leu Glu Phe Lys Val Ile Lys Leu Asp
145                 150                 155                 160
Gln Lys Arg Asn Asn Val Val Ser Arg Arg Ala Val Ile Glu Ser
                165                 170                 175
Glu Asn Ser Ala Glu Arg Asp Gln Leu Leu Glu Asn Leu Gln Glu Gly
            180                 185                 190
Met Glu Val Lys Gly Ile Val Lys Asn Leu Thr Asp Tyr Gly Ala Phe
        195                 200                 205
Val Asp Leu Gly Gly Val Asp Gly Leu Leu His Ile Thr Asp Met Ala
    210                 215                 220
Trp Lys Arg Val Lys His Pro Ser Glu Ile Val Asn Val Gly Asp Glu
225                 230                 235                 240
Ile Asn Val Lys Val Leu Lys Phe Asp Arg Glu Arg Thr Arg Val Ser
                245                 250                 255
Leu Gly Leu Lys Gln Leu Gly Glu Asp Pro Trp Val Ala Ile Ala Lys
            260                 265                 270
Arg Tyr Pro Glu Gly Thr Lys Leu Thr Gly Arg Val Thr Asn Leu Thr
        275                 280                 285
Asp Tyr Gly Cys Phe Val Glu Ile Glu Glu Gly Val Glu Gly Leu Val
    290                 295                 300
His Val Ser Glu Met Asp Trp Thr Asn Lys Asn Ile His Pro Ser Lys
305                 310                 315                 320
Val Val Asn Val Gly Asp Val Val Glu Val Met Val Leu Asp Ile Asp
                325                 330                 335
Glu Glu Arg Arg Arg Ile Ser Leu Gly Leu Lys Gln Cys Lys Ser Asn
            340                 345                 350
Pro Trp Gln Gln Phe Ala Glu Thr His Asn Lys Gly Asp Arg Val Glu
        355                 360                 365
Gly Lys Ile Lys Ser Ile Thr Asp Phe Gly Ile Phe Ile Gly Leu Asp
    370                 375                 380
Gly Gly Ile Asp Gly Leu Val His Leu Ser Asp Ile Ser Trp Asn Ala
385                 390                 395                 400
Thr Gly Glu Glu Ala Val Arg Glu Tyr Lys Lys Gly Asp Glu Ile Ala
                405                 410                 415
Ala Val Val Leu Gln Val Asp Ala Glu Arg Glu Arg Ile Ser Leu Gly
            420                 425                 430
Val Lys Gln Leu Ala Glu Asp Pro Phe Asn Asn Tyr Ile Thr Leu Asn
        435                 440                 445
Lys Lys Gly Ala Ile Val Thr Gly Lys Val Thr Ala Val Asp Ala Lys
    450                 455                 460
Gly Ala Thr Val Glu Leu Ala Asp Gly Val Glu Gly Tyr Leu Arg Ala
465                 470                 475                 480
Ser Glu Ala Ser Leu Asp Arg Ile Glu Asp Ala Thr Leu Val Leu Asn
                485                 490                 495
Val Gly Asp Asp Val Glu Ala Lys Phe Thr Gly Val Asp Arg Lys Asn
            500                 505                 510
```

```
Arg Val Val Ser Leu Ser Val Arg Ala Lys Asp Gln Ala Asp Glu Lys
        515                 520                 525

Glu Ala Ile Asn Thr Val Asn Thr Lys Gln Glu Gly Asn Phe Ser
530                 535                 540

Ser Ala Met Ala Glu Ala Phe Lys Ala Ala Lys Gly Glu
545                 550                 555

<210> SEQ ID NO 13
<211> LENGTH: 1674
<212> TYPE: DNA
<213> ORGANISM: Enterobacter aerogenes
<220> FEATURE:
<221> NAME/KEY: CDS
<222> LOCATION: (1)..(1674)

<400> SEQUENCE: 13 atg act gaa tct ttt gct caa cta ttt gaa gaa tcc tta aaa gaa atc      48
Met Thr Glu Ser Phe Ala Gln Leu Phe Glu Glu Ser Leu Lys Glu Ile
1               5                   10                  15 gaa acc cgc ccg ggt tcc atc gtt cgt ggt gtt gtt gtt gct atc gac      96
Glu Thr Arg Pro Gly Ser Ile Val Arg Gly Val Val Val Ala Ile Asp
                20                  25                  30 aaa gat atc gta ctg gtt gac gct ggt ctg aaa tct gag tcc gcc atc     144
Lys Asp Ile Val Leu Val Asp Ala Gly Leu Lys Ser Glu Ser Ala Ile
            35                  40                  45 ccg gct gag cag ttc aaa aac gcc cag ggc gag ctg gaa atc cag gtt     192
Pro Ala Glu Gln Phe Lys Asn Ala Gln Gly Glu Leu Glu Ile Gln Val
        50                  55                  60 ggt gac gaa gtt gac gtt gct ctg gat gca gta gaa gac ggc ttc ggt     240
Gly Asp Glu Val Asp Val Ala Leu Asp Ala Val Glu Asp Gly Phe Gly
65                  70                  75                  80 gaa acc ctg ctg tcc cgt gag aaa gct aaa cgt cac gaa gct tgg atc     288
Glu Thr Leu Leu Ser Arg Glu Lys Ala Lys Arg His Glu Ala Trp Ile
                85                  90                  95 acg ctg gaa aaa gct tac gaa gac gct gaa act gta gtc ggt gtt atc     336
Thr Leu Glu Lys Ala Tyr Glu Asp Ala Glu Thr Val Val Gly Val Ile
                100                 105                 110 aac ggc aaa gtt aaa ggt ggc ttc act gtt gag ctg aat ggt att cgt     384
Asn Gly Lys Val Lys Gly Gly Phe Thr Val Glu Leu Asn Gly Ile Arg
            115                 120                 125 gcg ttc ctg ccg ggt tcc ctg gta gac gtt cgt ccg gtg cgc gac acg     432
Ala Phe Leu Pro Gly Ser Leu Val Asp Val Arg Pro Val Arg Asp Thr
        130                 135                 140 ctg cac ctg gaa ggc aaa gag ctt gaa ttc aaa gtc atc aag ctg gac     480
Leu His Leu Glu Gly Lys Glu Leu Glu Phe Lys Val Ile Lys Leu Asp
145                 150                 155                 160 cag aaa cgt aac aac gtc gtt gtt tct cgt cgt gcc gtt atc gaa tcc     528
Gln Lys Arg Asn Asn Val Val Val Ser Arg Arg Ala Val Ile Glu Ser
                165                 170                 175 gaa aac agc gca gag cgc gat cag ctg ctg gaa aac ctg cag gaa ggc     576
Glu Asn Ser Ala Glu Arg Asp Gln Leu Leu Glu Asn Leu Gln Glu Gly
                180                 185                 190 atg gaa gtc aaa ggt atc gtt aag aac ctc act gac tac ggt gca ttc     624
Met Glu Val Lys Gly Ile Val Lys Asn Leu Thr Asp Tyr Gly Ala Phe
            195                 200                 205 gtt gat ctg ggc ggc gtt gac ggc ctg ctg cac atc acc gat atg gcc     672
Val Asp Leu Gly Gly Val Asp Gly Leu Leu His Ile Thr Asp Met Ala
        210                 215                 220 tgg aaa cgc gtt aag cat ccg agc gaa atc gta aac gtt ggc gac gaa     720
Trp Lys Arg Val Lys His Pro Ser Glu Ile Val Asn Val Gly Asp Glu
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 225 |     |     |     |     | 230 |     |     |     |     | 235 |     |     |     |     | 240 |      |
| atc | act | gtt | aaa | gtg | ctg | aag | ttc | gac | cgc | gag | cgt | acc | cgt | gta | tcc | 768  |
| Ile | Thr | Val | Lys | Val | Leu | Lys | Phe | Asp | Arg | Glu | Arg | Thr | Arg | Val | Ser |      |
|     |     |     |     | 245 |     |     |     |     | 250 |     |     |     |     | 255 |     |      |
| ctg | ggc | ctg | aaa | cag | ctg | ggc | gaa | gat | ccg | tgg | gta | gct | atc | gct | aag | 816  |
| Leu | Gly | Leu | Lys | Gln | Leu | Gly | Glu | Asp | Pro | Trp | Val | Ala | Ile | Ala | Lys |      |
|     |     |     |     | 260 |     |     |     |     | 265 |     |     |     |     | 270 |     |      |
| cgt | tat | ccg | gaa | ggt | acc | aaa | ctg | acc | ggt | cgc | gtg | acc | aac | ctg | acc | 864  |
| Arg | Tyr | Pro | Glu | Gly | Thr | Lys | Leu | Thr | Gly | Arg | Val | Thr | Asn | Leu | Thr |      |
|     |     |     |     | 275 |     |     |     |     | 280 |     |     |     |     | 285 |     |      |
| gac | tac | ggc | tgc | ttc | gtt | gaa | atc | gaa | gaa | ggc | gtt | gaa | ggc | ctg | gtt | 912  |
| Asp | Tyr | Gly | Cys | Phe | Val | Glu | Ile | Glu | Glu | Gly | Val | Glu | Gly | Leu | Val |      |
|     |     |     |     | 290 |     |     |     |     | 295 |     |     |     |     | 300 |     |      |
| cac | gtt | tcc | gaa | atg | gat | tgg | acc | aac | aaa | aac | atc | cac | ccg | tcc | aaa | 960  |
| His | Val | Ser | Glu | Met | Asp | Trp | Thr | Asn | Lys | Asn | Ile | His | Pro | Ser | Lys |      |
| 305 |     |     |     |     | 310 |     |     |     |     | 315 |     |     |     |     | 320 |      |
| gtt | gtt | aac | gtt | ggc | gat | gta | gtg | gaa | gtt | atg | gtt | ctg | gat | atc | gac | 1008 |
| Val | Val | Asn | Val | Gly | Asp | Val | Val | Glu | Val | Met | Val | Leu | Asp | Ile | Asp |      |
|     |     |     |     | 325 |     |     |     |     | 330 |     |     |     |     | 335 |     |      |
| gaa | gaa | cgt | cgt | cgt | atc | tcc | ctg | ggt | ctg | aag | cag | tgc | aaa | tct | aac | 1056 |
| Glu | Glu | Arg | Arg | Arg | Ile | Ser | Leu | Gly | Leu | Lys | Gln | Cys | Lys | Ser | Asn |      |
|     |     |     |     | 340 |     |     |     |     | 345 |     |     |     |     | 350 |     |      |
| cca | tgg | cag | cag | ttc | gcg | gaa | acc | cac | aac | aag | ggc | gac | cgt | gtt | gaa | 1104 |
| Pro | Trp | Gln | Gln | Phe | Ala | Glu | Thr | His | Asn | Lys | Gly | Asp | Arg | Val | Glu |      |
|     |     |     |     | 355 |     |     |     |     | 360 |     |     |     |     | 365 |     |      |
| ggt | aaa | atc | aag | tct | atc | act | gac | ttc | ggt | atc | ttc | atc | ggc | ctg | gac | 1152 |
| Gly | Lys | Ile | Lys | Ser | Ile | Thr | Asp | Phe | Gly | Ile | Phe | Ile | Gly | Leu | Asp |      |
|     |     |     |     | 370 |     |     |     |     | 375 |     |     |     |     | 380 |     |      |
| ggc | ggc | atc | gac | ggc | ctg | gtt | cac | ctg | tct | gac | atc | tcc | tgg | aac | gtt | 1200 |
| Gly | Gly | Ile | Asp | Gly | Leu | Val | His | Leu | Ser | Asp | Ile | Ser | Trp | Asn | Val |      |
| 385 |     |     |     |     | 390 |     |     |     |     | 395 |     |     |     |     | 400 |      |
| gca | ggc | gaa | gaa | gca | gtt | cgt | gaa | tac | aaa | aaa | ggc | gac | gaa | atc | gct | 1248 |
| Ala | Gly | Glu | Glu | Ala | Val | Arg | Glu | Tyr | Lys | Lys | Gly | Asp | Glu | Ile | Ala |      |
|     |     |     |     | 405 |     |     |     |     | 410 |     |     |     |     | 415 |     |      |
| gca | gtt | gta | ctg | cag | gtt | gac | gca | gaa | cgt | gag | cgt | atc | tcc | ctg | ggc | 1296 |
| Ala | Val | Val | Leu | Gln | Val | Asp | Ala | Glu | Arg | Glu | Arg | Ile | Ser | Leu | Gly |      |
|     |     |     |     | 420 |     |     |     |     | 425 |     |     |     |     | 430 |     |      |
| gtt | aaa | cag | ctg | gcg | gaa | gat | ccg | ttc | aac | aac | tac | gtt | gct | ctg | aac | 1344 |
| Val | Lys | Gln | Leu | Ala | Glu | Asp | Pro | Phe | Asn | Asn | Tyr | Val | Ala | Leu | Asn |      |
|     |     |     |     | 435 |     |     |     |     | 440 |     |     |     |     | 445 |     |      |
| aag | aaa | ggc | gct | atc | gta | acc | ggt | aaa | gta | act | gca | gtt | gat | gct | aaa | 1392 |
| Lys | Lys | Gly | Ala | Ile | Val | Thr | Gly | Lys | Val | Thr | Ala | Val | Asp | Ala | Lys |      |
|     |     |     |     | 450 |     |     |     |     | 455 |     |     |     |     | 460 |     |      |
| ggc | gca | acc | gta | gaa | ctg | gct | gac | ggc | gtt | gaa | ggt | tac | ctg | cgt | gct | 1440 |
| Gly | Ala | Thr | Val | Glu | Leu | Ala | Asp | Gly | Val | Glu | Gly | Tyr | Leu | Arg | Ala |      |
| 465 |     |     |     |     | 470 |     |     |     |     | 475 |     |     |     |     | 480 |      |
| tct | gaa | gca | tcc | cgt | gac | cgc | gtt | gaa | gat | gca | act | ctg | gtt | ctg | agc | 1488 |
| Ser | Glu | Ala | Ser | Arg | Asp | Arg | Val | Glu | Asp | Ala | Thr | Leu | Val | Leu | Ser |      |
|     |     |     |     | 485 |     |     |     |     | 490 |     |     |     |     | 495 |     |      |
| gtt | ggc | gac | gaa | gtt | gaa | gct | aaa | ttc | acc | ggc | gtt | gat | cgt | aaa | aac | 1536 |
| Val | Gly | Asp | Glu | Val | Glu | Ala | Lys | Phe | Thr | Gly | Val | Asp | Arg | Lys | Asn |      |
|     |     |     |     | 500 |     |     |     |     | 505 |     |     |     |     | 510 |     |      |
| cgc | gca | atc | agc | ctt | tct | gtt | cgt | gcg | aaa | gac | gaa | gct | gac | gag | aaa | 1584 |
| Arg | Ala | Ile | Ser | Leu | Ser | Val | Arg | Ala | Lys | Asp | Glu | Ala | Asp | Glu | Lys |      |
|     |     |     |     | 515 |     |     |     |     | 520 |     |     |     |     | 525 |     |      |
| gat | gca | atc | gca | act | gtt | aac | aaa | cag | gaa | gat | gca | aac | ttc | tct | aac | 1632 |
| Asp | Ala | Ile | Ala | Thr | Val | Asn | Lys | Gln | Glu | Asp | Ala | Asn | Phe | Ser | Asn |      |
|     |     |     |     | 530 |     |     |     |     | 535 |     |     |     |     | 540 |     |      |
| aac | gca | atg | gct | gaa | gct | ttc | aaa | gca | gct | aaa | ggc | gag | taa |     |     | 1674 |

Asn Ala Met Ala Glu Ala Phe Lys Ala Ala Lys Gly Glu
545                 550                 555

<210> SEQ ID NO 14
<211> LENGTH: 557
<212> TYPE: PRT
<213> ORGANISM: Enterobacter aerogenes

<400> SEQUENCE: 14

Met Thr Glu Ser Phe Ala Gln Leu Phe Glu Ser Leu Lys Glu Ile
1               5                   10                  15

Glu Thr Arg Pro Gly Ser Ile Val Arg Gly Val Val Ala Ile Asp
                20                  25                  30

Lys Asp Ile Val Leu Val Asp Ala Gly Leu Lys Ser Glu Ser Ala Ile
            35                  40                  45

Pro Ala Glu Gln Phe Lys Asn Ala Gln Gly Glu Leu Glu Ile Gln Val
        50                  55                  60

Gly Asp Glu Val Asp Val Ala Leu Asp Ala Val Glu Asp Gly Phe Gly
65                  70                  75                  80

Glu Thr Leu Leu Ser Arg Glu Lys Ala Lys Arg His Glu Ala Trp Ile
                85                  90                  95

Thr Leu Glu Lys Ala Tyr Glu Asp Ala Glu Thr Val Val Gly Val Ile
                100                 105                 110

Asn Gly Lys Val Lys Gly Gly Phe Thr Val Glu Leu Asn Gly Ile Arg
            115                 120                 125

Ala Phe Leu Pro Gly Ser Leu Val Asp Val Arg Pro Val Arg Asp Thr
        130                 135                 140

Leu His Leu Glu Gly Lys Glu Leu Glu Phe Lys Val Ile Lys Leu Asp
145                 150                 155                 160

Gln Lys Arg Asn Asn Val Val Ser Arg Arg Ala Val Ile Glu Ser
                165                 170                 175

Glu Asn Ser Ala Glu Arg Asp Gln Leu Leu Glu Asn Leu Gln Glu Gly
            180                 185                 190

Met Glu Val Lys Gly Ile Val Lys Asn Leu Thr Asp Tyr Gly Ala Phe
        195                 200                 205

Val Asp Leu Gly Gly Val Asp Gly Leu Leu His Ile Thr Asp Met Ala
    210                 215                 220

Trp Lys Arg Val Lys His Pro Ser Glu Ile Val Asn Val Gly Asp Glu
225                 230                 235                 240

Ile Thr Val Lys Val Leu Lys Phe Asp Arg Glu Arg Thr Arg Val Ser
                245                 250                 255

Leu Gly Leu Lys Gln Leu Gly Glu Asp Pro Trp Val Ala Ile Ala Lys
            260                 265                 270

Arg Tyr Pro Glu Gly Thr Lys Leu Thr Gly Arg Val Thr Asn Leu Thr
        275                 280                 285

Asp Tyr Gly Cys Phe Val Glu Ile Glu Glu Gly Val Glu Gly Leu Val
    290                 295                 300

His Val Ser Glu Met Asp Trp Thr Asn Lys Asn Ile His Pro Ser Lys
305                 310                 315                 320

Val Val Asn Val Gly Asp Val Val Glu Val Met Val Leu Asp Ile Asp
                325                 330                 335

Glu Glu Arg Arg Arg Ile Ser Leu Gly Leu Lys Gln Cys Lys Ser Asn
            340                 345                 350

Pro Trp Gln Gln Phe Ala Glu Thr His Asn Lys Gly Asp Arg Val Glu
        355                 360                 365

```
Gly Lys Ile Lys Ser Ile Thr Asp Phe Gly Ile Phe Ile Gly Leu Asp
    370                 375                 380
Gly Gly Ile Asp Gly Leu Val His Leu Ser Asp Ile Ser Trp Asn Val
385                 390                 395                 400
Ala Gly Glu Glu Ala Val Arg Glu Tyr Lys Lys Gly Asp Glu Ile Ala
                405                 410                 415
Ala Val Val Leu Gln Val Asp Ala Glu Arg Glu Arg Ile Ser Leu Gly
            420                 425                 430
Val Lys Gln Leu Ala Glu Asp Pro Phe Asn Asn Tyr Val Ala Leu Asn
        435                 440                 445
Lys Lys Gly Ala Ile Val Thr Gly Lys Val Thr Ala Val Asp Ala Lys
    450                 455                 460
Gly Ala Thr Val Glu Leu Ala Asp Gly Val Glu Gly Tyr Leu Arg Ala
465                 470                 475                 480
Ser Glu Ala Ser Arg Asp Arg Val Glu Asp Ala Thr Leu Val Leu Ser
                485                 490                 495
Val Gly Asp Glu Val Glu Ala Lys Phe Thr Gly Val Asp Arg Lys Asn
            500                 505                 510
Arg Ala Ile Ser Leu Ser Val Arg Ala Lys Asp Glu Ala Asp Glu Lys
        515                 520                 525
Asp Ala Ile Ala Thr Val Asn Lys Gln Glu Asp Ala Asn Phe Ser Asn
    530                 535                 540
Asn Ala Met Ala Glu Ala Phe Lys Ala Ala Lys Gly Glu
545                 550                 555

<210> SEQ ID NO 15
<211> LENGTH: 8
<212> TYPE: PRT
<213> ORGANISM: Artificial Sequence
<220> FEATURE:
<223> OTHER INFORMATION: consensus

<400> SEQUENCE: 15

Gly Ala Phe Val Asp Leu Gly Gly
1               5

<210> SEQ ID NO 16
<211> LENGTH: 11
<212> TYPE: PRT
<213> ORGANISM: Artificial Sequence
<220> FEATURE:
<223> OTHER INFORMATION: consensus

<400> SEQUENCE: 16

Gly Ala Phe Val Asp Leu Gly Gly Val Asp Gly
1               5                   10

<210> SEQ ID NO 17
<211> LENGTH: 557
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
```

```
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (351)..(351)
<223> OTHER INFORMATION: Xaa can be any naturally occurring amino acid
<220> FEATURE:
<221> NAME/KEY: misc_feature
<222> LOCATION: (400)..(401)
<223> OTHER INFORMATION: Xaa can be any naturally occurring amino acid
<220> FEATURE:
<221> NAME/KEY: misc_feature
<222> LOCATION: (444)..(446)
<223> OTHER INFORMATION: Xaa can be any naturally occurring amino acid
<220> FEATURE:
<221> NAME/KEY: misc_feature
<222> LOCATION: (485)..(485)
<223> OTHER INFORMATION: Xaa can be any naturally occurring amino acid
<220> FEATURE:
<221> NAME/KEY: misc_feature
<222> LOCATION: (488)..(488)
<223> OTHER INFORMATION: Xaa can be any naturally occurring amino acid
<220> FEATURE:
<221> NAME/KEY: misc_feature
<222> LOCATION: (496)..(496)
<223> OTHER INFORMATION: Xaa can be any naturally occurring amino acid
<220> FEATURE:
<221> NAME/KEY: misc_feature
<222> LOCATION: (500)..(500)
<223> OTHER INFORMATION: Xaa can be any naturally occurring amino acid
<220> FEATURE:
<221> NAME/KEY: misc_feature
<222> LOCATION: (514)..(515)
<223> OTHER INFORMATION: Xaa can be any naturally occurring amino acid
<220> FEATURE:
<221> NAME/KEY: misc_feature
<222> LOCATION: (524)..(524)
<223> OTHER INFORMATION: Xaa can be any naturally occurring amino acid
<220> FEATURE:
<221> NAME/KEY: misc_feature
<222> LOCATION: (529)..(529)
<223> OTHER INFORMATION: Xaa can be any naturally occurring amino acid
<220> FEATURE:
<221> NAME/KEY: misc_feature
<222> LOCATION: (532)..(532)
<223> OTHER INFORMATION: Xaa can be any naturally occurring amino acid
<220> FEATURE:
<221> NAME/KEY: misc_feature
<222> LOCATION: (536)..(545)
<223> OTHER INFORMATION: Xaa can be any naturally occurring amino acid

<400> SEQUENCE: 17

Met Thr Glu Ser Phe Ala Gln Leu Phe Glu Glu Ser Leu Lys Glu Ile
 1               5                  10                  15

Glu Thr Arg Pro Gly Ser Ile Val Arg Gly Val Val Val Xaa Ile Asp
                20                  25                  30

Lys Asp Xaa Val Leu Val Asp Ala Gly Leu Lys Ser Glu Ser Ala Ile
                35                  40                  45
```

```
Pro Ala Glu Gln Phe Lys Asn Ala Xaa Gly Glu Leu Glu Ile Gln Val
    50                  55                  60
Gly Asp Glu Val Asp Val Ala Leu Asp Ala Val Glu Asp Gly Phe Gly
 65                  70                  75                  80
Glu Thr Leu Leu Ser Arg Glu Lys Ala Lys Arg His Glu Ala Trp Ile
                 85                  90                  95
Thr Leu Glu Lys Ala Tyr Glu Xaa Ala Glu Thr Val Xaa Gly Xaa Ile
            100                 105                 110
Asn Gly Lys Val Lys Gly Gly Phe Thr Val Glu Leu Asn Gly Ile Arg
            115                 120                 125
Ala Phe Leu Pro Gly Ser Leu Val Asp Val Arg Pro Val Arg Asp Thr
130                 135                 140
Leu His Leu Glu Gly Lys Glu Leu Glu Phe Lys Val Ile Lys Leu Asp
145                 150                 155                 160
Gln Lys Arg Asn Asn Val Val Ser Arg Arg Ala Val Ile Glu Ser
            165                 170                 175
Glu Asn Ser Ala Glu Arg Asp Gln Leu Leu Glu Asn Leu Gln Glu Gly
            180                 185                 190
Met Glu Val Lys Gly Ile Val Lys Asn Leu Thr Asp Tyr Gly Ala Phe
            195                 200                 205
Val Asp Leu Gly Gly Val Asp Gly Leu Leu His Ile Thr Asp Met Ala
210                 215                 220
Trp Lys Arg Val Lys His Pro Ser Glu Ile Val Asn Val Gly Asp Glu
225                 230                 235                 240
Ile Xaa Val Lys Val Leu Lys Phe Asp Arg Glu Arg Thr Arg Val Ser
            245                 250                 255
Leu Gly Leu Lys Gln Leu Gly Glu Asp Pro Trp Val Ala Ile Ala Lys
            260                 265                 270
Arg Tyr Pro Glu Gly Thr Lys Leu Thr Gly Arg Val Thr Asn Leu Thr
            275                 280                 285
Asp Tyr Gly Cys Phe Val Glu Ile Glu Glu Gly Val Glu Gly Leu Val
            290                 295                 300
His Val Ser Glu Met Asp Trp Thr Asn Lys Asn Ile His Pro Ser Lys
305                 310                 315                 320
Val Val Asn Val Gly Asp Val Val Glu Val Met Val Leu Asp Ile Asp
            325                 330                 335
Glu Glu Arg Arg Arg Ile Ser Leu Gly Leu Lys Gln Cys Lys Xaa Asn
            340                 345                 350
Pro Trp Gln Gln Phe Ala Glu Thr His Asn Lys Gly Asp Arg Val Glu
            355                 360                 365
Gly Lys Ile Lys Ser Ile Thr Asp Phe Gly Ile Phe Ile Gly Leu Asp
            370                 375                 380
Gly Gly Ile Asp Gly Leu Val His Leu Ser Asp Ile Ser Trp Asn Xaa
385                 390                 395                 400
Xaa Gly Glu Glu Ala Val Arg Glu Tyr Lys Lys Gly Asp Glu Ile Ala
            405                 410                 415
Ala Val Val Leu Gln Val Asp Ala Glu Arg Glu Arg Ile Ser Leu Gly
            420                 425                 430
Val Lys Gln Leu Ala Glu Asp Pro Phe Asn Asn Xaa Xaa Xaa Leu Asn
            435                 440                 445
Lys Lys Gly Ala Ile Val Thr Gly Lys Val Thr Ala Val Asp Ala Lys
450                 455                 460
Gly Ala Thr Val Glu Leu Ala Asp Gly Val Glu Gly Tyr Leu Arg Ala
```

```
                465                 470                 475                 480
Ser Glu Ala Ser Xaa Asp Arg Xaa Glu Asp Ala Thr Leu Val Leu Xaa
                485                 490                 495

Val Gly Asp Xaa Val Glu Ala Lys Phe Thr Gly Val Asp Arg Lys Asn
                500                 505                 510

Arg Xaa Xaa Ser Leu Ser Val Arg Ala Lys Asp Xaa Ala Asp Glu Lys
            515                 520                 525

Xaa Ala Ile Xaa Thr Val Asn Xaa Xaa Xaa Xaa Xaa Xaa Xaa Xaa
        530                 535                 540

Xaa Ala Met Ala Glu Ala Phe Lys Ala Ala Lys Gly Glu
545                 550                 555
```